(12) United States Patent
Bonner et al.

(10) Patent No.: US 12,234,476 B2
(45) Date of Patent: Feb. 25, 2025

(54) VCN ENHANCER COMPOSITIONS AND METHODS OF USING THE SAME

(71) Applicant: bluebird bio, Inc., Cambridge, MA (US)

(72) Inventors: Melissa Bonner, Natick, MA (US); Olivier Negre, Cambridge, MA (US)

(73) Assignee: BLUEBIRD BIO, INC., Somerville, MA (US)

( * ) Notice: Subject to any disclaimer, the term of this patent is extended or adjusted under 35 U.S.C. 154(b) by 75 days.

(21) Appl. No.: 16/076,946

(22) PCT Filed: Feb. 10, 2017

(86) PCT No.: PCT/US2017/017372
§ 371 (c)(1),
(2) Date: Aug. 9, 2018

(87) PCT Pub. No.: WO2017/139576
PCT Pub. Date: Aug. 17, 2017

(65) Prior Publication Data
US 2019/0284533 A1    Sep. 19, 2019

Related U.S. Application Data

(60) Provisional application No. 62/294,615, filed on Feb. 12, 2016, provisional application No. 62/313,571, filed on Mar. 25, 2016, provisional application No. 62/417,085, filed on Nov. 3, 2016, provisional application No. 62/429,514, filed on Dec. 2, 2016.

(51) Int. Cl.
*C12N 15/867* (2006.01)
*C12N 5/0789* (2010.01)
*C12N 7/00* (2006.01)

(52) U.S. Cl.
CPC ......... *C12N 15/867* (2013.01); *C12N 5/0647* (2013.01); *C12N 7/00* (2013.01); *C12N 2501/02* (2013.01); *C12N 2501/999* (2013.01); *C12N 2510/00* (2013.01); *C12N 2740/15011* (2013.01); *C12N 2740/15041* (2013.01); *C12N 2740/16011* (2013.01); *C12N 2740/16041* (2013.01); *C12N 2740/16043* (2013.01)

(58) Field of Classification Search
CPC ........ C12N 15/867; C12N 2740/16043; C12N 2740/15011; C12N 2740/15041; C12N 2740/16011; C12N 2740/13041
See application file for complete search history.

(56) References Cited

U.S. PATENT DOCUMENTS

| | | | |
|---|---|---|---|
| 4,873,192 A | 10/1989 | Kunkel et al. |
| 5,460,964 A | 10/1995 | Mcglave et al. |
| 5,635,387 A | 6/1997 | Fei et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,759,793 A | 6/1998 | Schwartz et al. |
| 5,861,488 A | 1/1999 | Leboulch et al. |
| 5,864,029 A | 1/1999 | Townes et al. |
| 5,869,039 A | 2/1999 | Mandel et al. |
| 5,877,288 A | 3/1999 | Townes et al. |
| 5,994,136 A | 11/1999 | Naldini et al. |
| 6,013,516 A | 1/2000 | Verma et al. |
| 6,013,769 A | 1/2000 | Mandel et al. |
| 6,051,402 A | 4/2000 | Leboulch et al. |
| 6,057,117 A | 5/2000 | Harrison et al. |
| 6,608,063 B2 | 8/2003 | Nuss et al. |
| 6,610,719 B2 | 8/2003 | Paralkar et al. |
| 6,649,595 B2 | 11/2003 | Clackson et al. |
| 6,670,323 B1 | 12/2003 | Looker et al. |
| 6,682,907 B1 | 1/2004 | Charneau et al. |
| 6,747,037 B1 | 6/2004 | Old et al. |
| 6,822,112 B1 | 11/2004 | Sato et al. |
| 7,901,671 B2 | 3/2011 | Leboulch et al. |
| 8,029,780 B2 | 10/2011 | Kollet et al. |
| 8,241,903 B2 | 8/2012 | Lapidot et al. |
| 8,367,057 B2 | 2/2013 | Lapidot et al. |
| 8,858,928 B2 | 10/2014 | Denaro et al. |
| 9,061,031 B2 | 6/2015 | Denaro et al. |
| 9,068,199 B2 | 6/2015 | Leboulch et al. |
| 9,107,909 B2 | 8/2015 | Pelus et al. |
| 9,675,641 B2 | 6/2017 | Pelus et al. |
| 9,771,599 B2 | 9/2017 | Anastasov et al. |
| 9,988,644 B2 | 6/2018 | Heffner et al. |
| 10,501,759 B2 | 12/2019 | Heffner et al. |
| 10,907,177 B2 | 2/2021 | Heffner et al. |
| 11,326,183 B2 | 5/2022 | Bonner et al. |
| 11,834,668 B2 | 12/2023 | Heffner et al. |
| 2003/0166631 A1 | 9/2003 | Dumont et al. |

(Continued)

FOREIGN PATENT DOCUMENTS

| | | |
|---|---|---|
| AU | 2017217813 A1 | 9/2018 |
| EP | 3414321 A1 | 12/2018 |

(Continued)

OTHER PUBLICATIONS

Finotti et al. Journal of Blood Medicine 2015:6. pp. 69-85 (Year: 2015).*
Extended European Search Report issued in European Application No. 18751122.5 dated Oct. 16, 2020, 6 pages.
Kaur et al., "Addressing the challenge: current and future directions in ovarian cancer therapy," Curr Gene Ther. Dec. 2009;9(6):434-58.
Kotterman et al., "Engineering adeno-associated viruses for clinical gene therapy," Nat Rev Genet. Jul. 2014;15(7):445-51.
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.

(Continued)

*Primary Examiner* — Marcia S Noble
(74) *Attorney, Agent, or Firm* — Morse, Barnes-Brown & Pendleton, P.C.; Lisa M. Warren, Esq.; Erin E. Bryan, Esq.

(57) ABSTRACT

The invention provides improved gene therapy methods and compositions.

17 Claims, 27 Drawing Sheets

(56) References Cited

U.S. PATENT DOCUMENTS

| | | |
|---|---|---|
| 2003/0215452 A1 | 11/2003 | Carroll et al. |
| 2004/0092535 A1 | 5/2004 | Barsanti et al. |
| 2004/0209878 A1 | 10/2004 | Guzi et al. |
| 2005/0063958 A1 | 3/2005 | Symonds et al. |
| 2005/0079616 A1 | 4/2005 | Reubinoff et al. |
| 2005/0163760 A1 | 7/2005 | Cartier-Lacave et al. |
| 2006/0247214 A1 | 11/2006 | DeLong et al. |
| 2007/0087988 A1 | 4/2007 | Sawasdikosol et al. |
| 2008/0021078 A1 | 1/2008 | Tidmarsh et al. |
| 2008/0207584 A1 | 8/2008 | Habashita et al. |
| 2008/0261922 A1 | 10/2008 | Carley et al. |
| 2009/0092589 A1 | 4/2009 | Williams |
| 2010/0183519 A1 | 7/2010 | Katz et al. |
| 2010/0184032 A1 | 7/2010 | Georgantas et al. |
| 2010/0248254 A1 | 9/2010 | Perreault et al. |
| 2011/0224227 A1 | 9/2011 | Sharpless et al. |
| 2013/0209420 A1 | 8/2013 | Hampson et al. |
| 2014/0234278 A1 | 8/2014 | Heffner et al. |
| 2014/0255363 A1 | 9/2014 | Metelitsa et al. |
| 2015/0064788 A1 | 3/2015 | Anastasov et al. |
| 2015/0216903 A1 | 8/2015 | Heffner et al. |
| 2015/0266973 A1 | 9/2015 | Jarjour et al. |
| 2015/0307867 A1 | 10/2015 | Orkin et al. |
| 2018/0016600 A1 | 1/2018 | Anastasov et al. |
| 2018/0363004 A1 | 12/2018 | Heffner et al. |
| 2019/0078059 A1 | 3/2019 | Bonner et al. |
| 2019/0365814 A1 | 12/2019 | Diaconu et al. |
| 2020/0048657 A1 | 2/2020 | Heffner et al. |
| 2021/0171980 A1 | 6/2021 | Heffner et al. |
| 2024/0229070 A1 | 7/2024 | Heffner et al. |

FOREIGN PATENT DOCUMENTS

| | | | |
|---|---|---|---|
| FR | 3074189 A1 | 11/2017 | |
| RU | 2 280 074 C2 | 7/2006 | |
| WO | WO1992/011355 A1 | 7/1992 | |
| WO | WO1998/000541 A2 | 1/1998 | |
| WO | WO-2000/023567 A2 | 4/2000 | |
| WO | WO-2000/038663 A2 | 7/2000 | |
| WO | WO-2001/012596 A1 | 2/2001 | |
| WO | WO-2002/088346 A2 | 11/2002 | |
| WO | WO2004/098531 A2 | 11/2004 | |
| WO | WO-2006/047476 A2 | 5/2006 | |
| WO | WO-2007/071456 A1 | 6/2007 | |
| WO | WO-2007/112084 A2 | 10/2007 | |
| WO | WO2008/070310 A2 | 6/2008 | |
| WO | WO2008/073748 A1 | 6/2008 | |
| WO | WO2010/054271 A1 | 5/2010 | |
| WO | WO-2010/108028 A2 | 9/2010 | |
| WO | WO2013/049615 | 4/2013 | |
| WO | WO-2013/127964 A1 | 9/2013 | |
| WO | WO2014026110 A2 * | 2/2014 | ............ C12N 15/86 |
| WO | WO-2015/017214 A1 | 2/2015 | |
| WO | WO2015/059674 A1 | 4/2015 | |
| WO | WO 2015/104376 A1 | 7/2015 | |
| WO | WO2015/162594 A2 | 10/2015 | |
| WO | WO2016/014794 A1 | 1/2016 | |
| WO | WO 2016/201394 A1 | 12/2016 | |
| WO | WO-2017/139561 A1 | 8/2017 | |
| WO | WO-2018/148502 A1 | 8/2018 | |

OTHER PUBLICATIONS

Denning et al., "Optimization of the Transductional Efficiency of Lentiviral Vectors: Effect of Sera and Polycations", Mol Biotechnol (2013), 53: 308-314.

Blomer et al., "Highly Efficient and Sustained Gene Tranfer in Adult Neurons with a Lentivirus Vector," 1997, Journal of Virology, vol. 71, No. 9, p. 6641-6649.

Ikeda et al., "Gene transduction efficiency in cells of different species by HIV and EIAV vectors", Gene Therapy (2002), 9: 932-938.

Allegrucci et al., "Differences between human embryonic stem cell lines", Human Reproduction Update (2006), pp. 1-18; Advance Access published on Aug. 26, 2006.

Kolf et al., "Mesenchymal stromal cells. Biology of adult mesenchymal stem cells: regulation of niche, self-renewal and differentiation", Arthritis Research & Therapy (2007), 9: 204, 10 pages.

Hematti et al., "Retroviral transduction efficiency of G-CSF+SCF-mobilized peripheral blood CD34+ cells is superior to G-CSF or G-CSF+Flt3-L-mobilized cells in nonhuman primates", Blood (2003), 101(6): 2199-2205.

Akkina et al., "High-Efficiency Gene Transfer into CD341 Cells with a Human Immunodeficiency Virus Type 1-Based Retroviral Vector Pseudotyped with Vesicular Stomatitis Virus Envelope Glycoprotein G", Journal of Virology (1996), 70(4): 2581-2585.

International Preliminary Report on Patentability and Written Opinion of the International Searching Authority issued by the Korean Intellectual Property Office for corresponding International Application No. PCT/US2012/057987, dated Apr. 1, 2014, six pages.

International Search Report issued by the Korean Intellectual Property Office for corresponding International Application No. PCT/US2012/057987, dated Dec. 14, 2012, five pages.

Goessling et al., "Prostaglandin E2 Enhances Human Cord Blood Stem Cell Xenotransplants and Shows Long-Term Safety in Preclinical Nonhuman Primate Transplant Models," Cell Stem Cell (2011), 8: 445-458.

Pelus et al., "Pleiotropic Effects of Prostaglandin E2 in Hematopoiesis: Prostaglandin E2 and Other Eicosanoids Regulate Hematopoietic Stem and Progenitor Cell Function," Prostaglandins & Other Lipid Mediators 96:3-9 (Jun. 21, 2011).

Supplementary European Search Report for European Patent Application No. EP 12836507, dated Jan. 23, 2015.

Mostoslaysky, et al., "Efficiency of Transduction of Highly Purified Murine Hematopoietic Stem Cells by Lentiviral and Oncoretoviral Vectors Under Conditions of Minimal in Vitro Manipulation", Molecular Therapy, 11(6): 932-940 (2005).

Puthenveetil, Geetha, et al. "Successful correction of the human β-thalassemia major phenotype using a lentiviral vector." Blood 104.12 (2004): 3445-3453.

Chen, Wen Yong, et al. "Reactivation of silenced, virally transduced genes by inhibitors of histone deacetylase." Proceedings of the National Academy of Sciences 94.11 (1997): 5798-5803.

Tobias, Chris A. et al. "Improved recombinant retrovirai titers utilizing trichostatin A." Biotechniques 29:4 (2000): 884-891.

Sugimoto, "Signaling crosstalk regulates prostanoid actions in physiology and pathology," Experimental Medicine, 2009, vol. 27, No. 13, pp. 2047-2052.

Miyoshi, "Transduction of hematopoietic stem cells by lentiviral vectors," Virus, 2002, vol. 52, No. 2, pp. 225-231, abtract translation only.

Abeyta, Michael J., et al. "Unique gene expression signatures of independently-derived human embryonic stem cell lines." Human molecular genetics 13.6 (2004):601-608.

Alenzi, Fads Q.B., and Ali H. Bahkali. "Stem cells: Biology and clinical potential." African Journal of Biotechnology 10.86 (2011):19929-19940.

Bank, Arthur. "Hematopoietic stem cell gene therapy: selecting only the best," Journal of Clinical Investigation 112.10 (2003):1478.

Chattopadhyay, Anasuyam Tamal Raha, and M. S. Shaila. "Effect of single amino acid mutations in the conserved GDNQ motif of L protein of Rinderpest virus on RNA synthesis in vitro and in vivo". Virus research 99.2 (2004):139-145.

Dupuis, Fabienne, et al. “Prostaglandin E 2 Stimulates the Growth of Human Blood CD34 Progenitors.” Prostaglandins & other lipid mediators 55.2 (1998):179-186.

Feher, I. et al., “Prostaglandin E2 as stimulator of haemopoietic stem cell proliferation.” Nature 247.5442 (1974):550-551, Abstract.

Goichberg, Polina, et al. “CAMP-induced PKCζ activation increases functional CXCR4 expression on human CD34+ hematopoietic progenitors.” Blood107.3 (2006):870-879.

Hoggatt, Jonathan, et al. “Prostaglandin E2 enhances hematopoietic stem cell homing, survival, and proliferation.” Blood 113.22 (2009):5444-5455.

Horn, Peter A., et al. “Stem cell gene transfer-efficacy and safety in large animal studies.” Molecular Therapy 10.3 (2004):417-431.

(56) References Cited

OTHER PUBLICATIONS

Levesque, Jean-Pierre et al., "Mobilization of hematopoietic stem cells: state of the art." Current opinion in organ transplantation 13.1 (2003):53-58.
Li, Shengqiao, Mark Waer, and An D. Billiau. "Xenotransplantation: role of natural immunity." Transplant immunology 21.2 (2009):70-74.
Lord, Allegra M., Trista E. North, and Leonard I. Zon. "Prostaglandin E2: making more of your marrow." Cell Cycle 6.24 (2007):3054-3057.
McGiff, John C. "Prostaglandins, prostacyclins, and thromboxanes." Annual review of pharmacology and toxicology 21.1 (1981):479-509.
North, Trista E., et al. "Prostaglandin E2 regulates vertebrate haematopoietic stem cell homeostasis." Nature 447.7147 (2007):1007-1011.
Sato, Noboru, et al. "Molecular signature of human embryonic stem cells and its comparison with the mouse." Developmental biology 260.2 (2003):404-413.
Skolnick, Jeffrey, and Jacquelyn S. Fetrow. "From genes to protein structure and function: novel applications of computational approaches in the genomic era." Trends in biotechnology 18.1 (2000):34-39.
Smallwood, Sherin, et al. "Different substitutions at conserved amino acids in domains II and III in the Sendai L RNA polymerase protein inactivate viral RNA synthesis." Virology 304.1 (2002):135-145.
Sprangers, Ben, Waer, Mark, and Billiau, A. D. "Xenotransplantation: where are we it 2008?" Kidney international 74.1 (2008):14-21.
Taha, Masoumeh F. "Cell based-gene delivery approaches for the treatment of spinal cord injury and neurodegenerative disorders." Current stein cell research & therapy 5.1 (2010):23-36.
Tomasinsig, L., and M. Zanetti. "The cathelicidins-structure, function and evolution." Current Protein and Peptide Science 6.1 (2005):23-34.
Whitehurst, Christopher B., et al. "Single and multiple deletions in the transmembrane domain of the Sindbis virus E2 glycoprotein identify a region critical for normal virus growth." Virology 347.1 (2006):199-207.
Zhao, Wenxiu, et al. "Embryonic stem cell markers." Molecules 17.6 (2012):6196-6236.
Evers, Raymond, et al. "Transport of glutathione prostaglandin A conjugates by the multidrug resistance protein 1." FEBS letters 419.1 (1997):112-116.
Paumi, Christian M., et al. "Multidrug resistance protein (MRP) 1 and MRP3 attenuate cytotoxic and transactivating effects of the cyclopentenone prostaglandin, 15-deoxy-A12, 14prostaglandin J2 in MCF7 breast cancer cells." Biochemistry 42.18 (2003):5429-5437.
Sutton, Richard E., et al. "Transduction of human progenitor hematopoietic stem cells by human immunodeficiency virus type 1-based vectors is cell cycle dependent." Journal of Virology 73.5 (1999):3649-3660.
Sugimoto, Yukihiko et al., "Prostaglandin E receptors." Journal of Biological Chemistry 282.16 (2007):11613-11617.
Buczynski, M. W. et al., "An integrated omics analysis of eicosanoid biology" Journal of Lipid Research 50.7 (2009):1015-1038.
Follenzi, Antonia, et al. "Gene transfer by lentiviral vectors is limited by nuclear translocation and rescued by HIV-1 pol sequences." Nature Genetics 25.2 (2000):217-222.
Demaison, Christophe, et al. "High-level transduction and gene expression in hematopoietic repopulating cells using a human imunodeficiency virus type 1-based lentiviral vector containing an internal spleen focus forming virus promoter." Human Gene Therapy 13.7 (2002):803-813.
Notice of opposition to a European Patent in Patent No. EP2760994, on behalf of Muller Fottner Steinecke, dated Feb. 27, 2018.
Notice of opposition to a European Patent in Patent No. EP2760994, on behalf of Sagittarius Intellectual Property LLP, dated Feb. 28, 2018.

Paszkiet, BJ, et al., "Histone Deacetylation Inhibitors Enhance Lentiviral Vector Production and Infectivity," Molecular Therapy, vol. 5, special issue 5, S308, May 1, 2002.
Non-Final Office Action issued in U.S. Appl. No. 14/348,572, dated Nov. 6, 2015.
Final Office Action issued in U.S. Appl. No. 14/348,572, dated Apr. 26, 2016.
Non-Final Office Action issued in U.S. Appl. No. 14/348,572, dated Mar. 28, 2017.
Notice of Allowance and Fees Due issued in U.S. Appl. No. 14/348,572, dated Aug. 15, 2017.
Notice of Allowance and Fees Due issued in U.S. Appl. No. 14/348,572, dated Feb. 5, 2018.
International Search Report and Written Opinion for International Application No. PCT/US2018/017557, dated Jun. 14, 2018, 11 pages.
Hofig et al., "Poloxamer synperonic F108 improves cellular transduction with lentiviral vectors," J Gene Med, Aug. 2012, vol. 14, No. 8, pp. 549-560; abstract, p. 551, col. 1, para 4 to col. 2, para 1, p. 552, Table 1, p. 558, col. 1, para 1, Fig. 6b.
Albert, et al., "Site-specific integration of DNA into wild-type and mutant lox sites placed in the plant genome." Plant J. (1995); 7(4): 649-659.
Anastasov et al., "Optimized Lentiviral Transduction Protocols by Use of a Poloxamer Enhancer, Spinoculation, and scFv-Antibody Fusions to VSV-G," Methods Mol Biol. 2016;1448:49-61.
Arumugam, et al., "Genetic therapy for beta-thalassemia: from the bench to the bedside", Hematology Am Soc Hematol Educ Program. (2010); 445-50.
Beard, B.C. et al., "Efficient and stable MGMT-mediated selection of long-term repopulating stem cells in nonhuman primates", J Clin Invest. (2010), 120(7): 2345-2354.
Bell, et al., "The protein CTCF is required for the enhancer blocking activity of vertebrate insulators", Cell. (1999); 98(3): 387-96.
Belteki, et al., "Site-specific cassette exchange and germline transmission with mouse ES cells expressing φC31 integrase." Nature Biotechnology (2003); 21: 321-324.
Bethke et al., "Segmental genomic replacement by Cre-mediated recombination: genotoxic stress activation of the p53 promoter in single-copy transformants." Nucleic Acids Research (1997); 25(14): 2828-2834.
Bird, Robert E., et al. "Single-chain antigen-binding proteins." Science (1988); 242.4877: 423-426.
Burgess-Beusse, B. et al., "The insulation of genes from external enhancers and silencing chromatin", Proc Natl Acad Sci USA (2002), 99(Suppl 4):16433-16437.
Carell, Thomas, et al. "A novel procedure for the synthesis of libraries containing small organic molecules." Angewandte Chemie International Edition in English (1994); 33.20: 2059-2061.
Carell, Thomas, et al. "A Solution-Phase Screening Procedure for the Isolation of Active Compounds from a Library of Molecules." Angewandte Chemie International Edition in English (1994); 33.20: 2061-2064.
Cartier, N., et al., "Hematopoietic stem cell gene therapy with a lentiviral vector in X-linked adrenoleukodystrophy." Science (2009); 326(5954): 818-823.
Cavazzana-Calvo, M. et al., "Transfusion independence and HMGA2 activation after gene therapy of human β-thalassaemia", Nature (2010), 467(7313): 318-322.
Cavrois, et al., "A sensitive and specific enzyme-based assay detecting HIV-1 virion fusion in primary T lymphocytes." Nat Biotechnol. (2002); 20 (11): 1151-1154. Epub Sep. 30, 2002.
Chang, A.H., et al., "Erythroid-specific Human Factor IX Delivery From In Vivo Selected Hematopoietic Stem Cells Following Nonmyeloablative Conditioning in Hemophilia B Mice", Molecular Therapy (2008), 16(10): 1745-1752.
Chaudhary, Vuay K., et al. "A rapid method of cloning functional variable-region antibody genes in *Escherichia coli* as single-chain immunotoxins." Proceedings of the National Academy of Sciences (1990); 87.3: 1066-1070 (and correction).
Cho, Charles, et al. "An Unnatural Biopolymer," Science, vol. 261, Sep. 3, 1993, 1303-1304.

(56) References Cited

OTHER PUBLICATIONS

Chung, et al., "A 5' element of the chicken beta-globin domain serves as an insulator in human erythroid cells and protects against position effect in Drosophila", Cell. (1993); 74(3):505-14.
Chung, et al., "Characterization of the chicken beta-globin insulator", Proc Natl Acad Sci U S A. (1997); 94(2): 575-80.
Clever, J. et al., "RNA Secondary Structure and Binding Sites for gag Gene Products in the 59 Packaging Signal of Human Immunodeficiency Virus Type 1", J. of Virology (1995), 69(4): 2101-2109.
Cooper, Laurence JN, et al. "T-cell clones can be rendered specific for CD19: Toward the selective augmentation of the graft-versus-B-lineage leukemia effect." Blood (2003); 101.4: 1637-1644.
Cornetta, K. et al., "A pilot study of dose-intensified procarbazine, CCNU, vincristine for poor prognosis brain tumors utilizing fibronectin-assisted, retroviral-mediated modification of CD34+ peripheral blood cells with O6-methylguanine DNA methyltransferase", Cancer Gene Therapy (2006), 13: 886-895.
Cullen et al., "Regulatory pathways governing HIV-1 replication", Cell (1989), 58: 423-426.
Cullen, B.R., "Human immunodeficiency virus as a prototypic complex retrovirus", Journal of Virology (1991), 65(3): 1053-1056.
Dayhoff, M. et al., "A model of evolutionary change in proteins. In: Atlas of Protein Sequence and Structure", M.O. Dayhoff, (1978) ed., pp. 345-358. National Biomedical Research Foundation, Washington, DC.
Desjarlais et al. "Use of a zinc-finger consensus sequence framework and specificity rules to design specific DNA binding proteins." Proceedings of the National Academy of Sciences (1993); 90.6:2256-2260.
DeWitt, S. Hobbs, et al. "Diversomers: An approach to nonpeptide, nonoligomeric chemical diversity." Proceedings of the National Academy of Sciences USA (1993); 90.15: 6909-6913.
Dull et al., "A third-generation lentivirus vector with a conditional packaging system", Journal of Virology (1998), 72(11): 8463-8671.
Dunbar, C.E. et al., "Retroviral Transfer of the Glucocerebrosidase Gene into CD34+ Cells from Patients with Gaucher Disease: In Vivo Detection of Transduced Cells without Myeloablation", Human Gene Therapy (1998), 9(17): 2629-2640.
Finotti, et al., "Recent trends in the gene therapy of β-thalassemia", J Blood Med. (2015); 6: 69-85.
Gallop, Mark A., et al. "Applications of combinatorial technologies to drug discovery. 1. Background and peptide combinatorial libraries." Journal of Medicinal Chemistry (1994); 37.9: 1233-1251.
Ginn, et al., "Gene therapy clinical trials worldwide to 2012—an update." The Journal of Gene Medicine (2013); 15 (2): 65-77.
Groth, et al., "A phage integrase directs efficient site-specific integration in human cells." PNAS (2000); 97(11): 5995-6000.
Hacein-Bey-Abina, S., et al., "LMO2-Associated Clonal T Cell Proliferation in Two Patients after Gene Therapy for SCID-X1." Science (2003); 302 (5644): 415-419.
Hoban et al., "Genetic treatment of a molecular disorder: gene therapy approaches to sickle cell disease", Blood. (2016); 127(7): 839-848.
Hoess, et al., "The role of the loxP spacer region in P1 site-specific recombination," Nucleic Acids Res, 14 (1986), pp. 2287-2300.
Höfig et al., "Poloxamer synperonic F108 improves cellular transduction with lentiviral vectors,". J Gene Med. Aug. 2012; 14(8):549-60.
Huang and Yen, "Role of the hepatitis B virus posttranscriptional regulatory element in export of intronless transcripts", Mol. Cell. Biol. (1995), 15(7): 3864-3869.
Imren, S. et al., "Permanent and panerythroid correction of murine β thalassemia by multiple lentiviral integration in hematopoietic stem cells", Proc Natl Acad Sci U S A (2002), 99(22): 14380-14385.
Irion, S. et al., "Identification and targeting of the ROSA26 locus in human embryonic stem cells", Nat Biotechnol. (2007); 25(12):1477-1482.
Jackson, et al., "Internal initiation of translation in eukaryotes: the picornavirus paradigm and beyond", RNA. (1995); 1(10): 985-1000.

Jackson, et al., "The novel mechanism of initiation of picornavirus RNA translation", Trends Biochem Sci. (1990); 15(12): 477-483.
Kim, Yang-Gyun, et al., "Hybrid restriction enzymes: zinc finger fusions to Fok I cleavage domain." Proceedings of the National Academy of Sciences (1996); 93.3: 1156-1160.
Kozak, M., "An analysis of 5'-noncoding sequences from 699 vertebrate messenger RNAs", Nucleic Acids Res. (1987), 15(20):8125-48.
Kozak, M., "Point mutations define a sequence flanking the AUG initiator codon that modulates translation by eukaryotic ribosomes", Cell (1986), 44(2):283-92.
Kunkel, et al."Rapid and efficient site-specific mutagenesis without phenotypic selection", Methods in Enzymol. (1987); 154: 367-382.
Kunkel, TA. "Rapid and efficient site-specific mutagenesis without phenotypic selection", Proc Natl Acad Sci U S A. (1985); 82(2): 488-492.
Kutner et al., "Production, concentration and titration of pseudotyped HIV-1-based lentiviral vectors", Nature Protocols (2009); 4: 495-505.
Kutner, et al., "Simplified production andconcentration of HIV-1-based lentiviral vectors using HYPERFlask vessels and anion exchange membrane chromatography", BMC Biotechnol. (2009); 9:10. p. 1-7.
Landau and Littman. "Packaging system for rapid production of murine leukemia virus vectors with variable tropism." Journal of Virology (1992); 66.8: 5110-5113.
Landy, A. "Mechanistic and structural complexity in the site-specific recombination pathways of Int and FLP", Curr Opin Genet Dev. (1993); 3(5): 699-707.
Langer, et al., "A genetic screen identifies novel non-compatible loxP sites," Nucleic Acids Res, 30 (2002), pp. 3067-3077.
Lee et al., "Role of nucleotide sequences of loxP spacer region in Cre-mediated recombination." Gene (1998); 216 (1): 55-65.
Levasseur, D.N. et al., "Correction of a mouse model of sickle cell disease: lentiviral/antisickling beta-globin gene transduction of unmobilized, purified hematopoietic stem cells", Blood (2003), 102(13): 4312-4319.
Liu and Mertz, "HnRNP L binds a cis-acting RNA sequence element that enables intron-dependent gene expression", Genes & Dev. (1995), 9: 1766-1780.
Liu, Qiang, et al. "Design of polydactyl zinc-finger proteins for unique addressing within complex genomes." Proceedings of the National Academy of Sciences (1997); 94.11: 5525-5530.
Lowy, et al., "Isolation of transforming DNA: cloning the hamster aprt gene", Cell. (1980); 22(3): 817-823.
MaGuire, A.M. et al., "Safety and efficacy of gene transfer for Leber's congenital amaurosis", N Engl J Med. (2008), 358(21): 2240-2248.
International Search Report and Written Opinion for International Application No. PCT/US2017/017372, dated Apr. 27, 2017, 13 pages.
Bertrand et al., "Induction of a Common Pathway of Apoptosis by Staurosporine," Experimental Cell Research, vol. 211, Issue 2, Apr. 1994, pp. 314-321.
Buschke et al., "Cell death, non-invasively assessed by intrinsic fluorescence intensity of NADH, is a predictive indicator of functional differentiation of embryonic stem cells," Biol Cell. Jun. 2012; 104(6): 352-364.
Extended European Search Report issued in European Application No. 17750819.9 dated Aug. 27, 2019, 8 pages.
Hughes et al., "Regulation of pluripotent cell differentiation by a small molecule, taurosporine," Differentiation, 87, Feb. 28, 2014, pp. 101-110.
Lai et al., "T and B lymphocyte differentiation from hematopoietic stem cell," Seminars in Immunology, vol. 20, No. 4, Aug. 1, 2008, 6 pages.
Rodriguez et al., "Induction of Alkalinization in Cultured Renal Cells (MDCK Line) by Prostaglandin E2," Prostaglandins, vol. 49, No. 2, Feb. 1, 1995, 13 pages.
International Search Report and Written Opinion for International Application No. PCT/US2017/017351, dated Apr. 28, 2017, 11 pages.

(56) References Cited

OTHER PUBLICATIONS

Liu et al. "Prostaglandin E2 induces hypoxia-inducible factor-1alpha stabilization and nuclear localization in a human prostate cancer cell line," J Biol Chem, Oct. 24, 2002 (Oct. 24, 2002), vol. 277, No. 51, pp. 50081-50086. entire document.
Yoder et al. "HIV envelope-CXCR4 signaling activates cofilin to overcome cortical actin restriction in resting CD4 T cells," Cell, Sep. 5, 2008 (Sep. 5, 2008), vol. 134, No. 5, pp. 782-792. entire document.
Zhao, Xiao-yu, et al. "Enhancing Lentiviral Vector Transduction Efficiency for Facilitating Gene Therapy." *China Biotechnology* 41.8 (2021): 52-58.
Notice of Allowance and Fee(s) Due issued in Application No. U.S. Appl. No. 16/076,950, dated Jan. 3, 2022.
Notice of Allowability issued in Application No. U.S. Appl. No. 16/076,950, dated Mar. 10, 2022.
Notice of Allowance for U.S. Appl. No. 17/125,930 dated Jul. 25, 2023.
Corrected Notice of Allowability for U.S. Appl. No. 17/125,930 dated Aug. 17, 2023.
The European Agency for the Evaluation of Medicinal Products (Feb. 1997, Committee for Proprietary Medicinal Products, pp. 1-6).
Non-Final Office Action for U.S. Appl. No. 17/125,930, dated Jan. 6, 2023.
Xinchen Sun, "Clinical Molecular Oncology," Southeast University Press (2008).
Case, et al. "Stable transduction of quiescent CD34 + CD38 human hematopoietic cells by HIV-1- based lentiviral vectors," Proceedings of the National Academy of Sciences, 96.6:2988-2993, (1999).
De Waart, et al., "Multidrug resistance associated protein 2 mediates transport of prostaglandin E2," Liver International, 26.3:362-368, (2006).
Gao, et al., "Changes of T Cell Subsets in the Peripheral Blood of Mice after Mobilization of Hematopoietic Stem Cells by G-CSF and GM-CSF," Acta Academiae Medicine Xuzhou, Jul. 2007, DD. 1-2, vol. 27, No., 7. One page Abstract only.
Giry-Laterriere, et al., Chapter 8 pp. 183-209; Lentiviral Vectors. In: Merten OW., Al-Rubeai M. (eds) Viral Vectors for Gene Therapy. Methods in Molecular Biology (Methods and Protocols), vol. 737. Humana Press; ISBN: 978-1-61779-094-2. 2011.
Hayakawa, et al., "Transient in Vivo-Globin Production After Lentiviral Gene Transfer to Hematopoietic Stem Cells in the Non-human Primate," HumGene Ther., 20(6):563-72, (Jun. 2009).
Heffner, et al., "Prostaglandin E2 Increases Lentiviral Vector Transduction Efficiency of Adult Human Hematopoietic Stem and Progenitor Cells," Mol Ther, 89926, 1:320-328, (2018).
Hoggart, "Eicosanoid Regulation of Hematopoietic, Stem, and ProgenPubitor Cell Function," Permanent link: http://hdl.handle.net/1805/2206 date: Jul. 21, 2010.
Li, et al., "Optimal promoter usage for lentiviral vector-mediated transduction of cultured central nervous system cells," J. Neurosci Methods, 189(1):56-64, (May 30, 2010).
Liu, et al., "Identification of parameters required for efficient lentiviral, vector transduction and engraftment of human cordblood CD34+ NOD/SCID-re-populating cells," Exp. Hematrol. 35:947-956, (2008).
Malik, et al., "Successful Correction of the Human Cooley's Anemia—Thalassemia Major Phenotype Using a Lentiviral Vector Flanked by the Chicken Hypersensitive Site 4 Chromatin Insulator," Annals of the New York Academy of Sciences (2005), Annals of the New York Academy of Sciences vol. 1054, Cooley's Anemia: Eighth Symposium pp. 238-249, Nov. 2005.
May, et al., "Therapeutic haemoglobin synthesis in β-thalassaemic mice expressing lentivirus-encoded human beta-globin," Nature, 406(6791):82-86, (2000).
McLeod, et al., "Identification of the crossover site during FLP-mediated recombination in the Saccharomyces cerevisiae plasmid 2 microns circle," Mol. Cell. Biol, 6(10):3357-3367, (1986).

Miller, "Human gene therapy comes of age," Nature, 11:357(6378):455-60, (1992).
Milsom, et al., "Reciprocal relationship between 06-Methylguanine-DNA methyltransferase P140K expression level and chemoprotection of hematopoietic stem cells," Cancer Res., 68(15):6171- 6180, (2008).
Naldini, et al., "Efficient transfer, integration, and sustained long-term expression of the transgene in adult rat brains injected with a lentiviral vector," Proc Natl Acad Sci USA, 93(21):11382-11388, (1996).
Naldini, et al., "In vivo gene delivery and stable transduction of nondividing cells by a lentiviral vector," Science, 272(5259):263-267, (1996).
Naldini, "Gene therapy returns to centre stage," Nature, 526(7573):351-360, (2015).
Naldini, "Lentiviruses as gene transfer agents for delivery to non-dividing cells," Current Opinion Biotechnology, 5:457-63, (1998).
Nguyen, et al., "Highly efficient lentiviral vector-medicated transduction of nondividing, fully reimplantable primary hepatocytes, " Molecular therapy 6.2:199-209, (2002).
Non-Final Office Action for U.S. Appl. No. 15/997,643, dated May 9, 2019.
Non-Final Office Action for U.S. Appl. No. 16/665,892, dated Apr. 29, 2020.
Notice of Allowance for U.S. Appl. No. 15/997,643, dated Sep. 24, 2019.
Notice of Allowance for U.S. Appl. No. 16/665,892, dated Oct. 8, 2020.
Notice of appeal of opposition decision of Patent No. EP 2760994, dated Jan. 16, 2020.
Notice of opposition to a European Patent in Patent No. EP 3269802, on behalf of HGF Limited, dated Jul. 21, 2020.
Notice of opposition to a European Patent in Patent No. EP 3269802, on behalf of Script IP Limited, dated Jul. 23, 2020.
Patel, et al., "Impact of chimeric immune receptor extracellular protein domains on T cell function," Gene Ther, 6(3): 412-419, (1999).
Pawliuk, et al. "Correction of sickle cell disease in transgenic mouse models by gene therapy." Science, 294.5550:2368-2371, (2001).
Pestina, et al., "Correction of murine sickle cell disease using gamma-globin lentiviral vectors to mediate high-level expression of fetal hemoglobin," Molecular Therapy, 17(2): 245-252, (2009).
Piacibello, et al., "Lentiviral gene transfer and ex vivo expansion of human primitive stem cells capable of primary, secondary, and tertiary multilineage repopulation in NOD/SCID mice," Blood 100:4391-4400, (2002).
Pomerantz, et al. "Structure-based design of transcription factors," Science, 267.5194:93-96, (1995).
PubChem entry for Thromoxane B2 (from printed 2018 https://pubchem.ncbi.nlm.nih.gov/compound/thromboxane_B2) printed 2018.
Reddy, et al., "Histone Deacetylase Inhibitor Suberoylanilide Hydroxamic Acid Reduces Acute Graft-Versus-Host Disease and Preserves Graft-Versus-Leukemia Effect," Proc Natl Acad Sci USA, 101(11):3921-3926, (Mar. 16, 2004).
Robertson, et al., "Thromboxane A2 in vasotonic angina pectoris: evidence from direct measurements and inhibitor trials," New England Journal of Medicine, 304(17):998-1003, (1981).
Santoni De Sio et al., "Short-term culture of human CD34+ cells for lentiviral gene transfer," Methods Mol Biol., 506:59-70, (2009).
Sauer, "Site-specific recombination: developments and applications," Curr Opin Biotechnol., 5(5): 521-527, (1994).
Schlake, et al., "Use of mutated FLP recognition target (FRT) sites for the exchange of expression cassettes at defined chromosomal loci," Biochemistry, 33(43):12746-12751, (1994).
Scott, et al., "Gene therapy's out-of-body experience," Nat Biotechnol., 34(6):600-607, (2016).
Senecoff, et al., "DNA Recognition by the FLP Recombinase of the Yeast 2 μ Plasmid," J. Mol. Biol., 201(2):405-421, (1988).
Sibbald, et al., "Doctors asked to take pledge to shun drug company freebies," CMAJ, 164(4):531, (2001).
Sirin, et al., "Regulating gene expression using self-inactivating lentiviral vectors containing the mifepristone-inducible system," Gene, 323:67-77, (2003).

(56) References Cited

OTHER PUBLICATIONS

Soneoka, et al. "A transient three-plasmid expression system for the production of high titer retroviral vectors," *Nucleic Acids Research*, 23(4):628-633, (1995).

Structural Similarity of Prostaglandins.

Technical Resource document detailing formulation of Gibco TM—IMDM (Catalogue No. 12440-ThermoFisher Scientific) / https://www.thermofisher.com/uk/en/home/technical-resources/media-formulations.76 html.

Tesio, et al., "Substained Long-Term Engraftment and Transgene Expression of Peripheral Blood CD34+ Cells Transduced with Third-Generation Lentiviral Vectors," *Stem Cells*, 26:1620-1627, (2008).

Thyagarajan, et al., "Site-specific genomic integration in mammalian cells mediated by phage @C31 integrase," *Mol Cell Biol.*, 21(12):3926-3934, (2001).

Uchida, et al. "Optimal conditions for lentiviral transduction of engrafting human CD34+ cells." *Gene Therapy*, 18(11):1078-1086, (2011).

Uchida, et al., "Development of a human immunodeficiency virus type 1-based lentiviral vector that allows efficient transduction of both human and rhesus blood cells," *Journal of Virology*, 83(19)9854-9862, (2009).

Ueno, et al., "Possible pathogenesis of acquired immune deficiency syndrome in homosexual males: an unexpected action of seminal prostaglandin E2 on AIDS-virus infection," *Advances in Prostaglandin, Thromboxane, and Leukotriene Research*, 17:151-154, (1987).

White, et al., "Comparison of the glycosyl-phosphatidylinositol cleavage/attachment site between mammalian cells and parasitic protozoa," *J Cell Sci.*, 113(Pt 4):721-727, (2001).

Wigler, et al., "Transfer of purified herpes virus thymidine kinase gene to cultured mouse cells," *Cell*, 11:223-232, (1977).

Xinhua, "X-Linked Adrenoleukodystrophy," *Chinese Journal of Practical Pediatrics*, 24(7):504-507, (2009) (with English translation of relevant portion).

Zennou, et al., "HIV-1 genome nuclear import is mediated by a central DNA flap," *Cell*, 101(2):173-185, (2000).

Zhan, et al., "Insulator: from chromatin domain boundary to gene regulation," *Hum Genet.*, 109(5):471-478, (2001).

Zhou, et al. "Quantitative shearing linear amplification polymerase chain reaction: an improved method for quantifying lentiviral vector insertion sites in transplanted hematopoietic cell systems," *Hum Gene Ther Methods*, 26(1):4-12, (2015).

Zuckermann, et al. "Discovery of nanomolar ligands for 7-transmembrane G-protein-coupled receptors from a diverse N-(substituted) glycine peptoid library," *Journal of Medicinal Chemistry*, 37(17):2678-2685, (1994).

Zufferey, et al., "Multiply attenuated lentiviral vector achieves efficient gene delivery in vivo," *Nat Biotechnol.*, 15(9):871-875, (1997).

Zufferey, et al., "Woodchuck hepatitis virus posttranscriptional regulatory element enhances expression of transgenes delivered by retroviral vectors," *J. Virol.*, 73(4):2886-2892, (1999).

\* cited by examiner

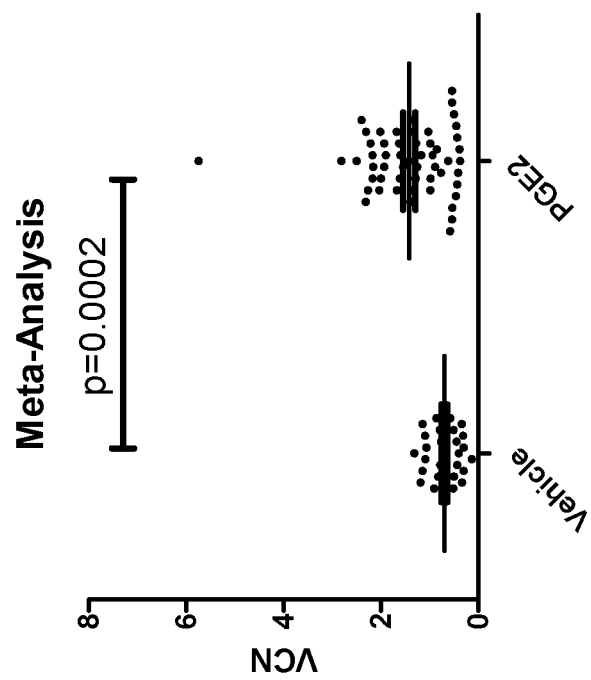
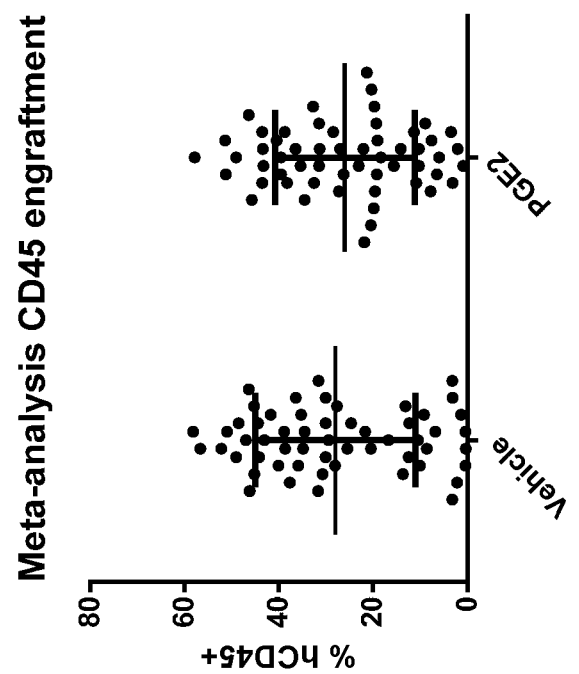
FIG. 1

*p<0.05 compared to 1 (PS - standard transduction)

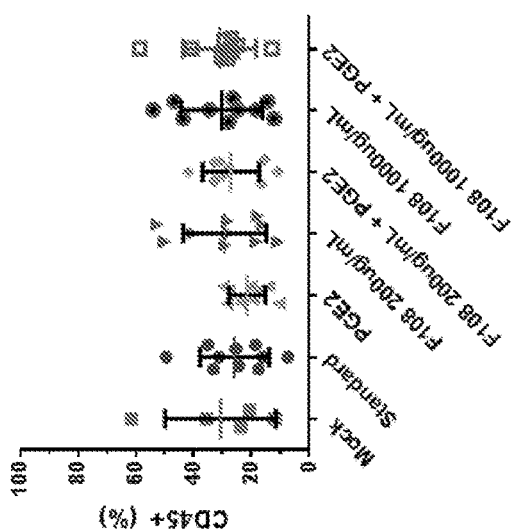
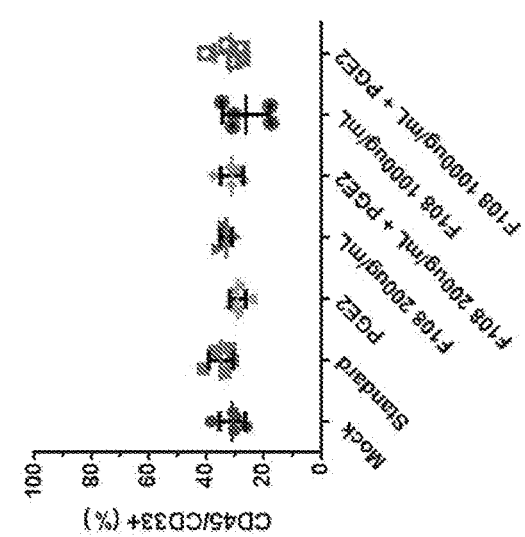
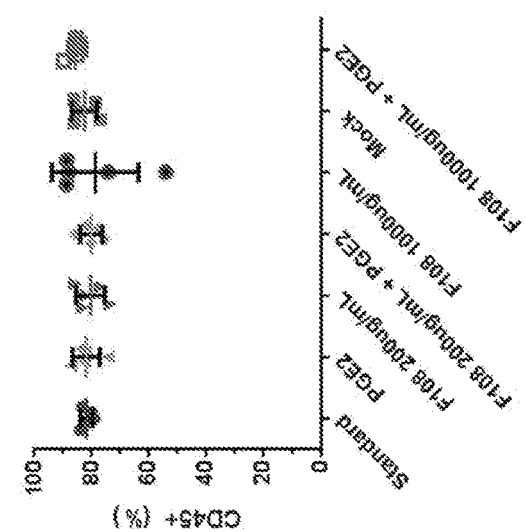
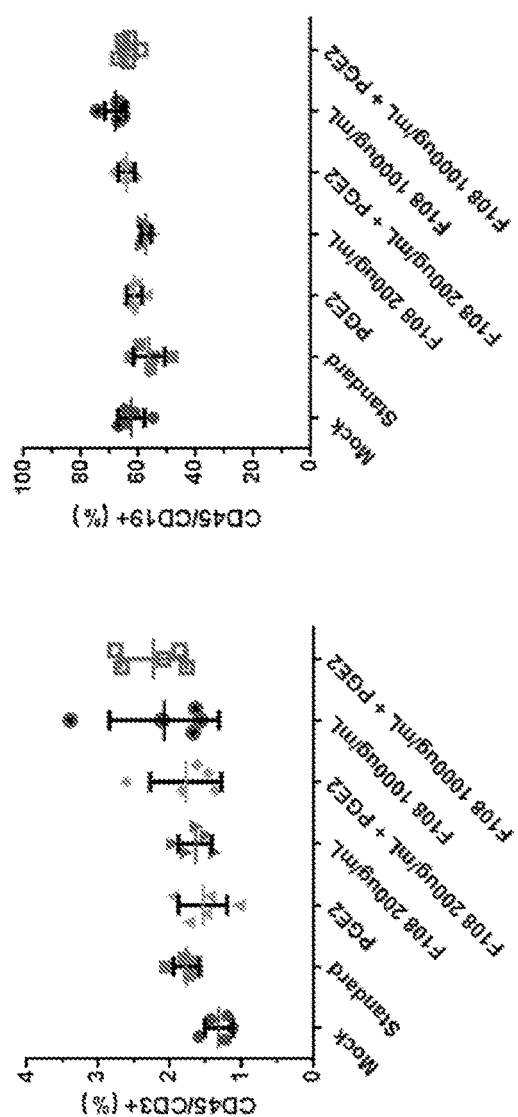

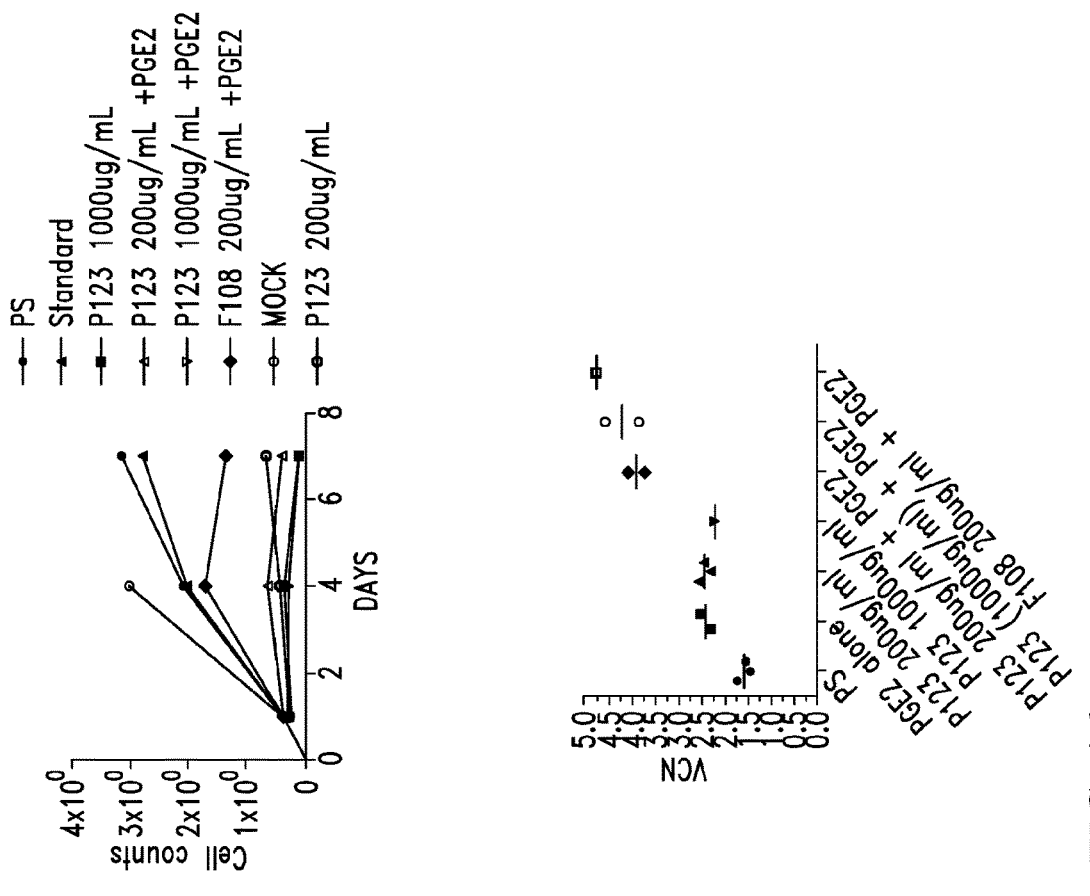
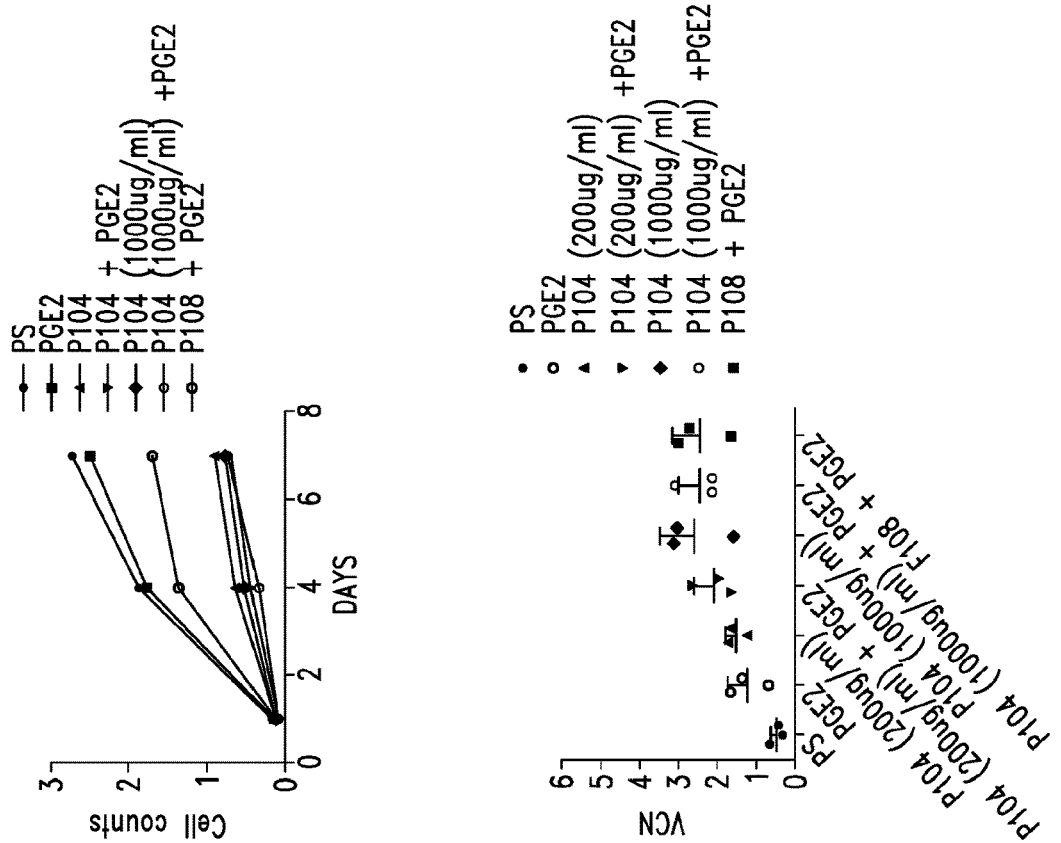
FIG. 16

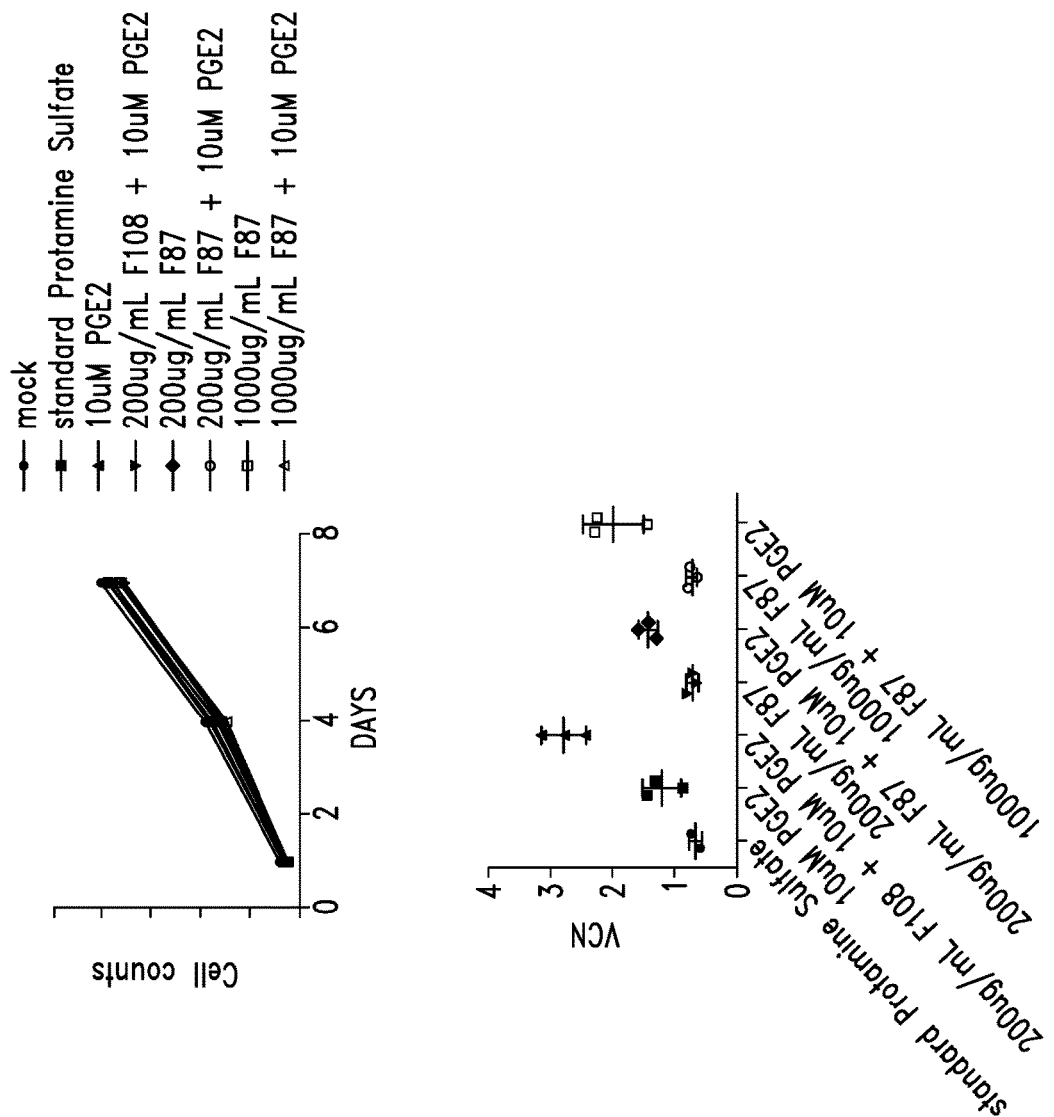
FIG. 17
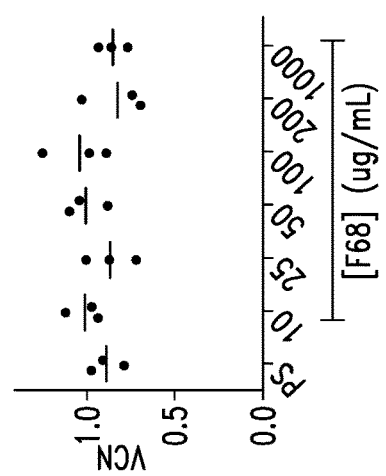

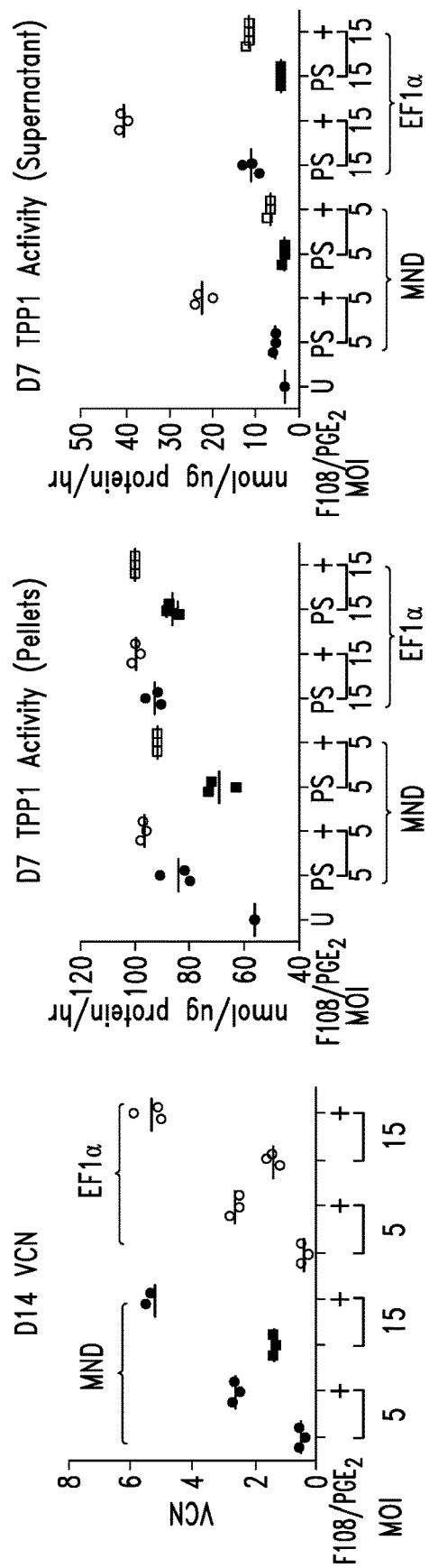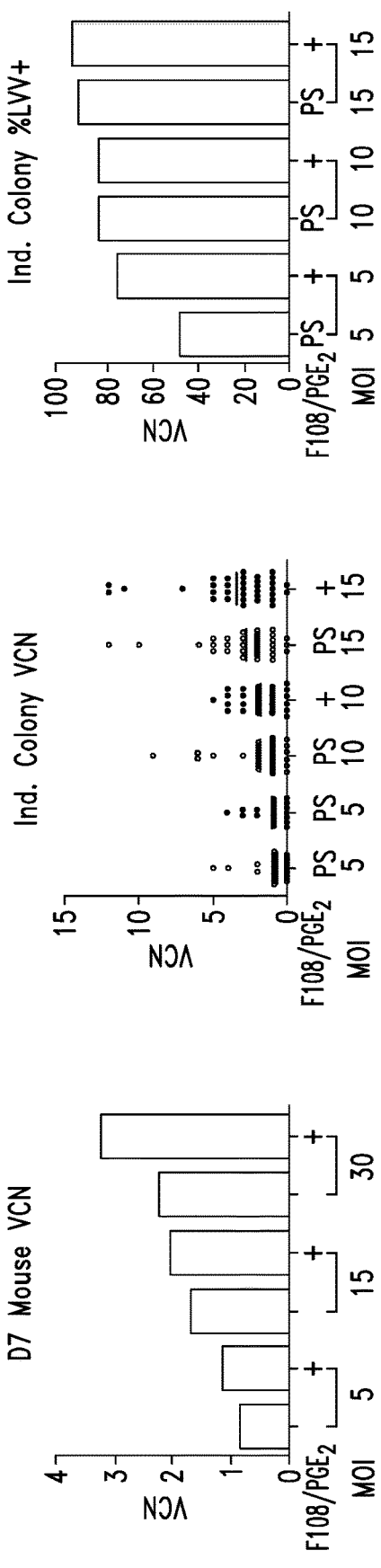
FIG. 25

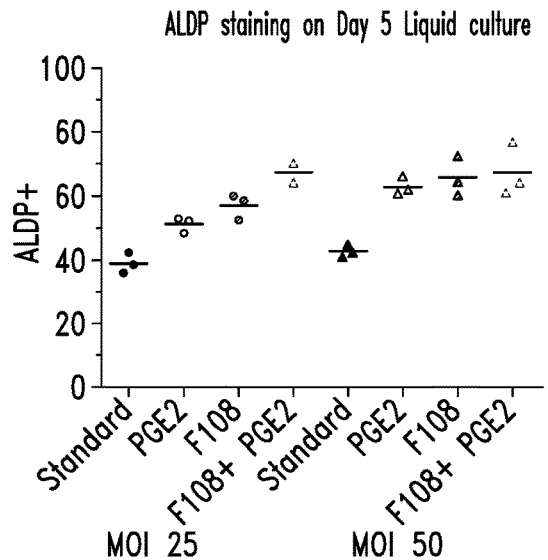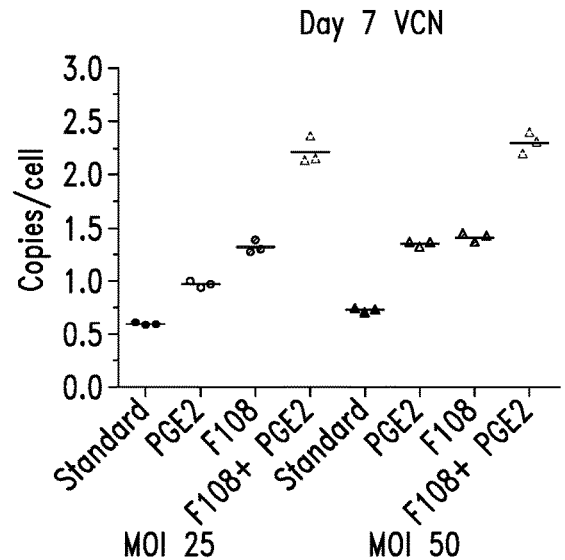
FIG. 26A  FIG. 26B
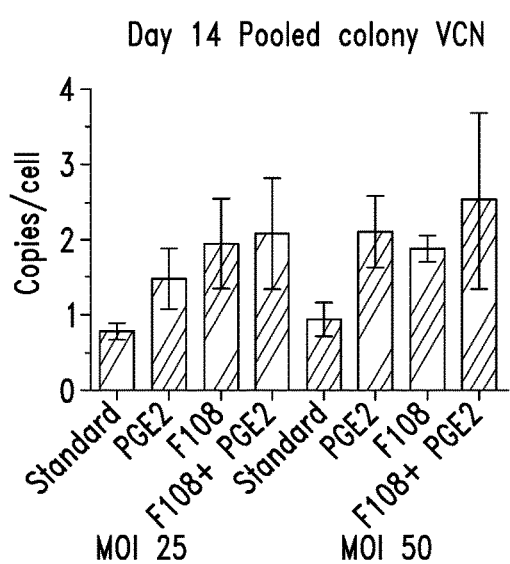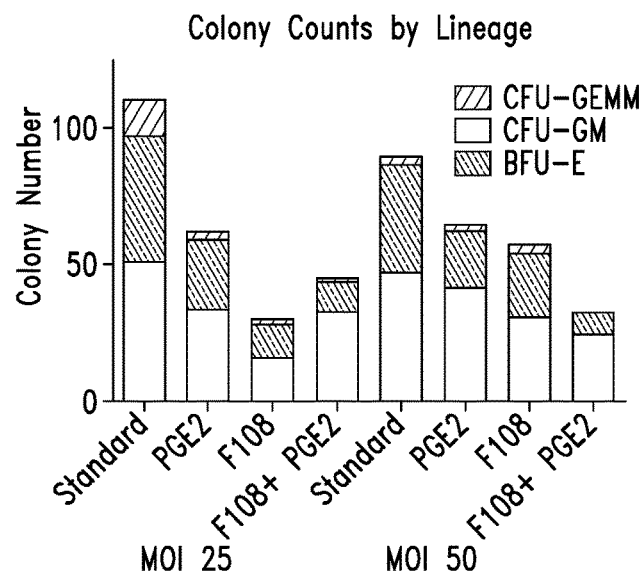
FIG. 26C  FIG. 26D

VCN ENHANCER COMPOSITIONS AND METHODS OF USING THE SAME

CROSS REFERENCE TO RELATED APPLICATIONS

This application is a U.S. national phase application of International PCT Patent Application No. PCT/US2017/017372, which was filed on Feb. 10, 2017, which claims the benefit under 35 U.S.C. § 119 (e) of U.S. Provisional Application No. 62/429,514, filed Dec. 2, 2016, 62/417,085, filed Nov. 3, 2016, U.S. Provisional Application No. 62/313,571, filed Mar. 25, 2016, and U.S. Provisional Application No. 62/294,615, filed Feb. 12, 2016, each of which is incorporated by reference herein in its entirety.

BACKGROUND

Technical Field

The present invention generally relates, in part, to improved gene therapy compositions and methods of making the same.

Description of the Related Art

Gene therapy holds enormous potential for a new era in human medicine. Gene therapy methodologies will allow treatment for conditions that have not been addressable by standard medical practice. However, the Food and Drug Administration (FDA) has not yet approved any human gene therapy product for sale. Current gene therapy is experimental and has had mixed results in clinical trials. Ginn et al., *J Gene Med* 2013 and Naldini et al., *Nature Review* 2015.

In 1999, gene therapy suffered a major setback with the death of 18-year-old Jesse Gelsinger. Jesse was participating in a gene therapy trial for ornithine transcarboxylase deficiency (OTCD). He died from multiple organ failures 4 days after starting the treatment. His death is believed to have been triggered by a severe immune response to the adenovirus carrier. Sibbald et al., *CMAJ* 2001.

Another major blow came in January 2003, when the FDA placed a temporary halt on all gene therapy trials using retroviral vectors in blood stem cells. FDA took this action after it learned that a second child treated in a French gene therapy trial had developed a leukemia-like condition. Hacein-Bey-Abina et al., *Science* 2003. Both this child and another who had developed a similar condition in August 2002 had been successfully treated by gene therapy for X-linked severe combined immunodeficiency disease (X-SCID), also known as "bubble boy syndrome." FDA's Biological Response Modifiers Advisory Committee (BRMAC) met at the end of February 2003 to discuss possible measures that could allow a number of retroviral gene therapy trials for treatment of life-threatening diseases to proceed with appropriate safeguards. In April of 2003, the FDA eased the ban on gene therapy trials using retroviral vectors in blood stem cells.

Recently, however, several groups have led moderately successful gene therapy trials in combating several diseases. In, 2008, UK researchers from the UCL Institute of Ophthalmology and Moorfields Eye Hospital NIHR Biomedical Research Centre announced a successful gene therapy clinical trial for treatment of Leber's congenital amaurosis, a type of inherited blindness. The results showed that the experimental treatment is safe and can improve sight (Maguire et al., *N Engl J Med.* 358(21):2240 (2008)).

In 2009, a French group of scientists reported using hematopoietic stem cell mediated gene therapy to successfully treat X-linked adrenoleukodystrophy (ALD). Cartier et al., *Science* 2009. Autologous stem cells were removed from the patients, genetically corrected ex vivo and then re-infused into the patients after they had received myeloablative treatment. Over a span of 24 to 30 months of follow-up, polyclonal reconstitution, with 9 to 14% of granulocytes, monocytes, and T and B lymphocytes expressing the ALD protein was detected. These results strongly suggest that hematopoietic stem cells were transduced in the patients. Beginning 14 to 16 months after infusion of the genetically corrected cells, progressive cerebral demyelination in the two patients stopped.

In 2011, Neurologix, Inc. announced positive results in a Phase 2 trial of its investigational gene therapy for advanced Parkinson's disease (PD), NLX-P101. Study participants who received NLX-P101 experienced statistically significant and clinically meaningful improvements in off-medication motor scores compared to control subjects who received sham surgery. In the trial, this benefit was seen at one month and continued virtually unchanged throughout the six month blinded study period. The results also demonstrated a positive safety profile for NLX-P101, with no serious adverse events related to the gene therapy or surgical procedure reported. Patients enrolled in the trial had moderate to advanced PD and were not adequately responsive to current therapies.

Recent progress in the field of gene therapy has raised the hope that patients afflicted with hemoglobinopathies such as β-thalassemia and sickle cell anemia will benefit from novel therapeutic approaches. Cavazzana-Calvo et al., *Nature* 2010. Transplantation of hematopoietic cells (HSCs) modified with lentiviral vectors carrying the β-globin gene has resulted in long-term correction of several mouse models of hemoglobin disorders, e.g., Imren et al., *Proc Natl Acad Sci USA.* 2002; 99(22):14380-14385; Malik et al., *Ann NY Acad Sci.* 2005; 1054:238-249; May et al., *Nature.* 2000; 406 (6791):82-86; Pawliuk et al., *Science.* 2001; 294(5550): 2368-2371).

Although the main advantages of infusing genetically modified autologous cells are to avoid the risks of GVHD and immunosuppressive pretransplant conditioning as well as to address the lack of compatible donors, current therapy faces at least three substantive caveats: the requirement for toxic myeloablation (Dunbar et al,. *Hum Gene Ther.* 1998; 9(17):2629-2640); current gene transfer methods are unable to transduce more than a fraction of hematopoietic stem cells (HSCs) (Santoni de Sio and Naldini, *Methods Mol Biol.* 2009; 506:59-70); vector copy numbers of transduced HSCs are often at the lower end for therapeutic efficacy; and various in vivo selection strategies available suffer from suboptimal efficacy and safety (Beard et al., *J Clin Invest.* 2010; 120(7):2345-2354; Cornetta et al., *Cancer Gene Ther.* 2006; 13(9):886-895; Milsom et al., *Cancer Res.* 2008; 68(15): 6171-6180).

Currently, there are a vast number of protocols used among research and clinical groups for introducing lentiviral gene therapy vectors into target cells. Historically, high efficiency gene transfer has been achieved in various cell types using different strategies. However, most of these strategies, e.g., polycations, cationic liposomes, polybrene, involve the use of adjuvant treatments are toxic for the cells, limiting their use with sensitive target cells of primary origin, like hematopoietic stem and progenitor cells.

Hematopoietic stem and progenitor cells are known to be notoriously difficult to efficiently transduce and thus, inefficient transduction is one of the prime limiting factors preventing HSC-based gene therapy from entering the clinic. Inefficient transduction also increases the expense of developing gene therapies because large amounts of vector are required to generate the requisite amount of transduced cells. Thus, not only would increasing the transduction efficiency of hematopoietic stem and progenitor cells provide quantum clinical benefits, but it would reduce the amount of virus required to generate the drug products and thus, reduce the costs of clinical trials.

BRIEF SUMMARY

Improved gene therapies are contemplated herein. In particular embodiments, gene therapies comprise hematopoietic stem and progenitor cell compositions with increased therapeutic efficacy and methods of making and using the same. In other particular embodiments, the present invention contemplates compositions and methods for increasing transduction efficiency and VCN of human hematopoietic stem and progenitor cells (HSPCs) to yield improved gene therapy compositions.

In various embodiments, the present invention contemplates, in part, a population of hematopoietic cells comprising hematopoietic stem and progenitor cells (HSPCs) transduced with a retroviral vector, wherein at least 50% of the HSPCs are transduced and wherein the HSPCs have an average vector copy number (VCN) of about 0.5 to 5.

In particular embodiments, the retroviral vector is a lentiviral vector.

In particular embodiments, the lentiviral vector transduces the HSPCs at a multiplicity of infection (MOI) of about 10 to about 30.

In particular embodiments, the lentiviral vector transduces the HSPCs at a multiplicity of infection (MOI) of about 10 to about 25.

In particular embodiments, the lentiviral vector transduces the HSPCs at a multiplicity of infection (MOI) of about 10 to about 20.

In particular embodiments, the HSPCs comprise $CD34^+$ cells or $CD133^+$ cells.

In certain embodiments, the HSPCs comprise $CD34^+$ $CD38^{Lo}CD90^+CD45RA^-$ cells.

In additional embodiments, at least 75% of the cells have been transduced.

In additional embodiments, at least 90% of the cells have been transduced.

In particular embodiments, the average VCN is at least 1.0.

In particular embodiments, the average VCN is at least 1.5.

In particular embodiments, the average VCN is at least 2.0.

In particular embodiments, the average VCN is at least 2.5.

In certain embodiments, viability of the population of cells is at least 75%.

In additional embodiments, viability of the population of cells is at least 85%.

In additional embodiments, viability of the population of cells is at least 95%.

In further embodiments, the endotoxin level of the population of hematopoietic cells is at most 5.0 EU/mL.

In certain embodiments, endotoxin level of the population of hematopoietic cells is most 0.5 EU/mL.

In additional embodiments, the population of cells comprises at least $1 \times 10^6$ HSPCs cells.

In particular embodiments, the population of cells comprises at least $1 \times 10^7$ HSPCs cells.

In particular embodiments, the population of cells comprises at least $1 \times 10^8$ HSPCs cells.

In some embodiments, the population of cells comprises at least $1 \times 10^9$ HSPCs cells.

In particular embodiments, the lentiviral vector encodes an ATP-binding cassette, sub-family D, member 1 (ABCD1) polypeptide.

In further embodiments, the lentiviral vector comprises a myeloproliferative sarcoma virus enhancer, negative control region deleted, d1587rev primer-binding site substituted (MND) promoter or transcriptionally active fragment thereof operably linked to a polynucleotide encoding an ATP-binding cassette, sub-family D, member 1 (ABCD1) polypeptide.

In certain embodiments, the lentiviral vector encodes adenosine deaminase.

In certain embodiments, the lentiviral vector comprises an elongation factor 1 alpha promoter operably linked to a polynucleotide encoding adenosine deaminase.

In certain embodiments, the lentiviral vector encodes interleukin 2 receptor gamma.

In certain embodiments, the lentiviral vector comprises an elongation factor 1 alpha promoter operably linked to a polynucleotide encoding interleukin 2 receptor gamma.

In particular embodiments, the lentiviral vector encodes tripeptidyl peptidase 1.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding tripeptidyl peptidase 1.

In particular embodiments, the lentiviral vector encodes alpha-L iduronidase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding alpha-L iduronidase.

In particular embodiments, the lentiviral vector encodes iduronate 2-sulfatase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding iduronate 2-sulfatase.

In certain embodiments, the lentiviral vector comprises a promoter comprising one or more elements of a human β-globin LCR.

In some embodiments, the human β-globin LCR comprises DNase I hypersensitive site 2, 3, and 4 from the human β-globin LCR.

In particular embodiments, the lentiviral vector further comprises a human β-globin 3' enhancer element.

In additional embodiments, the gene of interest encodes an antisickling protein or a globin gene.

In particular embodiments, the gene of interest encodes a human β-globin protein, a human β-globin protein, a human γ-globin protein, a human $β^{A-T87Q}$-globin protein, a human $D^{A-G16D/E22A/T87Q}$-globin protein, or a human $β^{A-T87Q/K95E/K120E}$-globin protein.

In particular embodiments, the lentiviral vector is an AnkT9W vector, a T9Ank2W vector, a TNS9 vector, a lentiglobin HPV569 vector, a lentiglobin BB305 vector, a BG-1 vector, a BGM-1 vector, a d432βAγ vector, a mLARβΔγV5 vector, a GLOBE vector, a G-GLOBE vector, a βAS3-FB vector, a V5 vector, a V5m3 vector, a V5m3-400 vector, a G9 vector, and a BCL11A shmir vector.

In various embodiments, the present invention contemplates, in part, a population of hematopoietic cells comprising hematopoietic stem and progenitor cells (HSPCs) transduced with a retrovirus, wherein the population of hematopoietic cells comprises at least 85% HSPCs, wherein at least 50% of the HSPCs are transduced, wherein the HSPCs have an average vector copy number (VCN) of about 0.5 to about 5.0, wherein viability of the population of cells is at least 75%, wherein endotoxin level of the population of hematopoietic cells is about 0.5 EU/mL to about 5.0 EU/mL, and wherein the population of hematopoietic cells comprises at least $1 \times 10^6$ HSPCs.

In various embodiments, the present invention contemplates, in part, a population of hematopoietic cells comprising $CD34^+CD38^{Lo}CD90^+CD45^{RA-}$ cells transduced with a retrovirus, wherein at least 50% of the $CD34^+CD^{Lo}CD90^+CD45^{RA-}$ cells are transduced, wherein the $CD34^+CD38^{Lo}CD90^+CD45^{RA-}$ cells have an average VCN of about 0.5 to about 5.0, wherein viability of the population of hematopoietic cells is at least 75%, wherein endotoxin level of the population of hematopoietic cells is about 0.5 EU/mL to about 5.0 EU/mL, and wherein the population of hematopoietic cells comprises at least $1 \times 10^6$ $CD34^+$ cells.

In various embodiments, the present invention contemplates, in part, a population of hematopoietic cells comprising $CD34^+$ cells transduced with a retrovirus, wherein at least 50% of the $CD34^+$ are transduced, wherein the $CD34^+$ cells have an average vector copy number (VCN) of about 0.5 to about 5.0, wherein viability of the population of hematopoietic cells is at least 75%, wherein endotoxin level of the population of hematopoietic cells is about 0.5 EU/mL to about 5.0 EU/mL, and wherein the population comprises at least $2 \times 10^6$ $CD34^+$ cells.

In particular embodiments, the retroviral vector is a lentiviral vector.

In particular embodiments, the lentiviral vector transduces the HSPCs or $CD34^+$ cells at a multiplicity of infection (MOI) of about 10 to about 30.

In particular embodiments, the lentiviral vector transduces the HSPCs or $CD34^+$ cells at a multiplicity of infection (MOI) of about 10 to about 25.

In particular embodiments, the lentiviral vector transduces the HSPCs or $CD34^+$ cells at a multiplicity of infection (MOI) of about 10 to about 20.

In some embodiments, the MOI is about 10, about 11, about 12, about 13, about 14, about 15, about 16, about 17, about 18, about 19, about 20, about 21, about 22, about 23, about 24, about 25, about 26, about 27, about 28, about 29 or about 30.

In certain embodiments, at least 75% of the cells have been transduced.

In additional embodiments, at least 90% of the cells have been transduced.

In particular embodiments, the average VCN is at least 1.0.

In particular embodiments, the average VCN is at least 1.5.

In particular embodiments, the average VCN is at least 2.0.

In particular embodiments, the average VCN is at least 2.5.

In some embodiments, viability of the population of cells is at least 85%.

In certain embodiments, viability of the population of cells is at least 95%.

In further embodiments, the endotoxin level of the population of hematopoietic cells is at most 5.0 EU/mL.

In some embodiments, the endotoxin level of the population of hematopoietic cells is most 0.5 EU/mL.

In further embodiments, the population of cells comprises at least $1 \times 10^7$ HSPCs cells.

In additional embodiments, the population of cells comprises at least $1 \times 10^8$ HSPCs cells.

In certain embodiments, the population of cells comprises at least $1 \times 10^9$ HSPCs cells.

In certain embodiments, the source of the cells is umbilical cord blood, bone marrow, or mobilized peripheral blood.

In some embodiments, the source of the cells is mobilized peripheral blood.

In additional embodiments, the retroviral vector is derived from a lentivirus selected from the group consisting of: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, the retroviral vector is derived from an HIV lentivirus.

In additional embodiments, the retroviral vector is derived from an HIV-1 lentivirus.

In certain embodiments, the retroviral vector comprises: a) a 5' long terminal (LTR); b) an RNA export element; c) a lentiviral central polypurine tract (cPPT); d) a promoter operably linked to a gene of interest; and e) a SIN 3' LTR.

In some embodiments, the modified 5' LTR further comprises a deletion compared to the wild-type 5' LTR.

In particular embodiments, the promoter of the 5' LTR is replaced with a heterologous promoter selected from the group consisting of: a cytomegalovirus (CMV) promoter, a Rous Sarcoma Virus (RSV) promoter, or a Simian Virus 40 (SV40) promoter In further embodiments, the RNA export element comprises a hepatitis B virus post-transcriptional regulatory element (PRE) or a human immunodeficiency virus (HIV) rev response element (RRE).

In certain embodiments, the 3' LTR comprises a polyadenylation sequence.

In particular embodiments, the lentiviral vector encodes an ATP-binding cassette, sub-family D, member 1 (ABCD1) polypeptide.

In further embodiments, the lentiviral vector comprises a myeloproliferative sarcoma virus enhancer, negative control region deleted, d1587rev primer-binding site substituted (MND) promoter or transcriptionally active fragment thereof operably linked to a polynucleotide encoding an ATP-binding cassette, sub-family D, member 1 (ABCD1) polypeptide.

In certain embodiments, the lentiviral vector encodes adenosine deaminase.

In certain embodiments, the lentiviral vector comprises an elongation factor 1 alpha promoter operably linked to a polynucleotide encoding adenosine deaminase.

In certain embodiments, the lentiviral vector encodes interleukin 2 receptor gamma.

In certain embodiments, the lentiviral vector comprises an elongation factor 1 alpha promoter operably linked to a polynucleotide encoding interleukin 2 receptor gamma.

In particular embodiments, the lentiviral vector encodes tripeptidyl peptidase 1.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding tripeptidyl peptidase 1.

In particular embodiments, the lentiviral vector encodes alpha-L iduronidase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding alpha-L iduronidase.

In particular embodiments, the lentiviral vector encodes iduronate 2-sulfatase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding iduronate 2-sulfatase.

In certain embodiments, the promoter comprises one or more elements of a human β-globin LCR.

In some embodiments, the human β-globin LCR comprises DNase I hypersensitive site 2, 3, and 4 from the human β-globin LCR.

In particular embodiments, the lentiviral vector further comprises a human β-globin 3' enhancer element.

In additional embodiments, the gene of interest encodes an antisickling protein or a globin gene.

In particular embodiments, the gene of interest encodes a human β-globin protein, a human δ-globin protein, a human γ-globin protein, a human $\beta^{A-T87Q}$-globin protein, a human $\beta^{A-G16D/E22A/T87Q}$-globin protein, or a human $\beta^{A-T87Q/K95E/K120E}$-globin protein.

In particular embodiments, the lentiviral vector is an AnkT9W vector, a T9Ank2W vector, a TNS9 vector, a lentiglobin HPV569 vector, a lentiglobin BB305 vector, a BG-1 vector, a BGM-1 vector, a d432β$^A$γ vector, a mLARβΔγV5 vector, a GLOBE vector, a G-GLOBE vector, a βAS3-FB vector, a V5 vector, a V5m3 vector, a V5m3-400 vector, a G9 vector, and a BCL11A shmir vector.

In particular embodiments, the cells transduced with the vectors and compositions contemplated herein comprise the β-globin alleles: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In particular embodiments, the cells transduced with the vectors and compositions contemplated herein comprise the β-globin alleles: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In particular embodiments, the cells transduced with the vectors and compositions contemplated herein comprise the β-globin alleles: $\beta^E/\beta^S$, $\beta^0/\beta^S$, $\beta^C/\beta^S$, $\beta^+/\beta^S$ or $\beta^S/\beta^S$.

In various embodiments, the present invention contemplates, in part, a composition comprising the population of hematopoietic cells contemplated herein.

In various embodiments, the present invention contemplates, in part, a pharmaceutical composition comprising the population of hematopoietic cells contemplated herein and a pharmaceutically acceptable carrier.

In various embodiments, the present invention contemplates, in part, a composition comprising: a hematopoietic stem or progenitor cell; a retroviral vector or lentiviral vector; and a poloxamer having an average molecular weight of polypropylene subunits greater than about 2250 Daltons and comprising greater than about 40% polyethylene oxide, optionally wherein the poloxamer is selected from the group consisting of: poloxamer 288, poloxamer 335, poloxamer 338, and poloxamer 407.

In various embodiments, the present invention contemplates, in part, a culture comprising: a hematopoietic stem or progenitor cell; a culture medium; a retroviral vector; and a poloxamer having an average molecular weight of polypropylene subunits greater than about 2250 Daltons and comprising greater than about 40% polyethylene oxide.

In various embodiments, the present invention contemplates, in part, a culture comprising: a hematopoietic stem or progenitor cell; a culture medium; a retroviral vector; an agent that increases prostaglandin EP receptor signaling; and a poloxamer having an average molecular weight of polypropylene subunits greater than about 2250 Daltons and comprising greater than about 40% polyethylene oxide.

In particular embodiments, the poloxamer has an average molecular weight of polypropylene subunits of at least about 2750 Daltons.

In particular embodiments, the poloxamer has an average molecular weight of polypropylene subunits of at least about 3250 Daltons.

In particular embodiments, the poloxamer has an average molecular weight of polypropylene subunits of at least about 4000 Daltons.

In particular embodiments, the poloxamer comprises at least about 50% polyethylene oxide.

In particular embodiments, the poloxamer comprises at least about 60% polyethylene oxide.

In particular embodiments, the poloxamer comprises at least about 70% polyethylene oxide.

In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide.

In particular embodiments, the poloxamer has an average molecular weight of polypropylene subunits of at least about 2750 Daltons and the poloxamer comprises at least about 50% polyethylene oxide.

In particular embodiments, the poloxamer has an average molecular weight of polypropylene subunits of at least about 3250 Daltons and the poloxamer comprises at least about 50% polyethylene oxide.

In various embodiments, the present invention contemplates, in part, a culture comprising: a hematopoietic stem or progenitor cell; a culture medium; a retroviral vector; an agent that increases prostaglandin EP receptor signaling; and a poloxamer having a molecular weight of at least 10,000 Daltons.

In various embodiments, the present invention contemplates, in part, a culture comprising: a CD34$^+$ hematopoietic stem or progenitor cell; a culture medium; a lentiviral vector; and poloxamer 338.

In various embodiments, the present invention contemplates, in part, a culture comprising: a CD34$^+$ hematopoietic stem or progenitor cell; a culture medium; a lentiviral vector; an agent that increases prostaglandin EP receptor signaling; and poloxamer 338.

In various embodiments, the present invention contemplates, in part, a culture comprising: a CD34$^+$ hematopoietic stem or progenitor cell; a culture medium; a lentiviral vector; and poloxamer 407.

In various embodiments, the present invention contemplates, in part, a culture comprising: a CD34+ hematopoietic stem or progenitor cell; a culture medium; a lentiviral vector; an agent that increases prostaglandin EP receptor signaling; and poloxamer 407.

In certain embodiments, the agent that increases prostaglandin EP receptor signaling is selected from the group consisting of: $PGA_2$; $PGB_2$; $PGD_2$; $PGE_1$; $PGE_2$; $PGF_2$; $PGI_2$; $PGH_2$; $PGJ_2$; and derivatives and analogues thereof In particular embodiments, the agent that increases prostaglandin EP receptor signaling is selected from the group consisting of: 15d-$PGJ_2$; delta12-$PGJ_2$; 2-hydroxyheptadecatrienoic acid (HHT); Thromboxane A2; Thromboxane B2; Iloprost; Treprostinil; Travoprost; Carboprost tromethamine; Tafluprost; Latanoprost; Bimatoprost; Unoprostone isopropyl; Cloprostenol; Oestrophan; Superphan; Misoprostol; Butaprost; Linoleic Acid; 13(s)-HODE; LY171883; Mead Acid; Eicosatrienoic Acid; Epoxyeicosatrienoic Acid; ONO-259; Cay 1039; a PGE2 receptor agonist; 16,16-dimethyl $PGE_2$; 19(R)-hydroxy $PGE_2$; 16,16-dimethyl $PGE_2$ p-(p-acetamidobenzamido) phenyl ester; 11-deoxy-16,16-dimethyl $PGE_2$; 9-deoxy-9-methylene-16,16-dimethyl $PGE_2$; 9-deoxy-9-methylene $PGE_2$; Sulprostone; $PGE_2$ serinol amide; $PGE_2$ methyl ester; 16-phenyl tetranor $PGE_2$; 15(S)-15-methyl $PGE_2$; and 15(R)-15-methyl $PGE_2$.

In additional embodiments, the agent that increases prostaglandin EP receptor signaling is selected from the group consisting of: prostaglandin $E_2$ ($PGE_2$), or 16,16-dimethyl $PGE_2$.

In particular embodiments, the agent that increases prostaglandin EP receptor signaling is $PGE_2$.

In particular embodiments, the hematopoietic stem or progenitor cells are CD34+ cells or CD133+ cells.

In certain embodiments, the hematopoietic stem or progenitor cells are transduced in the presence of a poloxamer selected from the group consisting of: poloxamer 288, poloxamer 335, poloxamer 338, and poloxamer 407.

In particular embodiments, the hematopoietic stem or progenitor cells are transduced in the presence of poloxamer 288.

In some embodiments, the hematopoietic stem or progenitor cells are transduced in the presence of poloxamer 335.

In additional embodiments, the hematopoietic stem or progenitor cells are transduced in the presence of poloxamer 338.

In further embodiments, the hematopoietic stem or progenitor cells are transduced in the presence of poloxamer 407.

In some embodiments, the hematopoietic stem or progenitor cells are transduced in the presence of a polycationic polymer.

In additional embodiments, the polycationic polymer is polybrene, protamine sulfate, polyethylenimine, or a polyethylene glycol/poly-L-lysine block copolymer.

In some embodiments, the retroviral vector is a lentiviral vector.

In some embodiments, the retroviral vector is derived from a lentivirus selected from the group consisting of: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (Hy); bovine immune deficiency virus (BIV); and simian immunodeficiency virus (SIV).

In certain embodiments, the retroviral vector is derived from an HIV lentivirus.

In particular embodiments, the retroviral vector is derived from an HIV-1 lentivirus.

In particular embodiments, the lentiviral vector is present at an MOI of about 10 to about 30.

In particular embodiments, the lentiviral vector is present at an MOI of about 10 to about 25.

In particular embodiments, the lentiviral vector is present at an MOI of about 10 to about 20.

In some embodiments, the lentiviral vector is present at an MOI of about 10, about 11, about 12, about 13, about 14, about 15, about 16, about 17, about 18, about 19, about 20, about 21, about 22, about 23, about 24, about 25, about 26, about 27, about 28, about 29 or about 30.

In particular embodiments, the lentiviral vector encodes an ATP-binding cassette, sub-family D, member 1 (ABCD1) polypeptide.

In further embodiments, the lentiviral vector comprises a myeloproliferative sarcoma virus enhancer, negative control region deleted, d1587rev primer-binding site substituted (MND) promoter or transcriptionally active fragment thereof operably linked to a polynucleotide encoding an ATP-binding cassette, sub-family D, member 1 (ABCD1) polypeptide.

In certain embodiments, the lentiviral vector encodes adenosine deaminase.

In certain embodiments, the lentiviral vector comprises an elongation factor 1 alpha promoter operably linked to a polynucleotide encoding adenosine deaminase.

In certain embodiments, the lentiviral vector encodes interleukin 2 receptor gamma.

In certain embodiments, the lentiviral vector comprises an elongation factor 1 alpha promoter operably linked to a polynucleotide encoding interleukin 2 receptor gamma.

In particular embodiments, the lentiviral vector encodes tripeptidyl peptidase 1.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding tripeptidyl peptidase 1.

In particular embodiments, the lentiviral vector encodes alpha-L iduronidase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding alpha-L iduronidase.

In particular embodiments, the lentiviral vector encodes iduronate 2-sulfatase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding iduronate 2-sulfatase.

In certain embodiments, the lentiviral vector comprises a promoter comprising one or more elements of a human β-globin LCR.

In some embodiments, the human β-globin LCR comprises DNase I hypersensitive site 2, 3, and 4 from the human β-globin LCR.

In particular embodiments, the lentiviral vector further comprises a human β-globin 3' enhancer element.

In additional embodiments, the gene of interest encodes an anti-sickling protein or a globin gene.

In particular embodiments, the gene of interest encodes a human β-globin protein, a human δ-globin protein, a human γ-globin protein, a human βA-T87Q-globin protein, a human βA-G16D/E22A/T87Q-globin protein, or a human βA-T87Q/K95E/K120E-globin protein.

In particular embodiments, the lentiviral vector is an AnkT9W vector, a T9Ank2W vector, a TNS9 vector, a lentiglobin HPV569 vector, a lentiglobin BB305 vector, a BG-1 vector, a BGM-1 vector, a d432βAγ vector, a mLAβAγV5 vector, a GLOBE vector, a G-GLOBE vector, a βAS3-FB vector, a V5 vector, a V5m3 vector, a V5m3-400 vector, a G9 vector, and a BCL11A shmir vector.

In various embodiments, the present invention contemplates, in part, a culture comprising: a hematopoietic stem or progenitor cell; a culture medium; staurosporine; a retroviral vector; and a poloxamer having a molecular weight of at least 10,000 Daltons, optionally, wherein the cells are contacted with staurosporine prior to contact with the retroviral vector and poloxamer.

In various embodiments, the present invention contemplates, in part, a culture comprising: a hematopoietic stem or progenitor cell; a culture medium; staurosporine; a retroviral vector; and a poloxamer having an average molecular weight of polypropylene subunits greater than about 2250 Daltons and comprising greater than about 40% polyethylene oxide.

In some embodiments, the hematopoietic stem or progenitor cells are $CD34^+$ cells or $CD133^+$ cells.

In particular embodiments, the poloxamer comprises at least about 50% polyethylene oxide.

In particular embodiments, the poloxamer comprises at least about 60% polyethylene oxide.

In particular embodiments, the poloxamer comprises at least about 70% polyethylene oxide.

In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide.

In particular embodiments, the poloxamer has an average molecular weight of polypropylene subunits of at least about 2750 Daltons and the poloxamer comprises at least about 50% polyethylene oxide.

In particular embodiments, the poloxamer has an average molecular weight of polypropylene subunits of at least about 3250 Daltons and the poloxamer comprises at least about 50% polyethylene oxide.

In particular embodiments, the hematopoietic stem or progenitor cells are transduced in the presence of a poloxamer selected from the group consisting of: poloxamer 288, poloxamer 335, poloxamer 338, and poloxamer 407.

In particular embodiments, the poloxamer is poloxamer 288.

In particular embodiments, the poloxamer is poloxamer 335.

In particular embodiments, the poloxamer is poloxamer 338.

In particular embodiments, the poloxamer is poloxamer 407.

In some embodiments, the hematopoietic stem or progenitor cells are transduced in the presence of a polycationic polymer.

In additional embodiments, the polycationic polymer is polybrene, protamine sulfate, polyethylenimine, or a polyethylene glycol/poly-L-lysine block copolymer.

In further embodiments, the retroviral vector is a lentiviral vector.

In additional embodiments, the retroviral vector is derived from a lentivirus selected from the group consisting of: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

In some embodiments, the retroviral vector is derived from an HIV lentivirus.

In particular embodiments, the retroviral vector is derived from an HIV-1 lentivirus.

In particular embodiments, the lentiviral vector is present at an MOI of about 10 to about 30.

In particular embodiments, the lentiviral vector is present at an MOI of about 10 to about 25.

In particular embodiments, the lentiviral vector is present at an MOI of about 10 to about 20.

In some embodiments, the lentiviral vector is present at an MOI of about 10, about 11, about 12, about 13, about 14, about 15, about 16, about 17, about 18, about 19, about 20, about 21, about 22, about 23, about 24, about 25, about 26, about 27, about 28, about 29 or about 30.

In particular embodiments, the lentiviral vector encodes an ATP-binding cassette, sub-family D, member 1 (ABCD1) polypeptide.

In further embodiments, the lentiviral vector comprises a myeloproliferative sarcoma virus enhancer, negative control region deleted, d1587rev primer-binding site substituted (MND) promoter or transcriptionally active fragment thereof operably linked to a polynucleotide encoding an ATP-binding cassette, sub-family D, member 1 (ABCD1) polypeptide.

In certain embodiments, the lentiviral vector encodes adenosine deaminase.

In certain embodiments, the lentiviral vector comprises an elongation factor 1 alpha promoter operably linked to a polynucleotide encoding adenosine deaminase.

In certain embodiments, the lentiviral vector encodes interleukin 2 receptor gamma.

In certain embodiments, the lentiviral vector comprises an elongation factor 1 alpha promoter operably linked to a polynucleotide encoding interleukin 2 receptor gamma.

In particular embodiments, the lentiviral vector encodes tripeptidyl peptidase 1.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding tripeptidyl peptidase 1.

In particular embodiments, the lentiviral vector encodes alpha-L iduronidase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding alpha-L iduronidase.

In particular embodiments, the lentiviral vector encodes iduronate 2-sulfatase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding iduronate 2-sulfatase.

In certain embodiments, the lentiviral vector comprises a promoter comprising one or more elements of a human β-globin LCR.

In some embodiments, the human β-globin LCR comprises DNase I hypersensitive site 2, 3, and 4 from the human β-globin LCR.

In particular embodiments, the lentiviral vector further comprises a human β-globin 3' enhancer element.

In additional embodiments, the gene of interest encodes an anti-sickling protein or a globin gene.

In particular embodiments, the gene of interest encodes a human β-globin protein, a human δ-globin protein, a human γ-globin protein, a human βA-T87Q-globin protein, a human βA-G16D/E22A/T87Q-globin protein, or a human βA-T87Q/K95E/K120E-globin protein.

In particular embodiments, the lentiviral vector is an AnkT9W vector, a T9Ank2W vector, a TNS9 vector, a lentiglobin HPV569 vector, a lentiglobin BB305 vector, a BG-1 vector, a BGM-1 vector, a d432βAγ vector, a mLARβAγV5 vector, a GLOBE vector, a G-GLOBE vector, a βAS3-FB vector, a V5 vector, a V5m3 vector, a V5m3-400 vector, a G9 vector, and a BCL11A shmir vector.

In various embodiments, the present invention contemplates, in part, a method of transducing a population of hematopoietic cells comprising culturing the cells in a culture medium, in the presence of a lentivirus, and poloxamer 338, optionally, wherein the cells are contacted with staurosporine, if present, prior to contact with the retroviral vector and poloxamer.

In various embodiments, the present invention contemplates, in part, a method of transducing a population of hematopoietic cells comprising culturing the cells in a culture medium, in the presence of a lentivirus, an agent that increases prostaglandin EP receptor signaling or staurosporine, and a poloxamer having a molecular weight of at least 10,000 Daltons, optionally, wherein the cells are contacted with staurosporine, if present, prior to contact with the retroviral vector and poloxamer.

In various embodiments, the present invention contemplates, in part, a method of transducing a population of hematopoietic cells comprising culturing the cells in a culture medium, in the presence of a lentivirus, and poloxamer 407, optionally, wherein the cells are contacted with staurosporine, if present, prior to contact with the retroviral vector and poloxamer.

In various embodiments, the present invention contemplates, in part, a method of transducing a population of hematopoietic cells comprising culturing the cells in a culture medium, in the presence of a lentivirus, an agent that increases prostaglandin EP receptor signaling or staurosporine, and a poloxamer having an average molecular weight of polypropylene subunits greater than about 2250 Daltons and comprising greater than about 40% polyethylene oxide, optionally, wherein the cells are contacted with staurosporine, if present, prior to contact with the retroviral vector and poloxamer.

In certain embodiments, the agent that increases prostaglandin EP receptor signaling is selected from the group consisting of: $PGA_2$; $PGB_2$; $PGD_2$; $PGE_1$; $PGE_2$; $PGF_2$; $PGI_2$; $PGH_2$; $PGJ_2$; and derivatives and analogues thereof.

In further embodiments, the agent that increases prostaglandin EP receptor signaling is selected from the group consisting of: 15d-$PGJ_2$; delta12-$PGJ_2$; 2-hydroxyheptadecatrienoic acid (HHT); Thromboxane A2; Thromboxane B2; Iloprost; Treprostinil; Travoprost; Carboprost tromethamine; Tafluprost; Latanoprost; Bimatoprost; Unoprostone isopropyl; Cloprostenol; Oestrophan; Superphan; Misoprostol; Butaprost; Linoleic Acid; 13(s)-HODE; LY171883; Mead Acid; Eicosatrienoic Acid; Epoxyeicosatrienoic Acid; ONO-259; Cay 1039; a $PGE_2$ receptor agonist; 16,16-dimethyl $PGE_2$; 19(R)-hydroxy $PGE_2$; 16,16-dimethyl $PGE_2$ p-(p-acetamidobenzamido) phenyl ester; 11-deoxy-16,16-dimethyl $PGE_2$; 9-deoxy-9-methylene-16,16-dimethyl $PGE_2$; 9-deoxy-9-methylene $PGE_2$; Sulprostone; $PGE_2$ serinol amide; $PGE_2$ methyl ester; 16-phenyl tetranor $PGE_2$; 15(S)-15-methyl PGE2; and 15(R)-15-methyl $PGE_2$.

In particular embodiments, the agent that increases prostaglandin EP receptor signaling is selected from the group consisting of: prostaglandin $E_2$ ($PGE_2$), or 16,16-dimethyl $PGE_2$.

In particular embodiments, the agent that increases prostaglandin EP receptor signaling is $PGE_2$.

In particular embodiments, the poloxamer comprises at least about 50% polyethylene oxide.

In particular embodiments, the poloxamer comprises at least about 60% polyethylene oxide.

In particular embodiments, the poloxamer comprises at least about 70% polyethylene oxide.

In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide.

In particular embodiments, the poloxamer has an average molecular weight of polypropylene subunits of at least about 2750 Daltons and the poloxamer comprises at least about 50% polyethylene oxide.

In particular embodiments, the poloxamer has an average molecular weight of polypropylene subunits of at least about 3250 Daltons and the poloxamer comprises at least about 50% polyethylene oxide.

In some embodiments, the population of hematopoietic cells is transduced in the presence of a poloxamer selected from the group consisting of: poloxamer 288, poloxamer 335, poloxamer 338, and poloxamer 407.

In particular embodiments, the poloxamer is poloxamer 288.

In particular embodiments, the poloxamer is poloxamer 335.

In particular embodiments, the poloxamer is poloxamer 338.

In particular embodiments, the poloxamer is poloxamer 407.

In some embodiments, the population of hematopoietic cells is transduced in the presence of a polycationic polymer.

In particular embodiments, the polycationic polymer is polybrene, protamine sulfate, polyethylenimine or a polyethylene glycol/poly-L-lysine block copolymer.

In further embodiments, the lentiviral vector is derived from a lentivirus selected from the group consisting of: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, the lentiviral vector is derived from an HIV lentivirus.

In particular embodiments, the lentiviral vector is derived from an HIV-1 lentivirus.

In additional embodiments, the retroviral vector is a lentiviral vector that comprises: a) a 5' long terminal (LTR); b) a Psi (Ψ) packaging signal; c) an RNA export element; d) a lentiviral central polypurine tract (cPPT); e) a promoter operably linked to a polynucleotide of interest; and f) a SIN 3' LTR.

In certain embodiments, the modified 5' LTR further comprises a deletion compared to the wild-type 5' LTR.

In some embodiments, the promoter of the 5' LTR is replaced with a heterologous promoter selected from the group consisting of: a cytomegalovirus (CMV) promoter, a Rous Sarcoma Virus (RSV) promoter, or a Simian Virus 40 (SV40) promoter In some embodiments, the RNA export element comprises a hepatitis B virus post-transcriptional regulatory element (PRE) or a human immunodeficiency virus (HIV) rev response element (RRE).

In certain embodiments, the 3' LTR comprises a polyadenylation sequence.

In particular embodiments, the lentiviral vector is present at an MOI of about 10 to about 30.

In particular embodiments, the lentiviral vector is present at an MOI of about 10 to about 25.

In particular embodiments, the lentiviral vector is present at an MOI of about 10 to about 20.

In some embodiments, the lentiviral vector is present at an MOI of about 10, about 11, about 12, about 13, about 14, about 15, about 16, about 17, about 18, about 19, about 20, about 21, about 22, about 23, about 24, about 25, about 26, about 27, about 28, about 29 or about 30.

In particular embodiments, the lentiviral vector encodes an ATP-binding cassette, sub-family D, member 1 (ABCD1) polypeptide.

In further embodiments, the lentiviral vector comprises a myeloproliferative sarcoma virus enhancer, negative control region deleted, d1587rev primer-binding site substituted (MND) promoter or transcriptionally active fragment thereof operably linked to a polynucleotide encoding an ATP-binding cassette, sub-family D, member 1 (ABCD1) polypeptide.

In certain embodiments, the lentiviral vector encodes adenosine deaminase.

In certain embodiments, the lentiviral vector comprises an elongation factor 1 alpha promoter operably linked to a polynucleotide encoding adenosine deaminase.

In certain embodiments, the lentiviral vector encodes interleukin 2 receptor gamma.

In certain embodiments, the lentiviral vector comprises an elongation factor 1 alpha promoter operably linked to a polynucleotide encoding interleukin 2 receptor gamma.

In particular embodiments, the lentiviral vector encodes tripeptidyl peptidase 1.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding tripeptidyl peptidase 1.

In particular embodiments, the lentiviral vector encodes alpha-L iduronidase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding alpha-L iduronidase.

In particular embodiments, the lentiviral vector encodes iduronate 2-sulfatase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding iduronate 2-sulfatase.

In certain embodiments, the lentiviral vector comprises a promoter comprising one or more elements of a human β-globin LCR.

In some embodiments, the human β-globin LCR comprises DNase I hypersensitive site 2, 3, and 4 from the human β-globin LCR.

In particular embodiments, the lentiviral vector further comprises a human β-globin 3' enhancer element.

In additional embodiments, the gene of interest encodes an anti-sickling protein or a globin gene.

In particular embodiments, the gene of interest encodes a human β-globin protein, a human δ-globin protein, a human γ-globin protein, a human βA-T87Q-globin protein, a human βA-G16D/E22A/T87Q-globin protein, or a human βA-T87Q/K95E/K120E-globin protein.

In particular embodiments, the lentiviral vector is an AnkT9W vector, a T9Ank2W vector, a TNS9 vector, a lentiglobin HPV569 vector, a lentiglobin BB305 vector, a BG-1 vector, a BGM-1 vector, a d432βAγ vector, a mLARβAγV5 vector, a GLOBE vector, a G-GLOBE vector, a βAS3-FB vector, a V5 vector, a V5m3 vector, a V5m3-400 vector, a G9 vector, and a BCL11A shmir vector.

In some embodiments, the population of hematopoietic cells is transduced at least about 2 hours.

In certain embodiments, the population of hematopoietic cells is transduced at least about 24 hours.

In some embodiments, the population of hematopoietic cells is transduced from about 2 hours to about 24 hours.

In additional embodiments, the hematopoietic cells comprise hematopoietic stem or progenitor cells.

In particular embodiments, the hematopoietic cells comprise $CD34^+$ cells or $CD133^+$ cells.

In some embodiments, the population of hematopoietic cells is selected for $CD34^+$ or $CD133^+$ expression prior to transduction.

In various embodiments, the present invention contemplates, in part, a method of treating a hemoglobinopathy in a subject comprising administering the subject the population of cells contemplated herein.

In various embodiments, the present invention contemplates, in part, a method of ameliorating at least one symptom, of a hemoglobinopathy in a subject comprising administering the subject the population of cells contemplated herein, or a composition contemplated herein.

In particular embodiments, the β-globin alleles of the subject are $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In various embodiments, the present invention contemplates, in part, a method of treating a thalassemia in a subject comprising administering the subject an effective amount of the population of hematopoietic cells contemplated herein, or a composition contemplated herein.

In certain embodiments, the thalassemia is an α-thalassemia.

In additional embodiments, the thalassemia is a β-thalassemia.

In particular embodiments, the β-globin alleles of the subject are $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In various embodiments, the present invention contemplates, in part, a method of treating sickle cell disease in a subject comprising administering the subject an effective amount of the population of hematopoietic cells contemplated herein, or a composition contemplated herein.

In further embodiments, the β-globin alleles of the subject are $\beta^E/\beta^S$, $\beta^0/\beta^S$, $\beta^C/\beta^S$, $\beta^+/\beta^S$ or $\beta^S/\beta^S$.

In various embodiments, the present invention contemplates, in part, a method of treating a β-thalassemia in a subject comprising administering the subject an effective amount of the population of hematopoietic cells contemplated herein, or a composition contemplated herein.

In additional embodiments, the β-globin alleles of the subject are $\beta^E/\beta^0$, $\beta^C/\beta^0$, $\beta^0/\beta^0$, $\beta^C/\beta^C$, $\beta^E/\beta^E$, $\beta^E/\beta^1$, $\beta^C/\beta^E$, $\beta^C/\beta^1$, $\beta^0/\beta^1$, or $\beta^1/\beta^1$.

In various embodiments, the present invention contemplates, in part, a method of treating adrenoleukodystrophy or adrenomyeloneuropathy in a subject comprising administering the subject an amount of the population of hematopoietic cells contemplated herein, or a composition contemplated herein.

In particular embodiments, the present invention contemplates, in part, a method of treating ADA-SCID in a subject comprising administering the subject an effective amount of the population of hematopoietic cells contemplated herein, or a composition contemplated herein.

In certain embodiments, the present invention contemplates, in part, a method of treating X-SCID in a subject comprising administering the subject an effective amount of the population of hematopoietic cells contemplated herein, or a composition contemplated herein.

In some embodiments, the present invention contemplates, in part, a method of treating Batten's disease in a subject comprising administering the subject an effective amount of the population of hematopoietic cells contemplated herein, or a composition contemplated herein.

In further embodiments, the present invention contemplates, in part, a method of treating MPS I in a subject comprising administering the subject an effective amount of the population of hematopoietic cells contemplated herein, or a composition contemplated herein.

In additional embodiments, the present invention contemplates, in part, a method of treating MPS II in a subject comprising administering the subject an effective amount of the population of hematopoietic cells contemplated herein, or a composition contemplated herein.

In certain embodiments, the population of hematopoietic stem cells is administered an intravenous route, an intramedullary route, or an intraosseous route.

In particular embodiments, the population of hematopoietic stem cells is administered intravenously.

In various embodiments, the present invention contemplates, in part, a kit comprising an agent that increases prostaglandin EP receptor signaling or staurosporine, and a poloxamer.

In various embodiments, the present invention contemplates, in part, a kit comprising an agent that increases prostaglandin EP receptor signaling or staurosporine, and a poloxamer having a molecular weight of at least 10,000 Daltons.

In various embodiments, the present invention contemplates, in part, a kit comprising an agent that increases prostaglandin EP receptor signaling or staurosporine, and a poloxamer having an average molecular weight of polypropylene subunits greater than about 2250 Daltons and comprising greater than about 40% polyethylene oxide.

In particular embodiments, the poloxamer has an average molecular weight of polypropylene subunits of at least about 2250 Daltons.

In particular embodiments, the poloxamer has an average molecular weight of polypropylene subunits of at least about 2750 Daltons.

In particular embodiments, the poloxamer has an average molecular weight of polypropylene subunits of at least about 3250 Daltons.

In particular embodiments, the poloxamer has an average molecular weight of polypropylene subunits of at least about 4000 Daltons.

In certain embodiments, the poloxamer comprising at least about 40% polyethylene oxide.

In particular embodiments, the poloxamer comprises at least about 50% polyethylene oxide.

In particular embodiments, the poloxamer comprises at least about 60% polyethylene oxide.

In particular embodiments, the poloxamer comprises at least about 70% polyethylene oxide.

In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide.

In particular embodiments, the poloxamer has an average molecular weight of polypropylene subunits of at least about 2750 Daltons and the poloxamer comprises at least about 50% polyethylene oxide.

In particular embodiments, the poloxamer has an average molecular weight of polypropylene subunits of at least about 3250 Daltons and the poloxamer comprises at least about 50% polyethylene oxide.

In certain embodiments, the poloxamer is selected from the group consisting of: poloxamer 288, poloxamer 335, poloxamer 338, and poloxamer 407.

In particular embodiments, the poloxamer is poloxamer 288.

In some embodiments, the poloxamer is poloxamer 335.

In additional embodiments, the poloxamer is poloxamer 338.

In further embodiments, the poloxamer is poloxamer 407.

In various embodiments, the present invention contemplates, in part, a kit comprising an agent that increases prostaglandin EP receptor signaling and poloxamer 338.

In various embodiments, the present invention contemplates, in part, a kit comprising an agent that increases prostaglandin EP receptor signaling and poloxamer 407.

In further embodiments, the agent that increases prostaglandin EP receptor signaling is selected from the group consisting of: $PGA_2$; $PGB_2$; $PGD_2$; PGEi; $PGE_2$; $PGF_2$; $PGI_2$; $PGH_2$; $PGJ_2$; and derivatives and analogues thereof.

In additional embodiments, the agent that increases prostaglandin EP receptor signaling is selected from the group consisting of: 15d-$PGJ_2$; delta12-$PGJ_2$; 2-hydroxyheptadecatrienoic acid (HHT); Thromboxane A2; Thromboxane B2; Iloprost; Treprostinil; Travoprost; Carboprost tromethamine; Tafluprost; Latanoprost; Bimatoprost; Unoprostone isopropyl; Cloprostenol; Oestrophan; Superphan; Misoprostol; Butaprost; Linoleic Acid; 13(s)-HODE; LY171883; Mead Acid; Eicosatrienoic Acid; Epoxyeicosatrienoic Acid; ONO-259; Cay 1039; a $PGE_2$ receptor agonist; 16,16-dimethyl $PGE_2$; 19(R)-hydroxy $PGE_2$; 16,16-dimethyl $PGE_2$ p-(p-acetamidobenzamido) phenyl ester; 11-deoxy-16,16-dimethyl $PGE_2$; 9-deoxy-9-methylene-16,16-dimethyl $PGE_2$; 9-deoxy-9-methylene $PGE_2$; Sulprostone; $PGE_2$ serinol amide; $PGE_2$ methyl ester; 16-phenyl tetranor $PGE_2$; 15(S)-15-methyl PGE2; and 15(R)-15-methyl $PGE_2$.

In further embodiments, the agent that increases prostaglandin EP receptor signaling is selected from the group consisting of: prostaglandin $E_2$ ($PGE_2$), or 16,16-dimethyl $PGE_2$.

In certain embodiments, the agent that increases prostaglandin EP receptor signaling is $PGE_2$.

In certain embodiments, the kit further comprises a polycationic polymer.

In particular embodiments, the polycationic polymer is polybrene, protamine sulfate, polyethylenimine or a polyethylene glycol/poly-L-lysine block copolymer.

BRIEF DESCRIPTION OF SEVERAL VIEWS OF THE DRAWINGS

FIG. 1 shows in vivo analysis of $PGE_2$-treated hCD34+ cells. (A) Engraftment of hCD34+ cells measured by positive staining with anti-hCD45. (B) VCN analysis of engrafted human cells in mouse BM.

FIG. 11 shows the level of engraftment and differentiation capabilities of hCD34+ cells treated with $PGE_2$, F108, or a combination thereof at 2 months and 4 months post-transplant. (A) Neither F108, $PGE_2$, nor the combination affect engraftment levels of transduced hCD34+ cells in a xenotransplant setting. (B) Myeloid differentiation capability of engrafted cells is maintained. (C and D) Lymphoid differentiation capability of engrafted cells is maintained.

FIG. 15 also shows that transduction of hCD34+ cells in the presence of P105, F127, F108, or F98, and optionally $PGE_2$ did not impact cell growth.

Transduced colonies were pooled and analyzed for VCN. (PS=8 µg/mL protamine sulfate, $F108H_1/PGE_2$=1000 µg/mL F108 and 10 µM $PGE_2$). F108 and $PGE_2$ increased VCN in all cell lots.

Figure 24:
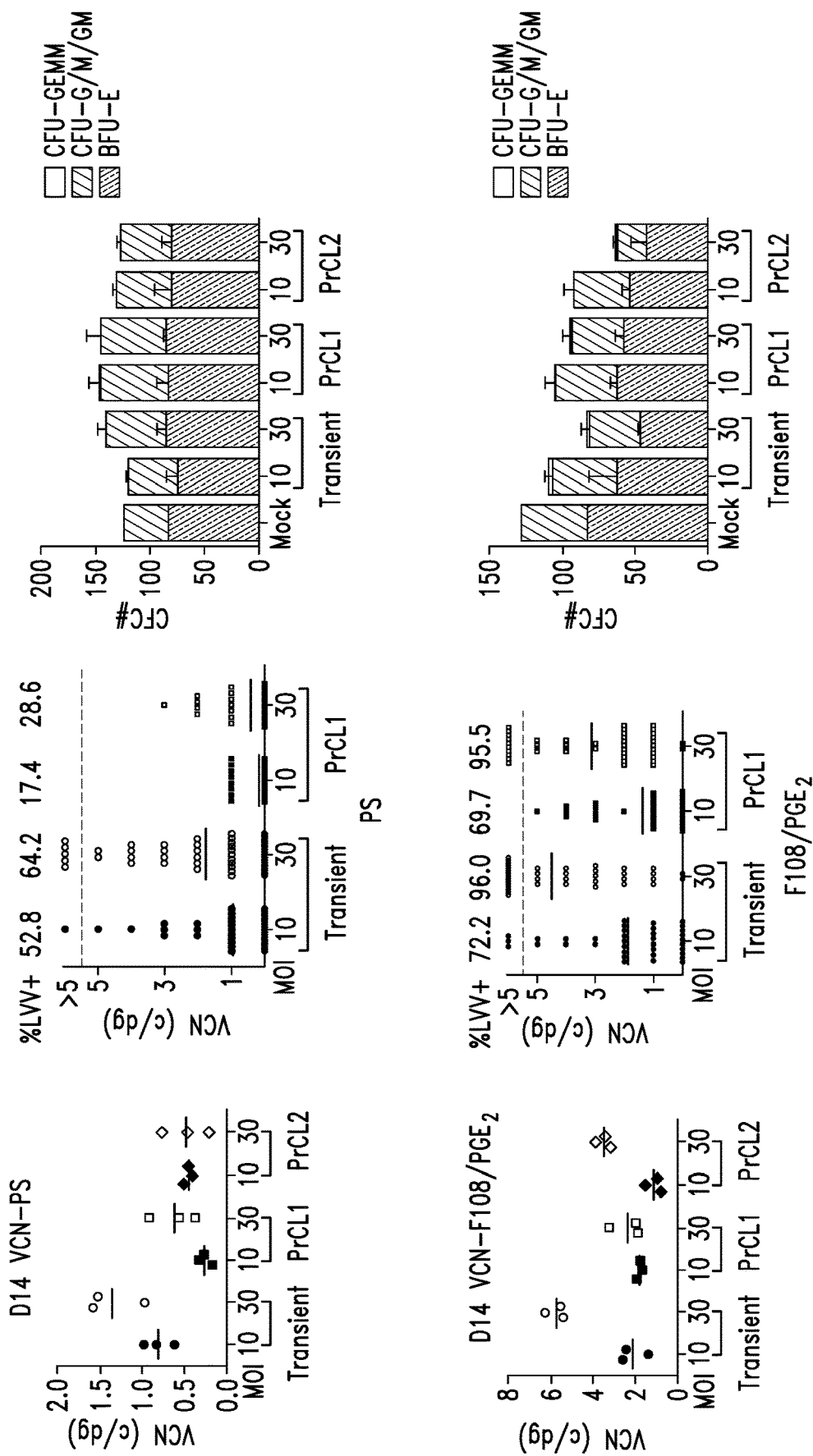
Figure 26E:
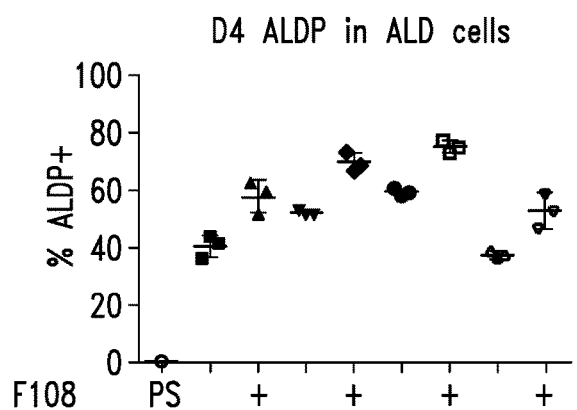
Figure 26F:
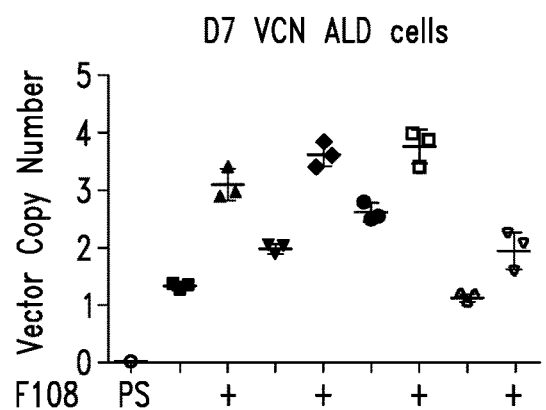
Figure 26G:
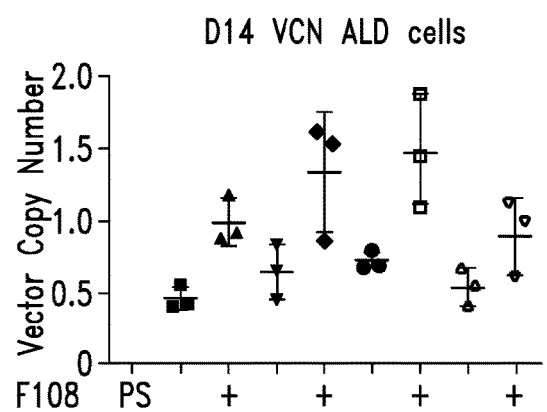
Figure 26H:
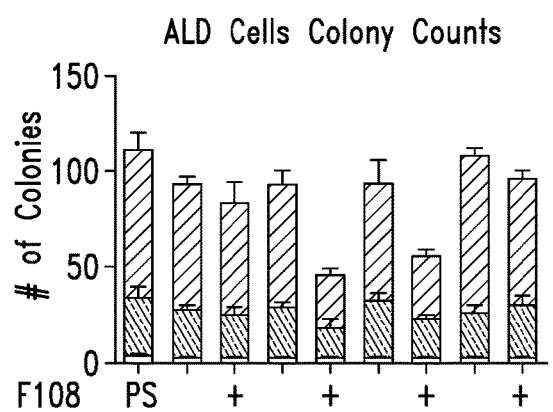
Figure 26I:
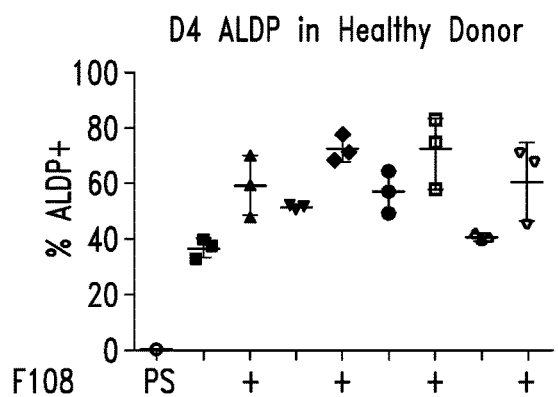
Figure 26J:
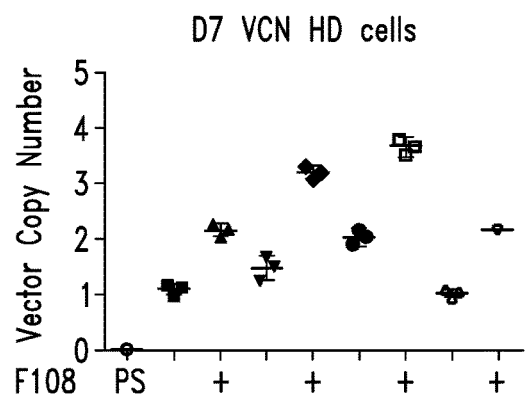
Figure 26K:
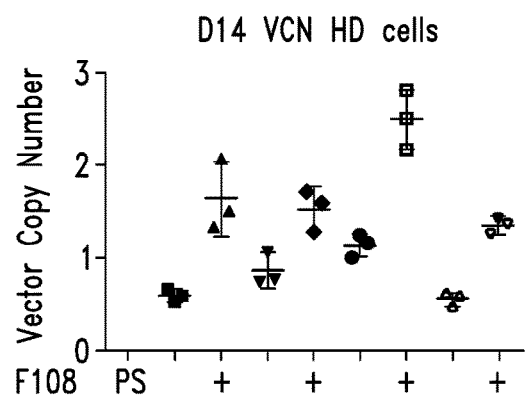
Figure 26L:
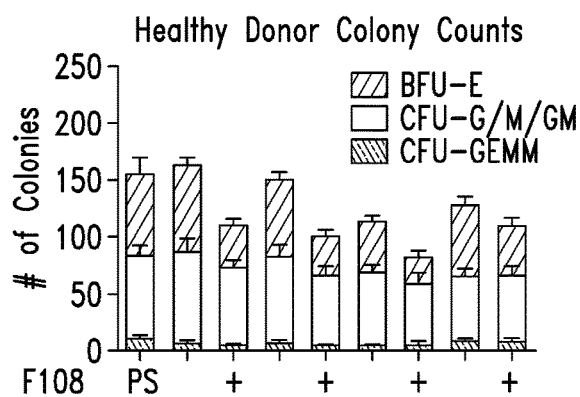

FIG. 24 shows human CD34+ cells transduced with a lentiviral vector encoding IL2Rγ and either protamine sulfate (top row) or F108 and $PGE_2$ (bottom row), where the lentiviral vector was produced by transient transfection or by producer cell clones (PrCL1, PrCL2). D14 VCNs from pooled methylcellulose colonies are shown in left most panels; individual colony VCN from plucked colonies and % LVV+ colonies are shown in the center panels; and colony enumeration is shown in the right most panels.

FIG. 25 shows that F108 and $PGE_2$ increase transduction with lentiviral vectors encoding tripeptidyl peptidase 1 (TPP1). Human CD34$^+$ cells were transduced with LVVs encoding either EF1α-TPP1 or MND-TPP1 at an MOI of 5 or 15 with and without F108 and $PGE_2$. Day 14 pooled methylcellulose colony VCNs are shown in upper left panel. TPP-1 enzyme activity from day 7 cytokine cultures are shown in upper middle panel (cell pellet) and upper right panel (cell supernatant). Mouse Lineage negative (Lin-) bone marrow cells were transduced with an MND-TPP1 LVV at an MOI of 5, 15, or 30 with and without F108 and $PGE_2$. D7 liquid culture VCNs are shown in the lower left panel; individual colony VCN by qPCR is shown in the lower middle panel; and % LVV+ colonies are shown in the lower right panel.

FIG. 26 Human CD34+ cells from AMN patients (FIG. 26, panels A-D), ALD patients (FIG. 26, panels E-H), and healthy donors (HD; FIG. 26, panels I-L) were transduced with an MND-ABCD1 LVV and either protamine sulfate, F108, $PGE_2$, or F108 and $PGE_2$. ALDP protein expression is shown in panels A, E, and I; pooled colony VCN is shown in panels B, F, and J; individual colony VCN is shown in panels C, G, and K; and colony formation analysis is shown in panels D, H, and L.

Figure 27:
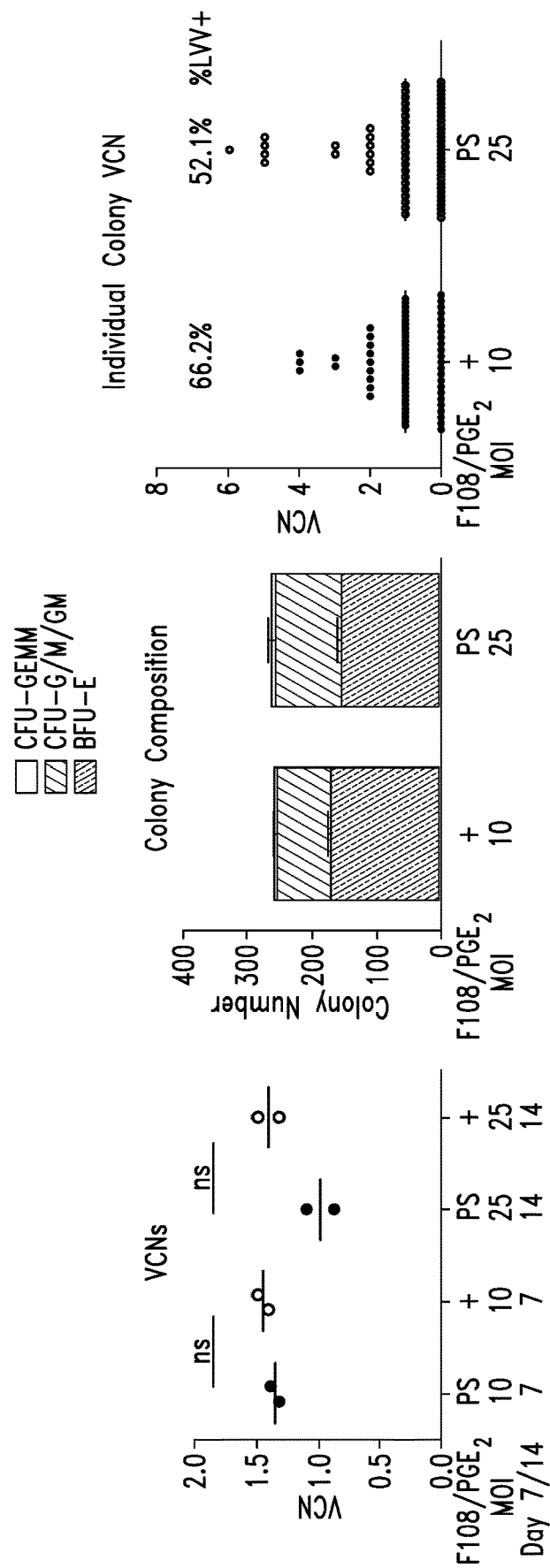

FIG. 27 shows pooled colony VCN (left panel), colony formation analysis (middle panel), and individual colony VCN and % LVV+ cells (right panel) from hCD34$^+$ cells transduced at MOIs of 10 or 25, with and without F108 and $PGE_2$.

DETAILED DESCRIPTION

A. Overview

Various illustrative embodiments of the invention contemplate gene therapies comprising hematopoietic stem and progenitor cell compositions with increased therapeutic efficacy and methods of making and using the same.

Gene therapy relies, in part, on sufficient expression of a therapeutic gene and corresponding protein. One of the factors that influences gene expression is copy number, or how many copies of the therapeutic gene are present in the cell. Viruses, such as retrovirus, e.g., lentivirus, adenovirus, and adeno-associated virus are often used gene therapy vectors to introduce the therapeutic gene into the cell; a process known as transduction. Inefficient viral transduction of hematopoietic stem and progenitor cells is one of the more important factors that limits the scope and applicability of gene therapies for many diseases and disorders that would benefit from genetically modified cells derived from the hematopoietic system. Poor viral transduction manifests as low vector copy number (VCN) and/or a low percentage of cells transduced. Thus, a significant problem with gene therapies that use viral vectors to deliver therapeutic transgenes to hematopoietic stem and progenitor cells is inefficient viral transduction, which may give rise to a subtherapeutic drug product. Inefficient transduction also leads to higher costs of goods, e.g., it increases the cost of lentivirus production because the more inefficient the transduction, the more lentivirus is needed.

The hematopoietic stem and progenitor cell-based gene therapies contemplated herein, and methods of making and using the same, solve these and other problems plaguing the art.

Particular exemplary embodiments contemplate a population of hematopoietic cells transduced with a retroviral vector, wherein the population of cells comprises an increased number or percentage of transduced hematopoietic stem and progenitor cells compared to populations of cells transduced with existing methods and compositions in the art. In another embodiment, a population of hematopoietic cells transduced with a retroviral vector comprises an increased VCN compared to the VCN of populations of cells transduced with existing methods and compositions in the art.

Other exemplary embodiments contemplate compositions, pharmaceutical compositions, and cell cultures comprising transduced hematopoietic cells.

Certain embodiments contemplate cell cultures comprising a population of hematopoietic cells, a retrovirus, and a poloxamer.

Certain embodiments contemplate cell cultures comprising a population of hematopoietic cells, a retrovirus, an agent that increases prostaglandin EP receptor signaling, and a poloxamer.

In particular embodiments, methods for transducing hematopoietic cells are contemplated comprising contacting a hematopoietic cell with a retrovirus and culturing the hematopoietic cell and the retrovirus in the presence a poloxamer.

In particular embodiments, methods for transducing hematopoietic cells are contemplated comprising contacting a hematopoietic cell with a retrovirus and culturing the hematopoietic cell and the retrovirus in the presence of an agent that increases prostaglandin EP receptor signaling, and a poloxamer.

In particular embodiments, methods for treating a subject having a monogenic disorder are contemplated comprising administering to the subject any of the hematopoietic cell-based gene therapies contemplated herein.

Various embodiments contemplated herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, DNA Cloning: A Practical Approach, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. As used herein, the terms "include" and "comprise" are used synonymously. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

"Transfection" refer to the process of introducing naked DNA into cells by non-viral methods.

"Infection" refers to the process of introducing foreign DNA into cells using a viral vector.

"Transduction" refers to the introduction of foreign DNA into a cell's genome using a viral vector.

"Vector copy number" or "VCN" refers to the number of copies of a vector, or portion thereof, in a cell's genome. The average VCN may be determined from a population of cells or from individual cell colonies. Exemplary methods for determining VCN include polymerase chain reaction (PCR) and flow cytometry.

"Transduction efficiency" refers to the percentage of cells transduced with at least one copy of a vector. For example if $1 \times 10^6$ cells are exposed to a virus and $0.5 \times 10^6$ cells are determined to have a least one copy of a virus in their genome, then the transduction efficiency is 50%. Exemplary methods for determining transduction efficiency include PCR and flow cytometry. In various embodiments, the phrases "number of lentiviral vector positive cells" or "percent lentiviral vector positive cells" is used indicate the transduction efficiency.

As used herein, the term "retrovirus" refers an RNA virus that reverse transcribes its genomic RNA into a linear double-stranded DNA copy and subsequently covalently integrates its genomic DNA into a host genome. Retroviruses are a common tool for gene delivery (Miller, 2000, Nature. 357: 455-460). Once the virus is integrated into the host genome, it is referred to as a "provirus." The provirus serves as a template for RNA polymerase II and directs the expression of RNA molecules encoded by the virus.

Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

Retroviral vectors, and more particularly, lentiviral vectors, may be used in practicing the present invention. Accordingly, the term "retrovirus" or "retroviral vector," as used herein is meant to include "lentivirus" and "lentiviral vectors" respectively.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a retroviral vector or plasmid containing structural and functional genetic elements, or portions thereof, including LTRs that are primarily derived from a lentivirus. The term "hybrid" refers to a vector, LTR or other nucleic acid containing both retroviral, e.g., lentiviral, sequences and non-lentiviral viral sequences. In one embodiment, a hybrid vector refers to a vector or transfer plasmid comprising retroviral, e.g., lentiviral, sequences for reverse transcription, replication, integration and/or packaging.

In particular embodiments, the terms "lentiviral vector" and "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. *J. of Virology*, Vol. 69, No. 4; pp. 2101-2109. Several retroviral vectors use the minimal packaging signal (also referred to as the psi [Ψ] or [Ψ+] sequence) needed for encapsidation of the viral genome. Thus, as used herein, the terms "packaging sequence," "packaging signal," "psi" and the symbol "Ψ," are used in reference to the non-coding sequence required for encapsidation of retroviral RNA strands during viral particle formation.

In various embodiments, vectors comprise modified 5' LTR and/or 3' LTRs. Modifications of the 3' LTR are often made to improve the safety of lentiviral or retroviral systems by rendering viruses replication-defective. The skilled artisan would be able to determine whether an LTR is modified by comparison to a reference LTR. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion and/or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the invention, the 3' LTR is modified such that the U5 region is replaced, for example, with a heterologous or synthetic poly(A) sequence, one or more insulator elements, and/or an inducible promoter. It should be noted that modifications to the LTRs such as modifications to the 3' LTR, the 5' LTR, or both 3' and 5' LTRs, are also included in the invention.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter may be inducible, such that transcription of all or part of the viral genome will occur only when one or more induction factors are present. Induction factors include, but are not limited to, one or more chemical compounds or physiological conditions, e.g., temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-1 or HIV-2. In some embodiments, the terms "FLAP element" and "cPPT/FLAP" are used interchangeably to refer to the foregoing FLAP element. Suitable FLAP elements are described in U.S. Pat. No. 6,682,907 and in Zennou, et al., 2000, *Cell,* 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. While not wishing to be bound by any theory, the DNA flap may act as a cis-active determinant of lentiviral genome nuclear import and/or may increase the titer of the virus. In particular embodiments, the retroviral or lentiviral vector backbones comprise one or more FLAP elements upstream or downstream of the heterologous genes of interest in the vectors. For example, in particular embodiments a vector includes a FLAP element. In one embodiment, a vector of the invention comprises a FLAP element isolated from HIV-1.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE). Generally, the RNA export element is placed within the 3' UTR of a gene, and can be inserted as one or multiple copies.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.,* 73:2886); the posttranscriptional regulatory element present in hepatitis B virus (HPRE) (Huang and Yen, 1995, *Mol. Cell. Biol.,* 5:3864); and the like (Liu et al., 1995, *Genes Dev.,* 9:1766). In particular embodiments, vectors of the invention lack or do not comprise a posttranscriptional regulatory element such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a WPRE or HPRE as an added safety measure.

In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments the poly(A) sequence is an SV40 polyA sequence, a bovine growth hormone polyA sequence (BGHpA), a rabbit β-globin polyA sequence (rβgpA), or another suitable heterologous or endogenous polyA sequence known in the art.

In certain embodiments, a retroviral or lentiviral vector further comprises one or more insulator elements. Insulators elements may contribute to protecting lentivirus-expressed sequences, e.g., therapeutic polypeptides, from integration site effects, which may be mediated by cis-acting elements present in genomic DNA and lead to deregulated expression of transferred sequences (i.e., position effect; see, e.g., Burgess-Beusse et al., 2002, *Proc. Natl. Acad. Sci., USA,* 99:16433; and Zhan et al., 2001, *Hum. Genet.,* 109:471). In some embodiments, transfer vectors comprise one or more insulator element the 3' LTR and upon integration of the provirus into the host genome, the provirus comprises the one or more insulators at the 5' LTR and/or 3' LTR, by virtue of duplicating the 3' LTR. Suitable insulators for use in the invention include, but are not limited to, the chicken β-globin insulator (see Chung et al., 1993. *Cell* 74:505; Chung et al., 1997. *PNAS* 94:575; and Bell et al., 1999. *Cell* 98:387, incorporated by reference herein). Examples of insulator elements include, but are not limited to, an insulator from a human β-globin locus, such as chicken HS4.

According to certain specific embodiments, most or all of the viral vector backbone sequences are derived from a lentivirus, e.g., HIV-1. However, it is to be understood that many different sources of lentiviral sequences can be used, and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid of the present invention.

As used herein, the term "agent" encompasses poloxamers, polycationic polymers, staurosporine, small organic molecules, prostaglandins, cAMP enhancers, Wnt pathway agonists, cAMP/PI3K/AKT pathway agonists, Ca2+ second messenger pathway agonists, nitric oxide (NO)/angiotensin signaling agonists and inorganic chemicals, including without limitation, all analogs and derivatives thereof.

A "small molecule," "small organic molecule," or "small molecule compound" refers to a low molecular weight compound that has a molecular weight of less than about 5 kD, less than about 4 kD, less than about 3 kD, less than about 2 kD, less than about 1 kD, or less than about 0.5 kD. In particular embodiments, small molecules can include, nucleic acids, peptides, peptidomimetics, peptoids, other small organic compounds or drugs, and the like. Libraries of chemical and/or biological mixtures, such as fungal, bacterial, or algal extracts, are known in the art and can be screened with any of the assays of the invention. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

In reference to agents, such as organic molecules, "analog" or "derivative" relates to a molecule that is similar to another chemical substance in structure and function, often differing structurally by a single element or group, but may differ by differ by modification of more than one group (e.g., 2, 3, or 4 groups) if it retains the same function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Derivatives may also include conjugates, such as biotin or avidin moieties, enzymes such as horseradish peroxidase and the like, and including radiolabeled, bioluminescent, chemoluminescent, or fluorescent moieties. Also, moieties may be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.) (see, e.g., WO/2006/047476 for exemplary EP agonist prodrugs, which is incorporated by reference for its disclosure of such agonists).

As used herein, the terms "polynucleotide" or "nucleic acid" refers to genomic DNA (gDNA), complementary DNA (cDNA) or DNA. Polynucleotides include single and double stranded polynucleotides, either recombinant, synthetic, or isolated. In some embodiments, polynucleotide refers to messenger RNA (mRNA), RNA, genomic RNA (gRNA), plus strand RNA (RNA(+)), minus strand RNA (RNA(−)). As used here, the terms "polyribonucleotide" or "ribonucleic acid" also refer to messenger RNA (mRNA), RNA, genomic RNA (gRNA), plus strand RNA (RNA(+)), minus strand RNA (RNA(−)) and inhibitory RNAs, including but not limited to, siRNA, shRNA, piRNA, miRNA or microRNA, and shRNAs embedded in a microRNA backbone (shmir). Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, viral vector and transfer plasmid polynucleotide sequences and compositions comprising the same are contemplated. In particular embodiments, polynucleotides encoding a therapeutic polypeptide including, but not limited to, a globin polypeptide, an antisickling globin polypeptide, an adenosine deaminase polypeptide, an interleukin 2 receptor gamma polypeptide, a tripeptidyl peptidase 1 polypeptide, an alpha-L iduronidase polypeptide, an iduronate 2-sulfatase polypeptide, or an ATP-binding cassette, sub-family D (ALD), member 1 (ABCD1) polypeptide, as discussed elsewhere herein are contemplated.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

As used herein, the term "isolated" means material, e.g., a polynucleotide, a polypeptide, a cell, that is substantially or essentially free from components that normally accompany it in its native state. In particular embodiments, the term "obtained" or "derived" is used synonymously with isolated. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. The terms "complementary" and "complementarity" refer to polynucleotides (i.e., a sequence of nucleotides) related by the base-pairing rules. For example, the complementary strand of the DNA sequence 5' AGTCATG 3' is 3' TCAGTAC 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise one, two, three, four, five or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

As used herein, the term "polynucleotide(s)-of-interest" refers to one or more polynucleotides, e.g., a polynucleotide encoding a polypeptide (i.e., a polypeptide-of-interest), inserted into an expression vector that is desired to be expressed. In preferred embodiments, vectors and/or plasmids comprise one or more polynucleotides-of-interest, e.g., a polynucleotide encoding a globin polypeptide, an antisickling globin polypeptide, an adenosine deaminase polypeptide, an interleukin 2 receptor gamma polypeptide, a tripeptidyl peptidase 1 polypeptide, an alpha-L iduronidase polypeptide, an iduronate 2-sulfatase polypeptide, or an ATP-binding cassette, sub-family D (ALD), member 1 (ABCD1) polypeptide. In certain embodiments, a polynucleotide-of-interest encodes a polypeptide that provides a therapeutic effect in the treatment, prevention, or amelioration of a hematopoietic disease or disorder, which may be referred to as a "therapeutic polypeptide," e.g., a globin gene. See, for example U.S. Pat. Nos. 6,051,402 and 7,901,671, the full disclosure and claims of which are specifically incorporated herein by reference.

In certain other embodiments, a polynucleotide-of-interest encodes a polypeptide that provides a therapeutic effect in the treatment, prevention, or amelioration of an adrenoleukodystrophy or adrenomyeloneuropathy, which may be referred to as a "therapeutic polypeptide," e.g., an ABCD1 gene. See, for example, U.S. Pat. Nos. 5,869,039; and 6,013,769, the full disclosure and claims of which are specifically incorporated herein by reference.

The term "globin" as used herein refers to proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are included by the term globin. The term excludes hemocyanins. Examples of globins include α-globin or variant thereof, β-globin or variant thereof, a γ-globin or a variant thereof, and δ-globin or a variant thereof.

In one embodiment, the polynucleotide-of-interest is a transgene that encodes a polypeptide that provides a therapeutic function for the treatment of a hemoglobinopathy, e.g., α-globin, γ-globin, β-globin or antisickling β-globin, e.g., β-globin$^{A-T87Q}$. Polynucleotides-of-interest, and polypeptides encoded therefrom, include both polynucleotides that encode wild-type polypeptides, as well as functional variants and fragments thereof. In particular embodiments, a functional variant has at least 80%, at least 90%, at least 95%, at least 96%, at least 97%, at least 98%, at least 99% identity to a corresponding wild-type reference polynucleotide or polypeptide sequence. In certain embodiments, a functional variant or fragment has at least 50%, at least 60%, at least 70%, at least 80%, at least 90%, at least a 100%, or at least 110% or more of a biological activity of a corresponding wild-type polypeptide. Representative polynucleotides sequences suitable for use in exemplary embodiments include, but are not limited to, polynucleotides encoding α-globin, β-globin, β-globin$^{A-T87Q}$, anti-sickling globins, γ-globin, and δ globin.

Polynucleotides, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

The term "expression control sequence" refers to a polynucleotide sequence that comprises one or more promoters, enhancers, or other transcriptional control elements or combinations thereof that are capable of directing, increasing, regulating, or controlling the transcription or expression of an operatively linked polynucleotide. In particular embodiments, vectors of the invention comprise one or more expression control sequences that are specific to particular cells, cell types, or cell lineages e.g., target cells; that is, expression of polynucleotides operatively linked to an expression control sequence specific to particular cells, cell types, or cell lineages is expressed in target cells and not in other non-target cells. Each one of the one or more expression control sequences in a vector that are cell specific may express in the same or different cell types depending on the therapy desired. In preferred embodiments, vectors comprise one or more expression control sequences specific to hematopoietic cells, e.g., hematopoietic stem or progenitor cells. In other preferred embodiments, vectors comprise one or more expression control sequences specific to hematopoietic and/or erythroid cells.

The term "promoter" as used herein refers to a recognition site of a polynucleotide (DNA or RNA) to which an RNA polymerase binds. The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

In particular embodiments, a vector comprises exogenous, endogenous, or heterologous control sequences such as promoters and/or enhancers. An "endogenous" control sequence is one which is naturally linked to a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular gene therapy.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer or other expression control sequence) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively. Illustrative ubiquitous expression control sequences include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., (2007) Nature Biotechnology 25, 1477-1482), a Ubiquitin C promoter (UBC), a phosphoglycerate kinase-1 (PGK) promoter, a cytomegalovirus enhancer/chicken β-actin (CAG) promoter, and a β-actin promoter.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

Illustrative examples of tissue specific promoters include, but are not limited to: an B29 promoter (B cell expression), a runt transcription factor (CBFa2) promoter (stem cell specific expression), an CD14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fms-related tyrosine kinase 1 (FLT1) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-β) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), a Wiskott-Aldrich syndrome protein (WASP) promoter (hematopoietic cell expression).

In one embodiment, a vector comprises one or more hematopoietic cell or tissue specific promoters and/or enhancers selected from the group consisting of: a human β-globin promoter; a human β-globin LCR; and a human α-globin HS40 enhancer and an ankyrin-1 promoter, operably linked to a polynucleotide encoding a globin polypeptide.

In another embodiment, a vector of the present invention comprises a promoter active in a microglial cell, operably linked to a polynucleotide encoding an ATP-binding cassette, sub-family D, member 1 (ABCD1) polypeptide. In certain embodiments, the promoter comprises a myeloproliferative sarcoma virus enhancer, negative control region deleted, d1587rev primer-binding site substituted (MND) promoter or transcriptionally active fragment thereof.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments of the invention provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., (2003) Gene, 323:67), the cumate inducible gene switch (WO 2002/088346), tetracycline-dependent regulatory systems, etc.

Conditional expression can also be achieved by using a site specific DNA recombinase. According to certain embodiments, a vector may comprise at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, (1993) Current Opinion in Biotechnology 3:699-707), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The vectors may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., (1994) Current Opinion in Biotechnology 5:521-527). Other exemplary loxP sites include, but are not limited to: 1ox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), F1, F2, F3 (Schlake and Bode, 1994), F4, F5 (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., (1990) Trends Biochem Sci 15(12):477-83) and Jackson and Kaminski. (1995) RNA 1(10):985-1000. In particular embodiments, a vector includes one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (Kozak, (1986) Cell. 44(2):283-92, and Kozak, (1987) Nucleic Acids Res. 15(20):8125-48). In particular embodiments, the vectors contemplated by the invention, comprise polynucleotides that have a consensus Kozak sequence and that encode a desired polypeptide.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., (1977) Cell 11:223-232) and adenine phosphoribosyltransferase (Lowy et al., (1990) Cell 22:817-823) genes which can be employed in tk- or aprt-cells, respectively.

In various embodiments, vectors are used to increase, establish and/or maintain the expression of one or more polypeptides. The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Illustrative examples of polypeptides include, but are not limited to globin polypeptides, suitable for use in the compositions and methods of particular embodiments. Also, see, e.g., U.S. Pat. Nos. 6,051,402; 7,901,671; and 9,068,199, the full disclosure and claims of which are specifically incorporated herein by reference in their entireties.

Illustrative examples of polypeptides also includes ABCD1 polypeptides. Also, see, e.g., U.S. Pat. Nos. 5,869,039; 6,013,769; 8,858,928; and 9,061,031, the full disclosure and claims of which are specifically incorporated herein by reference herein by reference in their entireties.

Further illustrative examples of polypeptides include but are not limited to a globin polypeptide, an antisickling globin polypeptide, an adenosine deaminase polypeptide, an interleukin 2 receptor gamma polypeptide, a tripeptidyl peptidase 1 polypeptide, an alpha-L iduronidase polypeptide, an iduronate 2-sulfatase polypeptide, or an ATP-binding cassette, sub-family D (ALD), member 1 (ABCD1) polypeptide.

Particular embodiments contemplated herein, also include polypeptide "variants." The recitation polypeptide "variant" refers to polypeptides that are distinguished from a reference polypeptide by the addition, deletion, truncations, modifications, and/or substitution of at least one amino acid residue, and that retain a biological activity. In certain embodiments, a polypeptide variant is distinguished from a reference polypeptide by one or more substitutions, which may be conservative or non-conservative, as known in the art.

In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, amino acid additions or deletions occur at the C-terminal end and/or the N-terminal end of the reference polypeptide.

As noted above, polypeptides of the invention may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985) Proc. Natl. Acad. Sci. USA. 82: 488-492, Kunkel et al., (1987) Methods in Enzymol, 154: 367-382, U.S. Pat. No. 4,873,192, Watson, J. D. et al., (1987) Molecular Biology of the Gene, Fourth Edition, Benjamin/Cummings, Menlo Park, Calif., and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.). A "host cell" includes cells transfected, infected, or transduced in vivo, ex vivo, or in vitro with a recombinant vector or a polynucleotide contemplated herein. Host cells may include packaging cells, producer cells, and cells infected with viral vectors. In particular embodiments, host cells infected with viral vector of the invention are administered to a subject in need of therapy. In certain embodiments, the term "target cell" is used interchangeably with host cell and refers to transfected, infected, or transduced cells of a desired cell type. In preferred embodiments, the target cell is a stem cell or progenitor cell. In certain preferred embodiments, the target cell is a somatic cell, e.g., adult stem cell, progenitor cell, or differentiated cell. In particular preferred embodiments, the target cell is a hematopoietic cell, e.g., a hematopoietic stem or progenitor cell. Further therapeutic target cells are discussed, infra.

In particular embodiments, the target cells is a primary cell. The term "primary cell" as used herein is known in the art to refer to a cell that has been isolated from a tissue and has been established for growth in vitro or ex vivo. Corresponding cells have undergone very few, if any, population doublings and are therefore more representative of the main functional component of the tissue from which they are derived in comparison to continuous cell lines, thus representing a more representative model to the in vivo state. Methods to obtain samples from various tissues and methods to establish primary cell lines are well-known in the art (see, e.g., Jones and Wise, *Methods Mol Biol.* 1997). Primary cells for use in the method of the invention are derived from, e.g., blood, lymphoma and epithelial tumors. In one embodiment, the primary cell is a hematopoietic stem or progenitor cell.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Symmetric cell division produces two identical daughter cells. "Proliferation" or "expansion" of cells refers to symmetrically dividing cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector contemplated in particular embodiments can be introduced into a packaging cell line, via transfection, transduction or infection, to generate a producer cell or cell line. The packaging vectors of can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by IRES or self-cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells of the invention are encoded on a separate vector from the viral gag and pol genes, as has been previously described.

Illustrative examples of retroviral-derived env genes which can be employed in the invention include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, and EIAV.

In other embodiments, envelope proteins for pseudotyping a virus of present invention include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In one embodiment, packaging cells which produce recombinant retrovirus, e.g., lentivirus, pseudotyped with the VSV-G glycoprotein are contemplated.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells. In a preferred embodiment, lentiviral envelope proteins are pseudotyped with VSV-G. In one embodiment, packaging cells produce recombinant retrovirus, e.g., lentivirus, pseudotyped with the VSV-G envelope glycoprotein.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. In particular embodiments, suitable cell line can be employed to prepare packaging cells of the invention. Generally, the cells are mammalian cells. In a particular embodiment, the cells used to produce the packaging cell line are human cells. Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRC5 cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells. In preferred embodiments, the packaging cells are 293 cells, 293T cells, 293F cells, or A549 cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art, e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

By "enhance" or "promote," or "increase" or "expand" refers generally to the ability of the compositions and/or methods contemplated herein to elicit, cause, or produce higher numbers of transduced cells compared to the number of cells transduced by either vehicle or a control molecule/composition. In one embodiment, a hematopoietic stem or progenitor cell transduced with compositions and methods contemplated herein comprises an increase in the number of transduced cells compared to existing transduction compositions and methods. Increases in cell transduction, can be ascertained using methods known in the art, such as reporter assays, RT-PCR, and cell surface protein expression, among others. An "increased" or "enhanced" amount of transduction is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the number of cells transduced by vehicle, a control composition, or other transduction method.

By "decrease" or "lower," or "lessen," or "reduce," or "abate" refers generally to compositions or methods that result in comparably fewer transduced cells compared to cells transduced with compositions and/or methods according to the present invention. A "decrease" or "reduced" amount of transduced cells is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the number of transduced cells (reference response) produced by compositions and/or methods according to the present invention.

By "maintain," or "preserve," or "maintenance," or "no change," or "no substantial change," or "no substantial decrease" refers generally to a physiological response that is comparable to a response caused by either vehicle, a control molecule/composition, or the response in a particular cell. A comparable response is one that is not significantly different or measurable different from the reference response.

In the following description, certain specific details are set forth in order to provide a thorough understanding of various illustrative embodiments of the invention contemplated herein. However, one skilled in the art will understand that particular illustrative embodiments may be practiced without these details. In addition, it should be understood that the individual vectors, or groups of vectors, derived from the various combinations of the structures and substituents described herein, are disclosed by the present application to the same extent as if each vector or group of vectors was set forth individually. Thus, selection of particular vector structures or particular substituents is within the scope of the present disclosure.

C. Agents

Various embodiments contemplated herein, arise from the unexpected finding that transduction efficiency and/or VCN is significantly increased by contacting cells, in vitro, ex vivo, or in vivo, with a retrovirus and one or more agents that increase transduction efficiency or VCN contemplated herein. In various embodiments, transduction efficiency is significantly increased by contacting cells, in vitro, ex vivo, or in vivo, with a retrovirus, and a poloxamer. In various embodiments, transduction efficiency is significantly increased by contacting cells, in vitro, ex vivo, or in vivo, with a retrovirus, and a poloxamer, optionally in combination with one or more polycationic polymers or peptides. In various embodiments, transduction efficiency is significantly increased by contacting cells, in vitro, ex vivo, or in vivo, with a retrovirus, a poloxamer, and one or more agents that stimulate the prostaglandin EP receptor signaling pathway and/or staurosporine, optionally in combination with one or more polycationic polymers or peptides.

1. Prostaglandin EP Receptor Signaling Pathway Agonists

Surprisingly, the present inventors have discovered that transduction efficiency and/or VCN of populations of cells comprising hematopoietic stem and progenitor cells can be increased by culturing the cells in the presence of a retrovirus, a poloxamer and one or more agents that stimulate the prostaglandin EP receptor signaling pathway, and analogs and derivatives thereof.

In particular embodiments, a population of cells comprising hematopoietic stem or progenitors cells is transduced by culturing the cells in the presence of a retrovirus in the presence of one or more agents that stimulate the prostaglandin EP receptor signaling pathway, i.e., a prostaglandin EP receptor signaling pathway agonist, and a poloxamer.

Agents that stimulate the prostaglandin EP receptor signaling include, but are not limited to small molecules, or those compounds disclosed in WO 2007/112084 and WO2010/108028, each of which is herein incorporated by reference in its entirety. As used herein, the terms "stimulate the prostaglandin EP receptor signaling," "activate the prostaglandin EP receptor signaling," or "increase the prostaglandin EP receptor signaling" generally refers to the ability of an agent to increase the cell signaling activity downstream of a prostaglandin EP receptor in the cell contacted with the one or more agents compared to the cell signaling activity downstream of the prostaglandin EP receptor in the absence of the one or more agents. Assays that can be used to measure activation or stimulation of the prostaglandin EP receptor signaling pathway are known in the art, and are described in, for example, WO2010/108028, which is herein incorporated by reference in its entirety.

Illustrative examples of agents that stimulate the prostaglandin EP receptor signaling pathway include, but are not limited to, small molecules, e.g., small organic molecules, prostaglandins, Wnt pathway agonists, cAMP/PI3K/AKT pathway agonists, $Ca^{2+}$ second messenger pathway agonists, nitric oxide (NO)/angiotensin signaling agonists, and other compounds known to stimulate the prostaglandin signaling pathway selected from the group consisting of: Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlorotrianisene, and derivatives of these compounds.

In particular embodiments, the agent that stimulates the prostaglandin pathway is a naturally-occurring or synthetic chemical molecule or polypeptide that binds to and/or interacts with an EP receptor, typically to activate or increase one or more of the downstream signaling pathways associated with a prostaglandin EP receptor.

In one embodiment, the agent that stimulates the prostaglandin pathway is selected from the group consisting of: $PGA_2$; $PGB_2$; $PGD_2$; $PGE_1$ (Alprostadil); $PGE_2$; $PGF_2$; $PGI_2$ (Epoprostenol); $PGH_2$; $PGJ_2$; and derivatives and analogues thereof.

Additional illustrative agents that stimulate the prostaglandin pathway include, but are not limited to 15d-$PGJ_2$; delta12-$PGJ_2$; 2-hydroxyheptadecatrienoic acid (HHT); Thromboxane ($TXA_2$ and $TXB_2$); $PGI_2$ analogs, e.g., Iloprost and Treprostinil; $PGF_2$ analogs, e.g., Travoprost, Carboprost tromethamine, Tafluprost, Latanoprost, Bimatoprost, Unoprostone isopropyl, Cloprostenol, Oestrophan, and Superphan; PGE1 analogs, e.g., 11-deoxy $PGE_1$, Misoprostol and Butaprost; and Corey alcohol-A [[3aα,4α,5⊕,6aα]-(−)-[Hexahydro-4-(hydroxymetyl)-2-oxo-2H-cyclopenta/b/furan-5-yl][1,1'-bifenyl]-4-carboxylate]; Corey alcohol-B [2H-Cyclopenta[b]furan-2-on,5-(benzoyloxy) hexahydro-4-(hydroxymethyl)[3aR-(3aα,4α,5β,6aα)]]; and Corey diol ((3aR,4S,5R,6aS)-hexahydro-5-hydroxy-4-(hydroxymethyl)-2H-cyclopenta[b]furan-2-one).

In one embodiment, the agent is a prostaglandin EP receptor ligand including, but not limited to, prostaglandin $E_2$ ($PGE_2$), as well as "analogs" or "derivatives" thereof. Prostaglandins relate generally to hormone like molecules that are derived from fatty acids containing 20 carbon atoms, including a 5-carbon ring, as described herein and known in the art.

Illustrative examples of $PGE_2$ "analogs" or "derivatives" include, but are not limited to, 16,16-dimethyl PGE2, 16-16 dimethyl $PGE_2$ p-(p-acetamidobenzamido) phenyl ester, 11-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15 (R)-15-methyl $PGE_2$, 8-iso-15-keto $PGE_2$, 8-iso $PGE_2$ isopropyl ester, 20-hydroxy $PGE_2$, nocloprost, sulprostone, butaprost, 15-keto $PGE_2$, and 19 (R) hydroxyy $PGE_2$.

Also contemplated herein are prostaglandin analogs or derivatives having a similar structure to $PGE_2$ that are substituted with halogen at the 9-position (see, e.g., WO 2001/12596, herein incorporated by reference in its entirety), as well as 2-decarboxy-2-phosphinico prostaglandin derivatives, such as those described in U.S. Publication No. 2006/0247214, herein incorporated by reference in its entirety).

In some embodiments, the compound is a non-$PGE_2$-based ligand. In certain embodiments, the non-$PGE_2$-based ligand is selected from the group consisting of an $EP_1$ agonist, an $EP_2$ agonist, an $EP_3$ agonist, and an $EP_4$ agonist.

In particular embodiments, the prostaglandin EP receptor is selected from $EP_1$, $EP_2$, $EP_3$, and $EP_4$.

Illustrative examples of non-$PGE_2$-based EPi agonists include, but are not limited to, ONO-DI-004 and ONO-8713. Illustrative examples of non-$PGE_2$-based $EP_2$ agonists include, but are not limited to, CAY10399, ONO_8815Ly, ONO-AE1-259, and CP-533,536. Additional examples of non-$PGE_2$-based $EP_2$ agonists include the carbazoles and fluorenes disclosed in WO 2007/071456, herein incorporated by reference for its disclosure of such agents. Illustrative examples of non-$PGE_2$-based $EP_3$ agonist include, but are not limited to, AE5-599, MB28767, GR 63799X, ONO-NT012, and ONO-AE-248. Illustrative examples of non-$PGE_2$-based $EP_4$ agonist include, but are not limited to, ONO-4819, APS-999 Na, AH23848, and ONO-AE 1-329. Additional examples of non-$PGE_2$-based $EP_4$ agonists can be found in WO 2000/038663; U.S. Pat. Nos. 6,747,037; and 6,610,719, each of which are incorporated by reference for their disclosure of such agonists.

In one embodiment, the agent that stimulates the prostaglandin EP receptor signaling pathway is a Wnt agonist. Illustrative examples of Wnt agonists include, but are not limited to Wnt polypeptides and glycogen synthase kinase 3 (GSK3) inhibitors. Illustrative examples of wnt polypeptides suitable for use as compounds that stimulate the prostaglandin EP receptor signaling pathway include, but are not limited to, Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt15 and biologically active fragments thereof.

GSK3 inhibitors suitable for use as agents that stimulate the prostaglandin EP receptor signaling pathway bind to and decrease the activity of GSK3α, or GSK3β. Illustrative examples of GSK3 inhibitors include, but are not limited to, BIO (6-bromoindirubin-3'-oxime), LiCl or other GSK-3 inhibitors, as exemplified in U.S. Pat. Nos. 6,057,117 and 6,608,063; and U.S. applications 2004/0092535 and 2004/0209878; ATP-competitive, selective GSK-3 inhibitors CHIR-911 and CH1R-837 (also referred to as CT-99021 and CT-98023 respectively). Chiron Corporation (Emeryville, CA).

In another embodiment, the agent that stimulates the prostaglandin EP receptor signaling pathway increases signaling through the cAMP/PI3K/AKT second messenger pathway and is selected from the group consisting of dibutyryl cAMP (DBcAMP), phorbol ester, forskolin, sclareline, 8-bromo-cAMP, cholera toxin (CTx), aminophylline, 2,4 dinitrophenol (DNP), norepinephrine, epinephrine, isoproterenol, isobutylmethylxanthine (IBMX), caffeine, theophylline (dimethylxanthine), dopamine, rolipram, iloprost, pituitary adenylate cyclase activating polypeptide (PACAP), and vasoactive intestinal polypeptide (VIP, and derivatives of these agents.

In yet another embodiment, the agent that stimulates the prostaglandin EP receptor signaling pathway increases signaling through the Ca2+ second messenger pathway and is selected from the group consisting of Bapta-AM, Fendiline, Nicardipine and derivatives of these agents.

In another embodiment, the agent that stimulates the prostaglandin EP receptor signaling pathway increases signaling through the NO/Angiotensin signaling pathway and is selected from the group consisting of L-Arg, Sodium Nitroprusside, Sodium Vanadate, Bradykinin, and derivatives thereof.

In one embodiment, a method of improving transduction efficiency is provided, comprising culturing a population of cells with a retrovirus and a poloxamer and one or more agents that increases the prostaglandin EP receptor signaling selected from the group consisting of: a prostaglandin, $PGE_2$; $PGD_2$; $PGI_2$; Linoleic Acid; 13(s)-HODE; LY171883; Mead Acid; Eicosatrienoic Acid; Epoxyeicosatrienoic Acid; ONO-259; Cay1039; a $PGE_2$ receptor agonist; 16,16-dimethyl $PGE_2$; 19(R)-hydroxy $PGE_2$; 16,16-dimethyl $PGE_2$ p-(p-acetamidobenzamido) phenyl ester; 11-deoxy-16,16-dimethyl $PGE_2$; 9-deoxy-9-methylene-16, 16-dimethyl $PGE_2$; 9-deoxy-9-methylene $PGE_2$; Butaprost; Sulprostone; $PGE_2$ serinol amide; $PGE_2$ methyl ester; 16-phenyl tetranor $PGE_2$; 15(S)-15-methyl $PGE_2$; 15(R)-15-methyl $PGE_2$; BIO; 8-bromo-cAMP; Forskolin; Bapta-AM; Fendiline; Nicardipine; Nifedipine; Pimozide; Strophanthidin; Lanatoside; L-Arg; Sodium Nitroprusside; Sodium Vanadate; Bradykinin; Mebeverine; Flurandrenolide; Atenolol; Pindolol; Gaboxadol; Kynurenic Acid; Hydralazine; Thiabendazole; Bicuclline; Vesamicol; Peruvoside; Imipramine; Chlorpropamide; 1,5-Pentamethylenetetrazole; 4-Aminopyridine; Diazoxide; Benfotiamine; 12-Methoxydodecenoic acid; N-Formyl-Met-Leu-Phe; Gallamine; IAA 94; and Chlorotrianisene.

In a particular embodiment, a method of improving transduction efficiency comprises culturing a population of cells with a retrovirus and a poloxamer and one or more agents that are ligands of a prostaglandin EP receptor selected from the group consisting of: $PGE_2$, 16,16-dimethyl $PGE_2$, 16-16 dimethyl $PGE_2$ p-(p-acetamidobenzamido) phenyl ester, 11-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15 (R)-15-methyl $PGE_2$, 8-iso-15-keto $PGE_2$, 8-iso $PGE_2$ isopropyl ester, 20-hydroxy $PGE_2$, nocloprost, sulprostone, butaprost, 15-keto $PGE_2$, and 19 (R) hydroxyy $PGE_2$.

In particular embodiments, the agent that stimulates a prostaglandin EP receptor pathway is $PGE_2$ or 16,16-dimethyl $PGE_2$.

In one embodiment, the agent that stimulates a prostaglandin EP receptor pathway is $PGE_2$.

In various embodiments, a population of cells is cultured in the presence of a retrovirus, one or more agents that stimulated the prostaglandin EP receptor signaling pathway and a poloxamer having an average molecular weight of about 10,000 Daltons.

In various embodiments, a population of cells is cultured in the presence of a retrovirus, one or more agents that stimulate the prostaglandin EP receptor signaling pathway and a poloxamer that has an average molecular weight of polypropylene subunits greater than about 2250 Daltons and comprises greater than about 40% polyethylene oxide.

In particular embodiments, the poloxamer has an average molecular weight of polypropylene subunits of at least about 2750 Daltons.

In particular embodiments, the poloxamer has an average molecular weight of polypropylene subunits of at least about 3250 Daltons.

In particular embodiments, the poloxamer has an average molecular weight of polypropylene subunits of at least about 4000 Daltons.

In particular embodiments, the poloxamer comprises at least about 50% polyethylene oxide.

In particular embodiments, the poloxamer comprises at least about 60% polyethylene oxide.

In particular embodiments, the poloxamer comprises at least about 70% polyethylene oxide.

In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide.

In particular embodiments, the poloxamer has an average molecular weight of polypropylene subunits of at least about 2750 Daltons and the poloxamer comprises at least about 50% polyethylene oxide.

In particular embodiments, the poloxamer has an average molecular weight of polypropylene subunits of at least about 3250 Daltons and the poloxamer comprises at least about 50% polyethylene oxide.

In certain embodiments, the poloxamer is selected from the group consisting of: poloxamer 288, poloxamer 335, poloxamer 338, and poloxamer 407.

In one embodiment, the poloxamer is poloxamer 288.
In one embodiment, the poloxamer is poloxamer 335.
In one embodiment, the poloxamer is poloxamer 338.
In one embodiment, the poloxamer is poloxamer 407.

2. STA Urosporine

Staurosporine, an alkaloid produced in *Streptomyces staurospores* originally as an antifungal agent in 1977. Staurosporine is a broad spectrum protein kinase inhibitor, inhibiting kinases such as, for example, protein kinase C (PKC), cAMP-dependent protein kinase (PKA), phosphorylase kinase, ribosomal protein S6 kinase, epidermal growth factor receptor (EGF-R) kinase and $Ca^{2+}$/calmodulin-dependent protein kinase II (Ca/CaM PKII). The inhibition potency is strongest for PKC ($IC_{50}$=2.7 nM) but several-fold lower for other protein kinases. Staurosporine exhibits a strong cytotoxicity to some mammalian tumor cell lines, induces cell apoptosis, and arrests fission yeast cell elongation specifically at a stage immediately after cell division.

Surprisingly, the present inventors have also discovered that transduction efficiency and/or VCN of populations of cells comprising hematopoietic stem and progenitor cells can be increased by culturing the cells in the presence of a retrovirus, a poloxamer and staurosporine, and analogs and derivatives thereof.

In various embodiments, a population of cells is cultured in the presence of a retrovirus, staurosporine, and a poloxamer that has an average molecular weight of about 10,000 Daltons.

In various embodiments, a population of cells is cultured in the presence of a retrovirus, staurosporine, and a poloxamer that has an average molecular weight of polypropylene subunits greater than about 2250 Daltons and comprises greater than about 40% polyethylene oxide.

In particular embodiments, the poloxamer has an average molecular weight of polypropylene subunits of at least about 2750 Daltons.

In particular embodiments, the poloxamer has an average molecular weight of polypropylene subunits of at least about 3250 Daltons.

In particular embodiments, the poloxamer has an average molecular weight of polypropylene subunits of at least about 4000 Daltons.

In particular embodiments, the poloxamer comprises at least about 50% polyethylene oxide.

In particular embodiments, the poloxamer comprises at least about 60% polyethylene oxide.

In particular embodiments, the poloxamer comprises at least about 70% polyethylene oxide.

In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide.

In particular embodiments, the poloxamer has an average molecular weight of polypropylene subunits of at least about 2750 Daltons and the poloxamer comprises at least about 50% polyethylene oxide.

In particular embodiments, the poloxamer has an average molecular weight of polypropylene subunits of at least about 3250 Daltons and the poloxamer comprises at least about 50% polyethylene oxide.

In certain embodiments, the poloxamer is selected from the group consisting of: poloxamer 288, poloxamer 335, poloxamer 338, and poloxamer 407.

In one embodiment, the poloxamer is poloxamer 288.
In one embodiment, the poloxamer is poloxamer 335.
In one embodiment, the poloxamer is poloxamer 338.
In one embodiment, the poloxamer is poloxamer 407.

3. Poloxamers and Polycationic Polymers

In particular embodiments, transduction efficiency is increased in a population of cells comprising hematopoietic stem or progenitors cells by culturing the cells in the presence of a retrovirus and a poloxamer.

In particular embodiments, transduction efficiency is increased in a population of cells comprising hematopoietic stem or progenitors cells by culturing the cells in the presence of a retrovirus in the presence of one or more agents that stimulate the prostaglandin EP receptor signaling pathway or staurosporine, and a poloxamer.

In particular embodiments, VCN is increased in a population of cells comprising hematopoietic stem or progenitors cells is efficiently transduced by culturing the cells in the presence of a retrovirus in the presence of one or more agents that stimulate the prostaglandin EP receptor signaling pathway or staurosporine, and a poloxamer.

"Poloxamer" refers to a non-ionic triblock copolymer composed of a central hydrophobic chain of polyoxypropylene flanked by two hydrophilic chains of polyoxyethylene. Poloxamers are also known by the trade name of "Pluronics" or "Synperonics" (BASF). The block copolymer can be represented by the following formula: $HO(C_2H_4O)_x(C_3H_6O)_y(C_2H_4O)_zH$.

The lengths of the polymer blocks can be customized; as a result many different poloxamers exist. Poloxamers suitable for use in particular embodiments have an average molecular weight of at least about 10 kDa, at least about 11.4 kDa, at least about 12.6 kDa, at least about 13 kDa, at least about 14.6 kDa, or at least about 15 kDa. In particular embodiments, y can be in the range of about 39 to about 70.

In particular embodiments, y is at least about 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 or more.

In particular embodiments, x+z can be in the range of about 70 to about 275.

In particular embodiments, x+z can be in the range of about 200 to about 275.

In particular embodiments, x+z is at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 191, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275.

In particular embodiments, x+z is at least about 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256 257, 258, 259, 260, 261, 262, 263, 264, 265, 266, 267, 268, 269, 270, 271, 272, 273, 274, or 275 or more.

In particular embodiments, poloxamers suitable for use in particular embodiments have an average molecular weight of polypropylene subunits of greater than about 2250 Daltons, at least about 2300 Daltons, at least about 2350

Daltons, at least about 2400 Daltons, at least about 2450 Daltons, at least about 2500 Daltons, at least about 2550 Daltons, at least about 2600 Daltons, at least about 2650 Daltons, at least about 2700 Daltons, at least about 2750 Daltons, at least about 2800 Daltons, at least about 2850 Daltons, at least about 2900 Daltons, at least about 2950 Daltons, at least about 3000 Daltons, at least about 3050 Daltons, at least about 3100 Daltons, at least about 3150 Daltons, at least about 3200 Daltons, at least about 3250 Daltons, at least about 3300 Daltons, at least about 3350 Daltons, at least about 3400 Daltons, at least about 3450 Daltons, at least about 3500 Daltons, at least about 3550 Daltons, at least about 3600 Daltons, at least about 3650 Daltons, at least about 3700 Daltons, at least about 3750 Daltons, at least about 3800 Daltons, at least about 3850 Daltons, at least about 3900 Daltons, at least about 3950 Daltons, at least about 4000 Daltons, at least about 4050 Daltons, or at least about 4100 Daltons.

In particular embodiments, poloxamers suitable for use in particular embodiments comprise about 40%, about 50%, about 60%, about 70%, or about 80% polyethylene oxide.

In particular embodiments, poloxamers suitable for use in particular embodiments have an average molecular weight of polypropylene subunits of greater than about 2250 Daltons, at least about 2300 Daltons, at least about 2350 Daltons, at least about 2400 Daltons, at least about 2450 Daltons, at least about 2500 Daltons, at least about 2550 Daltons, at least about 2600 Daltons, at least about 2650 Daltons, at least about 2700 Daltons, at least about 2750 Daltons, at least about 2800 Daltons, at least about 2850 Daltons, at least about 2900 Daltons, at least about 2950 Daltons, at least about 3000 Daltons, at least about 3050 Daltons, at least about 3100 Daltons, at least about 3150 Daltons, at least about 3200 Daltons, at least about 3250 Daltons, at least about 3300 Daltons, at least about 3350 Daltons, at least about 3400 Daltons, at least about 3450 Daltons, at least about 3500 Daltons, at least about 3550 Daltons, at least about 3600 Daltons, at least about 3650 Daltons, at least about 3700 Daltons, at least about 3750 Daltons, at least about 3800 Daltons, at least about 3850 Daltons, at least about 3900 Daltons, at least about 3950 Daltons, at least about 4000 Daltons, at least about 4050 Daltons, or at least about 4100 Daltons; and contain at least about 40%, at least about 50%, at least about 60%, at least about 70%, or at least about 80% polyethylene oxide.

In one embodiment, poloxamers suitable for use in particular embodiments have an average molecular weight of polypropylene subunits of at least about 3200 Daltons and contain at least about 50% polyethylene oxide.

As synthesis of block copolymers cannot be accurate, the above given values may not exactly be achievable upon synthesis and the average value will differ to a certain extent. Thus, the term "poloxamer" as used herein can be used interchangeably with the term "poloxamers" (representing an entity of several poloxamers, also referred to as mixture of poloxamers) if not explicitly stated otherwise. The term "average" in relation to the number of monomer units or molecular weight of (a) poloxamer(s) as used herein is a consequence of the technical inability to produce poloxamers all having the identical composition and thus the identical molecular weight. Poloxamers produced according to state of the art methods will be present as a mixture of poloxamers each showing a variability as regards their molecular weight, but the mixture as a whole averaging the molecular weight specified herein. BASF and Sigma Aldrich are suitable sources of poloxamers for use in particular embodiments contemplated herein.

The inventors have surprisingly found that poloxamers as defined herein alone or in combination with an agent that stimulates the prostaglandin EP receptor signaling pathway or staurosporine significantly enhance the transduction efficiency and/or VCN of retroviral vectors in adherent and suspension target cells without essentially affecting their viability.

In one embodiment, a poloxamer suitable for use in particular embodiments contemplated herein is selected from the group consisting of: poloxamer 288, poloxamer 335, poloxamer 338, and poloxamer 407.

In one embodiment, a poloxamer suitable for use in particular embodiments contemplated herein is poloxamer 288.

In one embodiment, a poloxamer suitable for use in particular embodiments contemplated herein is poloxamer 335.

In one embodiment, a poloxamer suitable for use in particular embodiments contemplated herein is poloxamer 338.

In one embodiment, a poloxamer suitable for use in particular embodiments contemplated herein is poloxamer 407.

In one embodiment, poloxamer 288 (F98; $HO(C_2H_4O)_x(C_3H_6O)_y(C_2H_4O)_zH$; x+y=236.36, z=44.83; average molecular weight of 13 kDa) is used to increase transduction efficiency and/or VCN in a population of hematopoietic cells comprising hematopoietic stem or progenitor cells. F98 can be used alone, or in combination with an agent that stimulates the prostaglandin EP receptor signaling pathway or staurosporine to increase transduction efficiency and/or VCN.

In one embodiment, poloxamer 335 (P105; $HO(C_2H_4O)_x(C_3H_6O)_y(C_2H_4O)_zH$; x+y=73.86, z=56.03; average molecular weight of 6.5 kDa) is used to increase transduction efficiency and/or VCN in a population of hematopoietic cells comprising hematopoietic stem or progenitor cells. P105 can be used alone, or in combination with an agent that stimulates the prostaglandin EP receptor signaling pathway or staurosporine to increase transduction efficiency and/or VCN.

In one embodiment, poloxamer 338 (F108; $HO(C_2H_4O)_x(C_3H_6O)_y(C_2H_4O)_zH$; x+y=265.45, z=50.34; average molecular weight of 14.6 kDa) is used to increase transduction efficiency and/or VCN in a population of hematopoietic cells comprising hematopoietic stem or progenitor cells. F108 can be used alone, or in combination with an agent that stimulates the prostaglandin EP receptor signaling pathway or staurosporine to increase transduction efficiency and/or VCN.

In one embodiment, poloxamer 407 (F127; $HO(C_2H_4O)_x(C_3H_6O)_y(C_2H_4O)_zH$; x+y=200.45, z=65.17; average molecular weight of 12.6 kDa) is used to increase transduction efficiency and/or VCN in a population of hematopoietic cells comprising hematopoietic stem or progenitor cells. F127 can be used alone, or in combination with an agent that stimulates the prostaglandin EP receptor signaling pathway or staurosporine to increase transduction efficiency and/or VCN.

In a particular embodiment, a population of hematopoietic cells comprising hematopoietic stem or progenitor cells is cultured in the presence of a retrovirus and a poloxamer to increase transduction efficiency and/or VCN.

In a particular embodiment, a population of hematopoietic cells comprising hematopoietic stem or progenitor cells is cultured in the presence of a retrovirus, a poloxamer, an agent that stimulates the prostaglandin EP receptor signaling pathway or staurosporine, and a polycationic polymer, to increase transduction efficiency and/or VCN.

"Polycationic polymers" refers to charged polymers whose repeating units bear a positive charge, wherein the positive charge on a repeating unit is stems from protonated nitrogen moieties. Illustrative examples of polycationic polymers that are suitable for use in particular embodiments contemplated herein include, but are not limited to polyethylenimine (PEI), poly(ethylene glycol)-poly(L-lysine) block copolymer (PEG-PLL),1,5-Dimethyl-,5-Diaza-undeca-methyl-polymethobromide (Polybrene), polycationic peptides, e.g., poly-L-lysine, and protamine sulfate.

D. Viral Vectors

Retroviral and lentiviral vectors have been tested and found to be suitable delivery vehicles for the stable introduction of genes of interest, e.g., encoding therapeutic polypeptides, into the genome of a broad range of target cells. Particular embodiments contemplated herein, provide improved transduction efficiency and/or VCN of gene therapy vectors to a population of cells that are administered to a subject to provide gene therapy.

In one embodiment, the vector is a transfer vector. While the skilled artisan will appreciate that such transfer vectors may be produced using a variety of different viral vectors, in particular embodiments, the transfer vector is a retroviral vector or a lentiviral vector, in part since lentiviral vectors are capable of providing efficient delivery, integration and long term expression of transgenes into non-dividing cells both in vitro and in vivo. A variety of lentiviral vectors are known in the art, see Naldini et al., (1996a, 1996b, and 1998); Zufferey et al., (1997); Dull et al., 1998, U.S. Pat. Nos. 6,013,516; and 5,994,136, any of which may be adapted to produce a transfer vector contemplated herein.

In general, these vectors are plasmid-based or virus-based, and are configured to carry the essential sequences for transfer of a nucleic acid encoding a therapeutic polypeptide into a host cell.

In illustrative embodiments, the retroviral vector is a lentiviral vector. Thus, the vectors may be derived from human immunodeficiency-1 (HIV-1), human immunodeficiency-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), caprine arthritis encephalitis virus (CAEV) and the like. HIV based vector backbones (i.e., HIV cis-acting sequence elements and HIV gag, pol and rev genes) are generally be preferred in connection with most aspects of the present invention in that HIV-based constructs are the most efficient at transduction of human cells.

Although particular illustrative embodiments include more detailed description of vectors, compositions and methods used to correct hematopoietic disorders, e.g., hemoglobinopathies, the embodiments contemplated herein should not be considered to be limited by this disclosure. One having skill in the art would readily appreciate that the principles illustrated herein can be applied to gene therapy in other systems, e.g., nervous system, including the eye, central nervous system, and peripheral nervous system; the circulatory system; the muscular system; the skeletal system; organs, including the skin, heart, lungs, pancreas, liver, kidney, intestine, and the like.

In one embodiment, retroviral vectors comprise an expression control sequence that directs expression of polynucleotide-of-interest, e.g., a globin gene, in a particular cell type or cell lineage. The use of a cell type or cell lineage expression control sequence offers safety advantages in restricting polynucleotide expression to a desired stage of cell differentiation in a single lineage; and thus, vectors of the invention alleviate concerns dealing with ectopic expression of polypeptides in undesired cells types.

In one non-limiting example, the expression control sequence may be a ubiquitous expression control sequence as disclosed elsewhere herein.

In another non-limiting example, the expression control sequence may be a stem cell specific expression control sequence that directs stem cell specific expression of the polynucleotide—of-interest in an embryonic stem cell, a neural stem cell, a mesenchymal stem cell, a liver stem cell, a pancreatic stem cell, a cardiac stem cell, a kidney stem cell, or a hematopoietic stem cell.

In yet another non-limiting example, the expression control sequence may a cell type or cell lineage specific expression control sequence that directs expression of the polynucleotide-of-interest in a hematopoietic stem cell, a hematopoietic progenitor cell, a myeloid cell, a lymphoid cell, a thrombopoietic lineage, a mast cell, an erythropoietic lineage cell, a granulopoietic lineage cell, and a monocytopoietic lineage cell.

In particular embodiments, a vector contemplated herein expresses a polynucleotide, e.g., gene-of-interest in one or more or all hematopoietic cells including, but not limited to hematopoietic stem cells, hematopoietic progenitor cells, myeloid progenitors, lymphoid progenitors, thrombopoietic progenitors, erythroid progenitors, granulopoietic progenitors, monocytopoietic progenitors, megakaryoblasts, pro-megakaryocytes, megakaryocytes, thrombocytes/platelets, proerythroblasts, basophilic erythroblasts, polychromatic erythroblasts, orthochromatic erythroblasts, polychromatic erythrocytes, erythrocytes (RBCs), basophilic promyelocytes, basophilic myelocytes, basophilic metamyelocytes, basophils, neutrophilic promyelocytes, neutrophilic myelocytes, neutrophilic metamyelocytes, neutrophils, eosinophilic promyelocytes, eosinophilic myelocytes, macrophages, dendritic cells, lymphoblasts, prolymphocytes, natural killer (NK)-cells, small lymphocytes, T-lymphocytes, B-lymphocytes, plasma cells, and lymphoid dendritic cells.

In preferred embodiments, a vector expresses a polynucleotide, e.g., gene-of-interest in one or more erythroid cells, e.g., proerythroblast, basophilic erythroblast, polychromatic erythroblast, orthochromatic erythroblast, polychromatic erythrocyte, and erythrocyte (RBC).

In one embodiment, the vector comprises a hematopoietic cell promoter, enhancer, or promoter/enhancer operably linked to a gene of interest, e.g., globin.

Suitable cell type or cell lineage specific expression control sequences include, but are not limited to hematopoietic cell expression control sequences, such as, for example, a hematopoietic stem cell promoter, and a hematopoietic progenitor cell promoter. In embodiments where expression of the gene of interest is desired in one or more erythroid cells, a suitable hematopoietic cell expression control sequence can include, but is not limited to, an erythroid cell specific promoter and optionally an erythroid cell specific enhancer, a human β-globin promoter, a human β-globin LCR, or a human a-globin HS40 enhancer and an ankyrin-1 promoter.

In one embodiment, suitable cell type or cell lineage specific expression control sequences include, but are not limited to a promoter active in a microglial cell. In certain embodiments, the promoter comprises a MND promoter or transcriptionally active fragment thereof, operably linked to a gene of interest, e.g., ABCD1.

The use of a cell type or cell lineage expression control sequence offers safety advantages in restricting polynucleotide expression to this a desired stage of cell differentiation in a single lineage; and thus, vectors contemplated herein alleviate concerns dealing with ectopic expression of polypeptides in undesired cells types. In one embodiment, a vector comprises one or more LTRs, and an expression control sequence operably linked to a gene of interest. In related embodiment, the expression control sequence is an erythroid cell specific expression control sequence is selected from the group consisting of: a human β-globin promoter; a human β-globin LCR; and a human α-globin HS40 enhancer and an ankyrin-1 promoter.

In various embodiments, the design of the vector will be made with the goal of treating, preventing, or ameliorating a particular hematopoietic disease, disorder, or condition. For example, the present invention contemplates vectors for gene therapy of hemoglobinopathies that comprise a gene of interest selected from the group consisting of: human α-globin, human β-globin, human δ-globin, and human γ-globin, or biologically active variants or fragments thereof. In one embodiment, the globin gene is selected from the group consisting of a wild type human β-globin gene, a deleted human β-globin gene comprising one or more deletions of intron sequences, and a mutated human β-globin gene encoding at least one antisickling amino acid residue.

In a particular embodiment, wherein the condition being treated is a hemoglobinopathy, e.g., a thalassemia or sickle cell disease, the gene of interest can be an antisickling protein. As used herein, "antisickling protein" refers to a polypeptide that prevents or reverses the pathological events leading to sickling of erythrocytes in sickle cell conditions. In one embodiment of the invention, the transduced cells of the invention are used to deliver antisickling proteins to a subject with a hemoglobinopathic condition. Antisickling proteins also include mutated β-globin genes comprising antisickling amino acid residues.

In a preferred embodiment, one such globin variant is the human βA-globin gene encoding a threonine to glutamine mutation at codon 87 (βA-T87Q) or a human βA-globin gene (the mature form of the globin polypeptide has been processed by cleavage of the N-terminal methionine, codon 87 of the mature globin polypeptide is threonine; codon 88 of the full-length, non-cleaved globin polypeptide is threonine). Other antisickling amino acid residues are known in the art and may be useful in the present invention. For example, see U.S. Pat. Nos. 6,051,402; 5,861,488; 6,670,323; 5,864,029; 5,877,288; and Levasseur et al., Blood 102:4312-4319 (2003), which are herein incorporated by reference.

In certain embodiments, a vector that comprises an erythroid specific expression control sequence is used to treat, prevent, or ameliorate of a vast number of disorders extending well beyond the hemoglobinopathies. Red blood cell precursors are a useful cell population in which to express polypeptides that can be secreted into the circulation and thus delivered systemically. An example of such in vivo protein delivery is human Factor IX, a clotting factor that is missing in patients with Hemophilia B, see, e.g., A. H. Chang, et al., Molecular Therapy (2008), which is herein incorporated by reference. In one embodiment, cells transduced with vectors of the invention can be used as "factories" for protein secretion, in vitro, ex vivo, or in vivo. For example, a vector comprising an erythroid cell specific expression control sequence can be used for large-scale in vitro production of proteins from erythroid cells differentiated from HSCs or from embryonic stem cells.

Polynucleotides-of-interest that could be expressed in this way include, but are not limited to: adenosine deaminase, the enzymes affected in lysosomal storage diseases, apolipoprotein E, brain derived neurotropihic factor (BDNF), bone morphogenetic protein 2 (BMP-2), bone morphogenetic protein 6 (BMP-6), bone morphogenetic protein 7 (BMP-7), cardiotrophin 1 (CT-1), CD22, CD40, ciliary neurotrophic factor (CNTF), CCL1-CCL28, CXCL1-CXCL17, CXCL1, CXCL2, CX3CL1, vascular endothelial cell growth factor (VEGF), dopamine, erythropoietin, Factor IX, Factor VIII, epidermal growth factor (EGF), estrogen, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, granulocyte colony-stimulating factor (G-CSF), granulocyte macrophage stimulating factor (GM-CSF), growth hormone, hepatocyte growth factor (HGF), interferon alpha (IFN-a), interferon beta (IFN-b), interferon gamma (IFNg), insulin, glucagon, insulin-like growth factor 1(IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neurotrophin 3 (NT-3), neurotrophin 4 (NT-4), parathyroid hormone, platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), RANTES, stem cell factor (SCF), stromal cell derived factor 1 (SDF-1), testosterone, transforming growth factor alpha (TGF-a), transforming growth factor beta (TGF-b), tumor necrosis factor alpha (TNF-a), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

In one embodiment, a vector of the invention comprises at least one modified or unmodified retroviral LTR, e.g., lentiviral LTR, a β-globin promoter and a β-globin locus control region (LCR) operably linked to a polynucleotide of interest, e.g., encoding a globin polypeptide. Suitable modifications of the LTRs include, but are not limited to: replacement of the 5' LTR is with a heterologous promoter, e.g., cytomegalovirus (CMV) promoter, a Rous Sarcoma Virus (RSV) promoter, a thymidine kinase promoter, or a Simian Virus 40 (SV40) promoter; and one or more modifications, additions, and/or deletions of a 3' LTR as discussed elsewhere herein.

In a particular embodiment, erythroid specific expression of a polynucleotide is achieved using a human β-globin promoter, a β-globin LCR that comprises one or more of DNAase I hypersensitive sites 2, 3 and 4 from the human β-globin LCR, and/or a human β-globin 3' enhancer element.

In various embodiments, a vector contemplated herein comprises one or more elements selected from the group consisting of: a Psi packaging sequence (Ψ+), a central polypurine tract/DNA flap (cPPT/FLAP), a retroviral export element, a posttranscriptional regulatory element, one or more insulator elements, a polyadenylation sequence, a selectable marker, and a cell suicide gene, as discussed elsewhere herein.

In various embodiments, a vector contemplated herein comprises a promoter operable in hematopoietic cell operably linked to a gene encoding a polypeptide that provides therapy for hemoglobinopathies. The vectors may have one or more LTRs, wherein either LTR comprises one or more modifications, such as one or more nucleotide substitutions, additions, or deletions. The vectors may further comprise one or more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences).

In one embodiment, a vector comprises a left (5') retroviral LTR, a Psi packaging sequence (Ψ+), central polypurine tract/DNA flap (cPPT/FLAP), a retroviral export element, a β-globin promoter, a β-globin locus control region (LCR), and optionally a 3' β-globin enhancer operably linked to a polynucleotide of interest, and a right (3') retroviral LTR that comprises one or more insulator elements, or a polyadenylation sequence.

In particular embodiment, a vector is a lentiviral vector that comprises a left (5') HIV-1 LTR, a Psi packaging sequence (Ψ+), an HIV-1 central polypurine tract/DNA flap (cPPT/FLAP), a rev response element (RRE), a β-globin promoter, a β-globin locus control region (LCR), and optionally a 3' β-globin enhancer operably linked to a polynucleotide of interest, and a right (3') retroviral LTR that comprises one or more insulator elements, and a rabbit β-globin polyA sequence (rβgpA).

In various embodiments, a vector contemplated herein comprises a promoter operable in a microglial cell operably linked to a gene encoding a polypeptide that provides therapy for adrenoleukodystrophies and/or adrenomyeloneuropathies. The vectors may have one or more LTRs, wherein either LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences).

In a particular embodiment, a transfer vector contemplated herein comprises a left (5') retroviral LTR; a central polypurine tract/DNA flap (cPPT/FLAP); a retroviral export element; a promoter active in a microglial cell, operably linked to a polynucleotide encoding an ATP-binding cassette, sub-family D, member 1 (ABCD1) polypeptide; and a right (3') retroviral LTR.

In a certain embodiment, a lentiviral vector contemplated herein comprises: a left (5') HIV-1 LTR; a Psi (Ψ) packaging signal; a cPPT/FLAP; an RRE; a MND promoter, operably linked to a polynucleotide encoding a human ABCD1 polypeptide; a right (3') self-inactivating (SIN) HIV-1 LTR; and a rabbit β-globin polyadenylation sequence.

In particular embodiments, the lentiviral vector encodes an ATP-binding cassette, sub-family D, member 1 (ABCD1) polypeptide.

In further embodiments, the lentiviral vector comprises a myeloproliferative sarcoma virus enhancer, negative control region deleted, d1587rev primer-binding site substituted (MND) promoter or transcriptionally active fragment thereof operably linked to a polynucleotide encoding an ATP-binding cassette, sub-family D, member 1 (ABCD1) polypeptide.

In certain embodiments, the lentiviral vector encodes adenosine deaminase.

In certain embodiments, the lentiviral vector comprises an elongation factor 1 alpha promoter operably linked to a polynucleotide encoding adenosine deaminase.

In certain embodiments, the lentiviral vector encodes interleukin 2 receptor gamma.

In certain embodiments, the lentiviral vector comprises an elongation factor 1 alpha promoter operably linked to a polynucleotide encoding interleukin 2 receptor gamma.

In particular embodiments, the lentiviral vector encodes tripeptidyl peptidase 1.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding tripeptidyl peptidase 1.

In particular embodiments, the lentiviral vector encodes alpha-L iduronidase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding alpha-L iduronidase.

In particular embodiments, the lentiviral vector encodes iduronate 2-sulfatase.

In certain embodiments, the lentiviral vector comprises an elongation factor 1 alpha promoter or comprises a myeloproliferative sarcoma virus enhancer, negative control region deleted, d1587rev primer-binding site substituted (MND) promoter operably linked to a polynucleotide encoding iduronate 2-sulfatase.

In certain embodiments, the promoter comprises one or more elements of a human β-globin LCR.

In some embodiments, the human β-globin LCR comprises DNase I hypersensitive site 2, 3, and 4 from the human β-globin LCR.

In particular embodiments, the lentiviral vector further comprises a human β-globin 3' enhancer element.

In additional embodiments, the gene of interest encodes an antisickling protein or a globin gene.

In particular embodiments, the gene of interest encodes a human β-globin protein, a human δ-globin protein, a human γ-globin protein, a human $β^{A-T87Q}$-globin protein, a human $β^{A-G16D/E22A/T87Q}$-globin protein, or a human $β^{A-T87Q/K95E/K120E}$-globin protein.

In particular embodiments, the lentiviral vector is an AnkT9W vector, a T9Ank2W vector, a TNS9 vector, a lentiglobin HPV569 vector, a lentiglobin BB305 vector, a BG-1 vector, a BGM-1 vector, a d432βAγ vector, a mLARβAγV5 vector, a GLOBE vector, a G-GLOBE vector, a βAS3-FB vector, a V5 vector, a V5m3 vector, a V5m3-400 vector, a G9 vector, and a BCL11A shmir vector, see e.g., U.S. Patent Pub. No. 20150307867; Arumugam and Malik, *Hematology Am Soc Hematol Educ Program.* 2010; 2010 (1):445-50; Hoban et al., *Blood.* 2016 127:839-848; Scott and DeFrancesco, *Nature Biotechnology* 34, 600-607 (2016); Finotti et al., *Journal of Blood Medicine.* 2015:6 69-85; Pestina et al.,*Molecular Therapy.* 2009; 17(2): 245-252, each of which is incorporated here by reference in their entireties, and in particular embodiments, the vector details disclosed and referenced therein.

The skilled artisan would appreciate that many other different embodiments can be fashioned from the existing embodiments of the invention, such that the therapeutic transgene or gene of interest is expressed in a target cell type or cell lineage other than the hematopoietic lineage, e.g., the neuronal lineage.

E. Compositions and Formulations

The formulations and compositions contemplated herein may comprise a combination of any number of transduced or non-transduced cells or a combination thereof, viral vectors, polypeptides, polynucleotides, and one or more agents that increase transduction efficiency and/or VCN, e.g., poloxamers, agents that increase prostaglandin signaling, staurosporine, polycationic polymers, and polycationic peptides, as described herein, formulated in pharmaceutically-acceptable or physiologically-acceptable solutions (e.g., culture medium) for administration to a cell, tissue, organ, or an animal, either alone, or in combination with one or more other modalities of therapy. Compositions include, without limitation, cultures contemplated herein, and in particular embodiments, the terms composition and culture may be used synonymously.

Particular ex vivo and in vitro formulations and compositions contemplated herein may comprise a combination of transduced or non-transduced cells or a combination thereof, viral vectors, and one or more agents that increase transduction efficiency and/or VCN, e.g., poloxamers, agents that increase prostaglandin signaling, staurosporine, polycationic polymers, and polycationic peptides, as described herein, formulated in pharmaceutically-acceptable or physiologically-acceptable solutions (e.g., culture medium) for administration to a cell, tissue, organ, or an animal, either alone, or in combination with one or more other modalities of therapy.

Particular in vivo formulations and compositions contemplated herein may comprise a combination of viral vectors, and one or more agents that increase transduction efficiency and/or VCN, e.g., poloxamers, agents that increase prostaglandin signaling, staurosporine, polycationic polymers, and polycationic peptides, as described herein, formulated in pharmaceutically-acceptable or physiologically-acceptable solutions (e.g., culture medium) for administration to a cell, tissue, organ, or an animal, either alone, or in combination with one or more other modalities of therapy.

In certain embodiments, compositions contemplated herein comprise a population of cells comprising a therapeutically-effective amount of transduced cells, as described herein, formulated together with one or more pharmaceutically acceptable carriers (additives) and/or diluents (e.g., pharmaceutically acceptable cell culture medium).

In certain other embodiments, the present invention provides compositions comprising a retroviral vector and one or more agents that increase transduction efficiency and/or VCN, e.g., poloxamers, agents that increase prostaglandin signaling, staurosporine, polycationic polymers, and polycationic peptides, as described herein, formulated together with one or more pharmaceutically acceptable carriers (additives) and/or diluents (e.g., pharmaceutically acceptable cell culture medium).

In certain other embodiments, the present invention provides compositions comprising a retroviral vector and one or more poloxamers, e.g., poloxamer 338, poloxamer 407, formulated together with one or more pharmaceutically acceptable carriers (additives) and/or diluents (e.g., pharmaceutically acceptable cell culture medium).

In particular embodiments, compositions comprise a population of cells comprising stem or progenitor cells, a retroviral vector and one or more agents that increase transduction efficiency and/or VCN, e.g., poloxamers, agents that increase prostaglandin signaling, staurosporine, polycationic polymers, and polycationic peptides, as described herein, formulated together with one or more pharmaceutically acceptable carriers (additives) and/or diluents (e.g., pharmaceutically acceptable cell culture medium). In a related embodiment, the population of cells comprises hematopoietic stem and progenitor cells. In one embodiment, the population of cells comprises CD34$^+$ cells. In one embodiment, the population of cells are CD34$^+$ selected cells.

In preferred embodiments, the population of cells comprises CD34$^+$ cells that have one of the following β-globin alleles: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^1/\beta^1$, $\beta^C/\beta^C$, $\beta^E/\beta^S$, $\beta^0/\beta^S$, $\beta^C/\beta^S$, $\beta^1/\beta^S$, or $\beta^S/\beta^S$.

In preferred embodiments, the population of cells comprises CD34$^+$ cells that have one of the following β-globin alleles: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In preferred embodiments, the population of cells comprises CD34$^+$ cells that have one of the following β-globin alleles: $\beta^E/\beta^S$, $\beta^0/\beta^S$, $\beta^C/\beta^S$, $\beta^+/\beta^S$ or $\beta^S/\beta^S$.

Pharmaceutical compositions contemplated herein comprise transduced cells produced according to methods described herein and a pharmaceutically acceptable carrier.

In other embodiments, pharmaceutical compositions comprise a retroviral vector and agents that increase transduction efficiency and/or VCN: poloxamers and agents that increase prostaglandin signaling or staurosporine, and optionally polycationic polymers, and polycationic peptides, as described herein.

In one embodiment, pharmaceutical compositions comprise a retroviral vector and poloxamers and agents that increase prostaglandin signaling, and optionally polycationic polymers, and polycationic peptides, as described herein.

In one embodiment, pharmaceutical compositions comprise a retroviral vector and poloxamers and staurosporine, and optionally polycationic polymers, and polycationic peptides, as described herein.

In one embodiment, pharmaceutical compositions comprise a retroviral vector and a poloxamer. In preferred embodiments, the poloxamer is poloxamer 288, poloxamer 335, poloxamer 338, or poloxamer 407.

The phrase "pharmaceutically acceptable" refers to molecular entities and compositions that do not produce an allergic or similar untoward reaction when administered to a human. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a carrier is suitable for parenteral administration, e.g., intravascular (intravenous or intraarterial), intraperitoneal or intramuscular administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified hematopoietic stem and/or progenitor cells and a pharmaceutically acceptable carrier, e.g., pharmaceutically acceptable cell culture medium. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers and/or diluents may be present in amounts sufficient to maintain a pH of the therapeutic composition of about 7. Alternatively, the therapeutic composition has a pH in a range from about 6.8 to about 7.4, e.g., 6.8, 6.9, 7.0, 7.1, 7.2, 7.3, and 7.4. In still another embodiment, the therapeutic composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the hematopoietic stem and/or progenitor cells are dispersed within an acceptable liquid medium or solution, e.g., saline or serum-free medium, in an intravenous (IV) bag or the like. Acceptable diluents include, but are not limited to water, Plasma-Lyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of cells, e.g., hematopoietic stem and progenitor cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In a preferred embodiment, the compositions comprising hematopoietic stem and/or progenitor cells are formulated in PlasmaLyte.

In various embodiments, compositions comprising hematopoietic stem and/or progenitor cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of mycoplasma, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contains about 0.5 EU/mL to about 5.0

EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of viral vector systems (i.e., viral-mediated transduction) are contemplated including, but not limited to, retroviral (e.g., lentiviral) vectors.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, compositions contemplated herein may comprise one or more polypeptides, polynucleotides, vectors comprising same, agents that increase transduction efficiency and/or VCN, as described herein, and transduced cells, etc., formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules or various pharmaceutically-active agents. There is virtually no limit to other components that may also be included in the compositions in particular embodiments, provided that the additional agents do not adversely affect the ability of the composition to deliver the intended gene therapy.

In particular embodiments, formulation of pharmaceutically-acceptable excipients and carrier solutions is well-known to those of skill in the art, as is the development of suitable dosing and treatment regimens for using the particular compositions described herein in a variety of treatment regimens, including e.g., enteral and parenteral, e.g., intravascular, intravenous, intraarterial, intraosseously, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, 20th Edition. Baltimore, MD: Lippincott Williams & Wilkins, 2005, which is incorporated by reference herein, in its entirety.

F. Cell Culture Compositions

As discussed herein throughout, in particular embodiments, compositions and methods contemplated herein are useful for ex vivo and in vivo cell-based gene therapies. In particular embodiments, compositions may comprise cells in culture, i.e., a cell culture composition. A cell culture composition may comprise a population of cells comprising hematopoietic stem or progenitor cells, a suitable cell culture medium, and one or more poloxamers. A cell culture composition may comprise a population of cells comprising hematopoietic stem or progenitor cells, a suitable cell culture medium, one or more poloxamers, one or more agents that increase prostaglandin signaling or staurosporine, and optionally one or more polycationic polymers.

In particular embodiments, cultured cells are hematopoietic stem or progenitor cells or CD34+ cells.

In particular embodiments, cultured cells are hematopoietic stem or progenitor cells or CD34$^+$ cells that have the following β-globin alleles: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In particular embodiments, cultured cells are hematopoietic stem or progenitor cells or CD34$^+$ cells that have the following β-globin alleles: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In particular embodiments, cultured cells are hematopoietic stem or progenitor cells or CD34$^+$ cells that have the following β-globin alleles: $\beta^E/\beta^S$, $\beta^0/\beta^S$, $\beta^C/\beta^S$, $\beta^+/\beta^S$ or $\beta^S/\beta^S$.

In one embodiment, a cell culture composition comprises a population of cells comprising hematopoietic stem or progenitor cells, a cell culture medium suitable for human administration, and a poloxamer. In one embodiment, a cell culture composition comprises a population of cells comprising hematopoietic stem or progenitor cells, a cell culture medium suitable for human administration, a poloxamer and an agent that increases prostaglandin signaling, and optionally one or more polycationic polymers.

In one embodiment, a cell culture composition comprises a population of cells comprising genetically modified hematopoietic stem or progenitor cells, a cell culture medium suitable for administration to a human, and a poloxamer.

In one embodiment, a cell culture composition comprises a population of cells comprising genetically modified hematopoietic stem or progenitor cells, a cell culture medium suitable for administration to a human, a poloxamer and staurosporine, and optionally one or more polycationic polymers.

In some embodiments, the cell culture medium is a pharmaceutically acceptable cell culture medium.

Cell culture compositions contemplated herein, that comprise transduced hematopoietic stem or progenitor cells, can be administered systemically or by directed injection to a subject in need thereof in order to effect the desired gene therapy.

G. Transduction Methods

Methods and compositions contemplated herein significantly increase the transduction efficiency (TE) and vector copy number (VCN) of target cells. Without wishing to be bound to any particular theory, it is contemplated that the compositions and methods contemplated herein may be used to increase the VCN and transduce significantly more cells with significantly less virus, thereby minimizing the risk of genomic alteration and/or insertional activation of proto-oncogenes in the genome of the therapeutic cell, while simultaneously increasing the therapeutic efficacy of the drug product produced. Thus, the compositions and methods contemplated herein not only lead to production of a safer gene therapy, but to a more robust and therapeutically efficacious drug product. In addition, more efficient transduction allows less virus to be used per transduction and thus, decreases the cost of goods for lentiviral gene therapy.

The delivery of a gene(s) or other polynucleotide sequences using a retroviral or lentiviral vector by means of viral infection rather than by transfection is referred to as transduction. In one embodiment, retroviral vectors are transduced into a cell through infection and provirus integration. In certain embodiments, a cell, e.g., a target cell, is transduced if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

In particular embodiments, host cells or target cells transduced with a viral vector express a therapeutic polypeptide and are administered to a subject to treat and/or prevent a disease, disorder, or condition.

The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113.

In particular embodiments, HIV type 1 (HIV-1) based viral particles may be generated by co-expressing the virion packaging elements and the transfer vector in a producer cell. These cells may be transiently transfected with a number of plasmids. Typically from three to five plasmids are employed, but the number may be greater depending upon the degree to which the lentiviral components are broken up into separate units. For example, one plasmid may encode the core and enzymatic components of the virion, derived from HIV-1. This plasmid is termed the packaging plasmid. Another plasmid typically encodes the envelope protein(s), most commonly the G protein of vesicular stomatitis virus (VSV G) because of its high stability and broad tropism. This plasmid may be termed the envelope expression plasmid. Yet another plasmid encodes the genome to be transferred to the target cell, that is, the vector itself, and is called the transfer vector. The packaging plasmids can be introduced into human cell lines by known techniques, including calcium phosphate transfection, lipofection or electroporation. Recombinant viruses with titers of several millions of transducing units per milliliter (TU/mL) can be generated by this technique and variants thereof. After ultracentrifugation concentrated stocks of about $10^8$ TU/mL, $10^9$ TU/mL, $10^{10}$ TU/mL, $10^{11}$ TU/mL, $10^{12}$ TU/mL, or about $10^{13}$ TU/mL can be obtained.

Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art, e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

Viruses may be used to infect cells in vivo, ex vivo, or in vitro using techniques well known in the art. For example, when cells, for instance mobilized peripheral blood cells, bone marrow cells, CD34$^+$ cells, or hematopoietic stem or progenitor cells are transduced ex vivo, the vector particles may be incubated with the cells using a dose generally in the order of between 1 to 50 multiplicities of infection (MOI) which also corresponds to $1\times10^5$ to $50\times10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, and 50 MOI and all integer values in between.

In particular embodiments, lentiviral vector is used at an MOI of about 10 to about 25 to transduce a population of cells.

In particular embodiments, lentiviral vector is used at an MOI of about 10 to about 20 to transduce a population of cells.

In some embodiments, lentiviral vector is used at an MOI of about 10, about 11, about 12, about 13, about 14, about 15, about 16, about 17, about 18, about 19, about 20, about 21, about 22, about 23, about 24, about 25, about 26, about 27, about 28, about 29 or about 30 to transduce a population of cells.

Viruses may also be delivered to a subject in vivo, by direct injection to the cell, tissue, or organ in need of therapy. Direct injection requires on the order of between 1 to 100 multiplicities of infection (MOI) which also corresponds to $1\times10^5$ to $100\times10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, 50, 55, 50, 65, 70, 75, 80, 85, 90, 95, and 100 MOI and all integer values in between.

Viruses may also be delivered according to viral titer (TU/mL), which can be measured, for example, by using a commercially available p24 titer assay, which is an ELISA against the p24 viral coat protein. The following formula can be used to calculate the pg/mL of p24: there are approximately 2000 molecules of p24 per physical particle (PP) of lentivirus: $(2\times10^3)\times(24\times10^3$ Da of p24 per PP), $48\times10^6$/Avogadro=$(48\times10^6)/(6\times10^{23})$=$8\times10^{-17}$ g of p24 per PP, approximately 1 PP per $1\times10^{-16}$ g of p24, $1\times10^4$ PP per pg of p24. A reasonably well packaged, VSV-G pseudotyped lentiviral vector will have an infectivity index in the range of 1 TU per 1000 physical particles (PP) to 1 TU per 100 PP (or less). Thus, the range is approximately 10 to 100 TU/pg of p24. It is through this conversion that TU/mL is obtained.

Based on previous experience, the amount of lentivirus directly injected is determined by total TU and can vary based on both the volume that could be feasibly injected to the site and the type of tissue to be injected. For example, a bone marrow injection site may only allow for a very small volume of virus to be injected, so a high titer prep would be preferred, a TU of about $1\times10^6$ to $1\times10^7$, about $1\times10^6$ to $1\times10^8$, $1\times10^6$ to $1\times10^9$, about $1\times10^7$ to $1\times10^{10}$, $1\times10^8$ to $1\times10^{11}$, about $1\times10^8$ to $1\times10^{12}$, or about $1\times10^{10}$ to $1\times10^{12}$ or more per injection could be used. However, a systemic delivery could accommodate a much larger TU, a load of $1\times10^8$, $1\times10^9$, $1\times10^{10}$, $1\times10^{11}$, $1\times10^{12}$, $1\times10^{13}$, $1\times10^{14}$, or $1\times10^{15}$, could be delivered.

Compositions and methods contemplated herein provide high transduction efficiency and VCN of hematopoietic cells in vitro, ex vivo, and in vivo, using lower viral titers than those disclosed above to achieve comparable transduction efficiencies in the absence of the compositions and methods provided herein.

Certain embodiments contemplated herein arise from the unexpected finding that transduction efficiency and/or VCN is significantly increased by contacting hematopoietic cells, in vitro, ex vivo, or in vivo, with a retrovirus and a poloxamer or a poloxamer and one or more agents that stimulate the prostaglandin EP receptor signaling pathway (see e.g., WO 2007/112084 and WO2010/108028), and optionally a polycationic polymer.

In various embodiments, the poloxamer has an average molecular weight of polypropylene subunits greater than about 2250 Daltons.

In particular embodiments, the poloxamer has an average molecular weight of polypropylene subunits of at least about 2750 Daltons.

In particular embodiments, the poloxamer has an average molecular weight of polypropylene subunits of at least about 3250 Daltons.

In particular embodiments, the poloxamer has an average molecular weight of polypropylene subunits of at least about 4000 Daltons.

In various embodiments, the poloxamer comprises at least about 40% polyethylene oxide.

In particular embodiments, the poloxamer comprises at least about 50% polyethylene oxide.

In particular embodiments, the poloxamer comprises at least about 60% polyethylene oxide.

In particular embodiments, the poloxamer comprises at least about 70% polyethylene oxide.

In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide.

In particular embodiments, the poloxamer has an average molecular weight of polypropylene subunits of at least about 2750 Daltons and the poloxamer comprises at least about 50% polyethylene oxide.

In particular embodiments, the poloxamer has an average molecular weight of polypropylene subunits of at least about 3250 Daltons and the poloxamer comprises at least about 50% polyethylene oxide.

In certain embodiments, the poloxamer is selected from the group consisting of: poloxamer 288, poloxamer 335, poloxamer 338, and poloxamer 407.

In one embodiment, the poloxamer is poloxamer 288.
In one embodiment, the poloxamer is poloxamer 335.
In one embodiment, the poloxamer is poloxamer 338.
In one embodiment, the poloxamer is poloxamer 407.

Illustrative final poloxamer concentrations used to transduced hematopoietic cells include, but are not limited to about 10 μg/mL to about 5000 μg/mL, about 10 μg/mL to about 2500 μg/mL, about 10 μg/mL to about 1000 μg/mL, about 50 μg/mL to about 1000 μg/mL, about 100 μg/mL to about 1000 μg/mL, about 200 μg/mL to about 1000 μg/mL, about 200 μg/mL to about 500 μg/mL, or about 10 μg/mL, about 20 μg/mL, about 30 μg/mL, about 40 μg/mL, about 50 μg/mL, about 60 μg/mL, about 70 μg/mL, about 80 μg/mL, about 90 μg/mL, about 100 μg/mL, about 200 μg/mL, about 300 μg/mL, about 400 μg/mL, about 500 μg/mL, about 600 μg/mL, about 700 μg/mL, about 800 μg/mL, about 900 μg/mL, about 1000 μg/mL, about 1250 μg/mL, about 1500 μg/mL, about 1750 μg/mL, about 2000 μg/mL, about 2500 μg/mL, or about 5000 μg/mL or more, and any intervening concentration thereof.

In one embodiment, the agent is a prostaglandin EP receptor ligand including, but not limited to, prostaglandin $E_2$ ($PGE_2$), as well as "analogs" or "derivatives" thereof.

In one embodiment, the agent that stimulates the prostaglandin EP receptor signaling pathway is $PGE_2$.

Illustrative final prostaglandin EP receptor signaling pathway agonist concentrations used to transduce hematopoietic cells include, but are not limited to about 10 μM to about 200 μM, about 10 μM to about 100 μM, about 50 μM to about 100 μM, or about 10 μM, about 20 μM, about 30 μM, about 40 μM, about 50 μM, about 60 μM, about 70 μM, about 80 μM, about 90 μM, or about 100 μM or more, and any intervening concentration thereof.

In one embodiment, the polycationic polymer is protamine sulfate or polybrene.

In one embodiment, the polycationic polymer is protamine sulfate. Protamine sulfate or polybrene can be used at a final concentration of about 5 μg/mL to about 15 μg/mL, about 5 μg/mL to about 10 μg/mL, or about 5 μg/mL, about 6 μg/mL, about 7 μg/mL, about 8 μg/mL, about 9 μg/mL, about 10 μg/mL, about 11 μg/mL, about 12 μg/mL, about 13 μg/mL, about 14 μg/mL or about 15 μg/mL or more.

In another embodiment, transduction efficiency and/or VCN is significantly increased by contacting cells, in vitro, ex vivo, or in vivo, with a retrovirus and a poloxamer and staurosporine, and optionally a polycationic polymer.

Illustrative final staurosporine concentrations used to transduced hematopoietic cells include, but are not limited to about 100 nM to about 1000 nM, about 110 nM to about 800 nM, about 200 nM to about 800 nM, about 400 nM to about 800 nM, about 200 nM to about 400 nM, about 200 nM to about 500 nM, or about 100 nM, about 200 nM, about 300 nM, about 400 nM, about 500 nM, about 600 nM, about 700 nM, about 800 nM, about 900 nM, or about 1000 nM or more, and any intervening concentration thereof.

In particular embodiments, hematopoietic cells may be cultured in the presence of a retrovirus may be exposed to (contacted with) a poloxamer and one or more agents that stimulates the prostaglandin EP receptor signaling pathway or staurosporine, and optionally a polycationic polymer, for a duration of about 10 minutes to about 72 hours, about 30 minutes to about 72 hours, about 30 minutes to about 48 hours, about 30 minutes to about 24 hours, about 30 minutes to about 12 hours, about 30 minutes to about 8 hours, about 30 minutes to about 6 hours, about 30 minutes to about 4 hours, about 30 minutes to about 2 hours, or about 1 hour to about 2 hours.

In particular embodiments, hematopoietic cells may be cultured in the presence of a retrovirus may be exposed to (contacted with) a poloxamer or a poloxamer and one or more agents that stimulates the prostaglandin EP receptor signaling pathway or staurosporine, and optionally a polycationic polymer, for a duration of about 10 minutes, about 30 minutes, about 1 hour, about 2 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, or about 72 hours, or any intervening duration of time.

In another embodiment, hematopoietic cells may be cultured with a retrovirus prior to culture with one or more agents that increases transduction efficiency and/or VCN, during culture with one or more agents that increases transduction efficiency and/or VCN, or after culture with one or more agents that increases transduction efficiency and/or VCN for any of the foregoing periods of time disclosed herein.

In certain embodiments, it is contemplated that hematopoietic cells may be cultured with a poloxamer or a poloxamer and one or more agents that stimulates the prostaglandin EP receptor signaling pathway or staurosporine, and optionally a polycationic polymer prior to culture with a retrovirus, during culture with a retrovirus, or after culture with a retrovirus, or any combination thereof for any of the foregoing periods of time disclosed herein.

In one embodiment, hematopoietic cells are contacted with a retrovirus and at the same time, with a poloxamer or a poloxamer and one or more agents that stimulates the prostaglandin EP receptor signaling pathway or staurosporine, and optionally a polycationic polymer for any of the foregoing periods of time disclosed herein.

Furthermore, one having ordinary skill in the art would appreciate that in particular embodiments transduction efficiency and VCN are increased by culturing hematopoietic cells with retrovirus and a poloxamer or a poloxamer and one or more agents that stimulates the prostaglandin EP receptor signaling pathway or staurosporine, and optionally a polycationic polymer, during the first 6 hours of transduction, the first 12 hours of transduction, the first 24 hours of transduction, the first 48 hours of transduction, or the first 72 hours of the transduction, or any intervening duration of transduction.

In certain embodiments, it is contemplated that hematopoietic cells may be cultured with staurosporine prior to culture with a retrovirus, washed, and contacted with a retrovirus and at the same time, with a poloxamer, and optionally a polycationic polymer for any of the foregoing periods of time disclosed herein.

In particular embodiments, hematopoietic cells are transduced in a vessel, such as a bag, e.g., blood bag, and are agitated during the transduction.

As disclosed throughout, the compositions and methods contemplated herein offer unexpected increases in transduction efficiency and VCN of hematopoietic cells, which are notoriously difficult to transduce and typically have low VCNs.

In various embodiments, the compositions and methods contemplated herein increase transduction efficiency to at least about 30%, at least about 40%, at least about 50%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, including any intervening percentages.

In various embodiments, the compositions and methods contemplated herein increase average VCN to at least about 0.5 to at least about 5.0, at least about 0.5 to at least about 3, at least about 0.5 to at least about 1.0, at least about 1.0 to at least about 5.0, at least about 1.0 to at least about 3.0, or at least about 0.5, at least about 1.0, at least about 1.5, at least about 2.0, at least about 2.5, at least about 3.0, at least about 3.5, at least about 4.0, at least about 4.5, or at least about 5.0.

In various embodiments, hematopoietic cells transduced with the compositions and methods contemplated herein have a transduction efficiency of at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% and an average VCN of at least about 0.5, at least about 1.0, at least about 1.5, at least about 2.0, or at least about 2.5.

In particular embodiments, an increase in transduction efficiency represents at least 2-fold, at least 5-fold, at least 10-fold, at least 25-fold, at least 50-fold, or at least 100-fold, or more fold enrichment of hematopoietic cells transduced with the compositions and methods contemplated herein compared to hematopoietic cells transduced with vector alone.

In particular embodiments, increase in average VCN represents at least 2-fold, at least 5-fold, at least 10-fold, at least 25-fold, at least 50-fold, or at least 100-fold, or more fold enrichment in VCN of hematopoietic cells transduced with the compositions and methods contemplated herein compared to hematopoietic cells transduced with vector alone.

Following transduction, the transduced cells may be cultured under conditions suitable for their maintenance, growth or proliferation. In particular embodiments, the transduced cells are cultured for about 1, 2, 3, 4, 5, 6, 7, 8, 9, 10, 11, 12, 13 or 14 days before transplantation.

Prior to, during and/or following transduction, the cells may be cultured under conditions that promote the expansion of stem cells or progenitor cells. Any method known in the art may be used. In certain embodiments, prior to, during or following transduction, the cells are cultured in the presence of one or more growth factors that promote the expansion of stem cells or progenitor cells. Examples of growth factors that promote the expansion of stem cells or progenitor cells include, but are not limited to, fetal liver tyrosine kinase (Flt3) ligand, stem cell factor, and interleukins 6 and 11, which have been demonstrated to promote self-renewal of murine hematopoietic stem cells. Others include Sonic hedgehog, which induces the proliferation of primitive hematopoietic progenitors by activation of bone morphogenetic protein 4, Wnt3a, which stimulates self-renewal of HSCs, brain derived neurotrophic factor (BDNF), epidermal growth factor (EGF), fibroblast growth factor (FGF), ciliary neurotrophic factor (CNF), transforming growth factor-β (TGF-β), a fibroblast growth factor (FGF, e.g., basic FGF, acidic FGF, FGF-17, FGF-4, FGF-5, FGF-6, FGF-8b, FGF-8c, FGF-9), granulocyte colony stimulating factor (GCSF), a platelet derived growth factor (PDGF, e.g., PDGFAA, PDGFAB, PDGFBB), granulocyte macrophage colony stimulating factor (GMCSF), stem cell factor (SCF), stromal cell derived factor (SCDF), insulin like growth factor (IGF), thrombopoietin (TPO) or interleukin-3 (IL-3). In particular embodiments, before, during or following transduction, the cells are cultured in the presence of one or more growth factors that promote expansion of stem cells or progenitor cells.

The compositions and methods contemplated herein, in particular embodiments, are applicable to the transduction of any cell type. Cells suitable for use with the compositions and methods contemplated herein may be obtained from any animal, preferably a mammal, e.g., a non-human primate or human, and more preferably a human, and they may be transplanted into any animal, preferably a mammal, and more preferably a human.

Certain embodiments contemplate isolation and transduction of a population of cells. As used herein, the term "population of cells" refers to a plurality of cells that may be made up of any number and/or combination of homogenous or heterogeneous cell types, as described elsewhere herein. For example, for transduction of hematopoietic stem or progenitor cells, a population of cells may be isolated or obtained from umbilical cord blood, placental blood, bone marrow, or peripheral blood. A population of cells may comprise about 10%, about 20%, about 30%, about 40%, about 50%, about 60%, about 70%, about 80%, about 90%, or about 100% of the target cell type to be transduced. In certain embodiments, hematopoietic stem or progenitor cells may be isolated or purified from a population of heterogeneous cells using methods known in the art.

Preferred target cell types transduced with the compositions and methods contemplated herein include, hematopoietic cells, e.g., human hematopoietic cells.

In preferred embodiments, the compositions and methods contemplated herein are used to increase the transduction efficiency and/or VCN of hematopoietic stem or progenitor cells.

Illustrative sources to obtain hematopoietic cells transduced with the methods and compositions contemplated herein include, but are not limited to: cord blood, bone marrow or mobilized peripheral blood.

Illustrative examples of hematopoietic cells suitable for transduction with the methods and compositions contemplated herein include $CD34^+$ cells. The term "$CD34^+$ cell," as used herein refers to a cell expressing the CD34 protein on its cell surface. "CD34," as used herein refers to a cell surface glycoprotein (e.g., sialomucin protein) that often acts as a cell-cell adhesion factor. CD34$^+$ is a cell surface marker of both hematopoietic stem and progenitor cells.

Additional illustrative examples of hematopoietic stem or progenitor cells suitable for transduction with the methods and compositions contemplated herein include hematopoietic cells that are CD34$^+$CD38$^{Lo}$CD90$^+$CD45$^{RA-}$, hematopoietic cells that are CD34$^+$, CD59$^+$, Thy1/CD90$^+$, CD38$^{Lo/-}$, C-kit/CD117$^+$, and Lin$^{(-)}$, and hematopoietic cells that are CD133$^+$.

Various methods exist to characterize hematopoietic hierarchy. One method of characterization is the SLAM code. The SLAM (Signaling lymphocyte activation molecule) family is a group of >10 molecules whose genes are located mostly tandemly in a single locus on chromosome 1 (mouse), all belonging to a subset of immunoglobulin gene superfamily, and originally thought to be involved in T-cell stimulation. This family includes CD48, CD150, CD244, etc., CD150 being the founding member, and, thus, also called slamF1, i.e., SLAM family member 1. The signature SLAM code for the hematopoietic hierarchy is hematopoietic stem cells (HSC)—CD150$^+$CD48$^-$CD244$^-$; multipotent progenitor cells (MPPs)—CD150$^-$CD48$^-$CD244$^+$; lineage-restricted progenitor cells (LRPs)—CD150$^-$CD48$^+$CD244$^+$; common myeloid progenitor (CMP)—lin$^-$SCA-1-c-kit$^+$CD34$^+$CD16/32$^{mid}$; granulocyte-macrophage progenitor (GMP)—lin$^-$SCA-1-c-kit$^+$CD34$^+$CD16/32$^{hi}$; and megakaryocyte-erythroid progenitor (MEP)—lin$^-$SCA-1-c-kit$^+$CD34$^-$CD16/32$^{low}$.

In particular embodiments, CD34$^+$ cells that are transduced with the vectors and compositions contemplated herein have the following β-globin alleles: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$, In particular embodiments, CD34$^+$ cells that are transduced with the vectors and compositions contemplated herein have the following β-globin alleles: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In particular embodiments, CD34$^+$ cells that are transduced with the vectors and compositions contemplated herein have the following β-globin alleles: $\beta^E/\beta^S$, $\beta^0/\beta^S$, $\beta^C/\beta^S$, $\beta^+/\beta^S$ or $\beta^S/\beta^S$.

H. Gene Therapy Methods

Drug products comprising a higher proportion of transduced cells, wherein the copy number of the therapeutic genes in each cell is also higher provides for more therapeutically efficacious gene therapies. As used herein, the term "drug product" refers to genetically modified cells produced using the compositions and methods contemplated herein. In particular embodiments, the drug product comprises genetically modified hematopoietic stem or progenitor cells, e.g., CD34$^+$ cells. Without wishing to be bound to any particular theory, increasing the amount of a therapeutic gene in a drug product may allow treatment of subjects having no or minimal expression of the corresponding gene in vivo, thereby significantly expanding the opportunity to bring gene therapy to subjects for which gene therapy was not previously a viable treatment option.

The transduced cells and corresponding retroviral vectors contemplated herein provide improved methods of gene therapy. As used herein, the term "gene therapy" refers to the introduction of a gene into a cell's genome. In various embodiments, a viral vector of the invention comprises a hematopoietic expression control sequence that expresses a therapeutic transgene encoding a polypeptide that provides curative, preventative, or ameliorative benefits to a subject diagnosed with or that is suspected of having monogenic disease, disorder, or condition or a disease, disorder, or condition that is amenable to hematopoietic stem cell therapy.

In one preferred embodiment, transduced cells comprise the potential to develop into brain microglial cells (macrophages). In particular embodiments, hematopoietic stem cells are transduced with a vector contemplated herein and administered to an individual in need of therapy for a lysosomal storage disorder, an adrenoleukodystrophy or adrenomyeloneuropathy. Hematopoietic stem cells are the origin of brain microglial cells and thus, are preferred in such embodiments.

In particular embodiments, transduced hematopoietic stem or progenitor cells comprise viral vectors having a hematopoietic expression control sequence that expresses a therapeutic transgene encoding a polypeptide that provides curative, preventative, or ameliorative benefits to a subject diagnosed with or that is suspected of having monogenic disease, disorder, or condition or a disease, disorder, or condition of the hematopoietic system.

In certain embodiments, vectors, viral particles, and/or transduced cells contemplated herein are be used to treat, prevent, and/or ameliorate a monogenic disease, disorder, or condition or a disease, disorder, or condition of the hematopoietic system in a subject, e.g., a hemoglobinopathy.

Illustrative examples of monogenic disorders and their corresponding therapeutic gene(s) that are suitable for use in particular embodiments contemplated herein include, but are not limited to: X-SCID (IL2Rγ), ADA-SCID (adenosine deaminase), Batten's disease (tripeptidyl peptidase 1), Mucopolysaccharidosis type 1—Hurler Syndrome (alpha-L iduronidase), Mucopolysaccharidosis type 2—Hunter Syndrome (iduronate 2-sulfatase), Mucopolysaccharidosis type 3—Sanfilippo Syndrome (N-sulfoglucosamine sulfohydrolase), Mucopolysaccharidosis type 4A—Morquio A Syndrome (galactosamine-6 sulfatase), Mucopolysaccharidosis type 4B—Morquio B Syndrome (beta-galactosidase), Mucopolysaccharidosis type 6—Maroteaux-Lamy Syndrome (N-acetylgalactosamine-4-sulphatase), Gaucher disease (glucocerebrosidase), Metachromatic Leukodystrophy (arylsulfatase A), chronic granulomatous diseases (cytochrome b-245 alpha chain, cytochrome b-245 beta chain, neutrophil cytosolic factor 1, neutrophil cytosolic factor 2, neutrophil cytosolic factor 4), Wiskott Aldrich Syndrome (wiskott aldrich syndrome protein), perforin deficiency (PRF1), Fanconi Anemia (FANC genes, e.g., FANCA, FANCC, FANCG), X-linked lymphoproliferative syndrome (SH2D1A), RAG deficiency (RAG1/2), Artemis protein deficiency (DCLRE1C), Hemophilia A (Factor VIII), Hemophilia B (Factor IX), and Leukocyte adhesion deficiency (CD18).

As used herein, "hematopoiesis," refers to the formation and development of blood cells from progenitor cells as well as formation of progenitor cells from stem cells. Blood cells include but are not limited to erythrocytes or red blood cells (RBCs), reticulocytes, monocytes, neutrophils, megakaryocytes, eosinophils, basophils, B-cells, macrophages, granulocytes, mast cells, thrombocytes, and leukocytes.

As used herein, the term "hemoglobinopathy" or "hemoglobinopathic condition" refers to a diverse group of inherited blood disorders that involve the presence of abnormal hemoglobin molecules resulting from alterations in the structure and/or synthesis of hemoglobin. Normally, hemoglobin consists of four protein subunits: two subunits of β-globin and two subunits of a-globin. Each of these protein subunits is attached (bound) to an iron-containing molecule called heme; each heme contains an iron molecule in its center that can bind to one oxygen molecule. Hemoglobin within red blood cells binds to oxygen molecules in the lungs. These cells then travel through the bloodstream and deliver oxygen to tissues throughout the body.

Hemoglobin A (HbA) is the designation for the normal hemoglobin that exists after birth. Hemoglobin A is a tetramer with two alpha chains and two beta chains ($\alpha_2\beta_2$). Hemoglobin A2 is a minor component of the hemoglobin found in red cells after birth and consists of two alpha chains and two delta chains ($\alpha_2\beta_2$). Hemoglobin A2 generally comprises less than 3% of the total red cell hemoglobin. Hemoglobin F is the predominant hemoglobin during fetal development. The molecule is a tetramer of two alpha chains and two gamma chains ($\alpha_2\gamma_2$).

The most common hemoglobinopathies include sickle cell disease, $\beta$-thalassemia, and $\alpha$-thalassemia.

In particular embodiments, the compositions and methods contemplated herein provide gene therapy for subjects having a sickle cell disease. The term "sickle cell anemia" or "sickle cell disease" is defined herein to include any symptomatic anemic condition which results from sickling of red blood cells. Sickle cell anemia $\beta^S/\beta^S$, a common form of sickle cell disease (SCD), is caused by Hemoglobin S (HbS). HbS is generated by replacement of glutamic acid (E) with valine (V) at position 6 in $\beta$-globin, noted as Glu6Val or E6V. Replacing glutamic acid with valine causes the abnormal HbS subunits to stick together and form long, rigid molecules that bend red blood cells into a sickle (crescent) shape. The sickle-shaped cells die prematurely, which can lead to a shortage of red blood cells (anemia). In addition, the sickle-shaped cells are rigid and can block small blood vessels, causing severe pain and organ damage.

Additional mutations in the $\beta$-globin gene can also cause other abnormalities in $\beta$-globin, leading to other types of sickle cell disease. These abnormal forms of $\beta$-globin are often designated by letters of the alphabet or sometimes by a name. In these other types of sickle cell disease, one $\beta$-globin subunit is replaced with HbS and the other $\beta$-globin subunit is replaced with a different abnormal variant, such as hemoglobin C (HbC; $\beta$-globin allele noted as $\beta^C$) or hemoglobin E (HbE; $\beta$-globin allele noted as $\beta^E$).

In hemoglobin SC (HbSC) disease, the $\beta$-globin subunits are replaced by HbS and HbC. HbC results from a mutation in the $\beta$-globin gene and is the predominant hemoglobin found in people with HbC disease ($\alpha_2\beta^C_2$). HbC results when the amino acid lysine replaces the amino acid glutamic acid at position 6 in $\beta$-globin, noted as Glu6Lys or E6K. HbC disease is relatively benign, producing a mild hemolytic anemia and splenomegaly. The severity of HbSC disease is variable, but it can be as severe as sickle cell anemia.

HbE is caused when the amino acid glutamic acid is replaced with the amino acid lysine at position 26 in $\beta$-globin, noted as Glu26Lys or E26K. People with HbE disease have a mild hemolytic anemia and mild splenomegaly. HbE is extremely common in Southeast Asia and in some areas equals hemoglobin A in frequency. In some cases, the HbE mutation is present with HbS. In these cases, a person may have more severe signs and symptoms associated with sickle cell anemia, such as episodes of pain, anemia, and abnormal spleen function.

Other conditions, known as hemoglobin sickle-$\beta$-thalassemias (HbSBetaThal), are caused when mutations that produce hemoglobin S and $\beta$-thalassemia occur together. Mutations that combine sickle cell disease with beta-zero ($\beta^0$; gene mutations that prevent $\beta$-globin production) thalassemia lead to severe disease, while sickle cell disease combined with beta-plus ($\beta^+$: gene mutations that decrease $\beta$-globin production) thalassemia is milder.

As used herein, "thalassemia" refers to a hereditary disorder characterized by defective production of hemoglobin. Examples of thalassemias include $\alpha$- and $\beta$-thalassemia.

In particular embodiments, the compositions and methods contemplated herein provide gene therapy for subjects having a $\beta$-thalassemia. $\beta$-thalassemias are caused by a mutation in the $\beta$-globin chain, and can occur in a major or minor form. Nearly 400 mutations in the $\beta$-globin gene have been found to cause $\beta$-thalassemia. Most of the mutations involve a change in a single DNA building block (nucleotide) within or near the $\beta$-globin gene. Other mutations insert or delete a small number of nucleotides in the $\beta$-globin gene. As noted above, $\beta$-globin gene mutations that decrease $\beta$-globin production result in a type of the condition called beta-plus ($\beta^+$) thalassemia. Mutations that prevent cells from producing any beta-globin result in beta-zero ($\beta^0$) thalassemia. In the major form of $\beta$-thalassemia, children are normal at birth, but develop anemia during the first year of life. The minor form of $\beta$-thalassemia produces small red blood cells. Thalassemia minor occurs if you receive the defective gene from only one parent. Persons with this form of the disorder are carriers of the disease and usually do not have symptoms.

HbE/$\beta$-thalassemia results from combination of HbE and $\beta$-thalassemia ($\beta^E/\beta^0$, $\beta^E/\beta^+$) and produces a condition more severe than is seen with either HbE trait or $\beta$-thalassemia trait. The disorder manifests as a moderately severe thalassemia that falls into the category of thalassemia intermedia. HbE/$\beta$-thalassemia is most common in people of Southeast Asian background.

In particular embodiments, the compositions and methods contemplated herein provide gene therapy for subjects having an $\alpha$-thalassemia. $\alpha$-thalassemia is a fairly common blood disorder worldwide. Thousands of infants with Hb Bart syndrome and HbH disease are born each year, particularly in Southeast Asia. A-thalassemia also occurs frequently in people from Mediterranean countries, North Africa, the Middle East, India, and Central Asia. a-thalassemia typically results from deletions involving the HBA1 and HBA2 genes. Both of these genes provide instructions for making a protein called $\alpha$-globin, which is a component (subunit) of hemoglobin. People have two copies of the HBA1 gene and two copies of the HBA2 gene in each cell. The different types of a-thalassemia result from the loss of some or all of the HBA1 and HBA2 alleles.

Hb Bart syndrome, the most severe form of $\alpha$-thalassemia, results from the loss of all four alpha-globin alleles. HbH disease is caused by a loss of three of the four $\alpha$-globin alleles. In these two conditions, a shortage of $\alpha$-globin prevents cells from making normal hemoglobin. Instead, cells produce abnormal forms of hemoglobin called hemoglobin Bart (Hb Bart) or hemoglobin H (HbH). These abnormal hemoglobin molecules cannot effectively carry oxygen to the body's tissues. The substitution of Hb Bart or HbH for normal hemoglobin causes anemia and the other serious health problems associated with $\alpha$-thalassemia.

Two additional variants of a-thalassemia are related to a reduced amount of $\alpha$-globin. Because cells still produce some normal hemoglobin, these variants tend to cause few or no health problems. A loss of two of the four a-globin alleles results in $\alpha$-thalassemia trait. People with $\alpha$-thalassemia trait may have unusually small, pale red blood cells and mild anemia. A loss of one a-globin allele is found in $\alpha$-thalassemia silent carriers. These individuals typically have no thalassemia-related signs or symptoms. In a preferred embodiment, gene therapy methods contemplated herein are used to treat, prevent, or ameliorate a hemoglobinopathy is selected from the group consisting of: hemoglobin C disease, hemoglobin E disease, sickle cell anemia, sickle cell disease (SCD), thalassemia, β-thalassemia, thalassemia major, thalassemia intermedia, a-thalassemia, hemoglobin Bart syndrome and hemoglobin H disease. In a preferred embodiment, gene therapy methods contemplated herein are used to treat, prevent, or ameliorate a hemoglobinopathy in a subject having a β-globin genotype selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In various embodiments, the retroviral vectors are administered by direct injection to a cell, tissue, or organ of a subject in need of gene therapy, in vivo. In various other embodiments, cells are transduced in vitro or ex vivo with vectors contemplated herein, and optionally expanded ex vivo. The transduced cells are then administered to a subject in need of gene therapy.

Cells suitable for transduction and administration in the gene therapy methods contemplated herein include, but are not limited to stem cells, progenitor cells, and differentiated cells as described elsewhere herein. In certain embodiments, the transduced cells are hematopoietic stem or progenitor cells as described elsewhere herein.

Preferred cells for use in the gene therapy compositions and methods contemplated herein include autologous/autogeneic ("self") cells.

In particular embodiments, the cells used as the source for gene therapy have the following β-globin alleles: $\beta^E/\beta^0$, $\beta^C/\beta^0$, $\beta^0/\beta^0$, $\beta^E/\beta^E$, $\beta^C/\beta^1$, $\beta^E/\beta^1$, $\beta^0/\beta^1$, $\beta^1/\beta^1$, $\beta^C/\beta^C$, $\beta^E/\beta^S$, $\beta^0/\beta^S$, $\beta^C/\beta^S$, $\beta^+/\beta^S$ or $\beta^S/\beta^S$.

In particular embodiments, the cells used as the source for gene therapy have the following β-globin alleles: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In particular embodiments, the cells used as the source for gene therapy have the following β-globin alleles: $\beta^E/\beta^S$, $\beta^0/\beta^S$, $\beta^C/\beta^S$, $\beta^+/\beta^S$ or $\beta^S/\beta^S$.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods disclosed elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the term "amount" refers to "an amount effective" or "an effective amount" of a virus or transduced therapeutic cell to achieve a beneficial or desired prophylactic or therapeutic result, including clinical results.

A "prophylactically effective amount" refers to an amount of a virus or transduced therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a virus or transduced therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

Without wishing to be bound to any particular theory, an important advantage provided by the vectors, compositions, and methods of the present invention is the high efficacy of gene therapy that can be achieved by administering populations of cells comprising high percentages of transduced cells compared to existing methods.

The transduced cells may be administered as part of a bone marrow or cord blood transplant in an individual that has or has not undergone bone marrow ablative therapy. In one embodiment, transduced cells of the invention are administered in a bone marrow transplant to an individual that has undergone chemoablative or radioablative bone marrow therapy.

In one embodiment, a dose of transduced cells is delivered to a subject intravenously. In preferred embodiments, transduced hematopoietic stem cells are intravenously administered to a subject.

In one illustrative embodiment, the effective amount of transduced cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of transduced cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of transduced cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about 7×10⁶ cells/kg, 2×10⁶ cells/kg to about 8×10⁶ cells/kg, 3×10⁶ cells/kg to about 6×10⁶ cells/kg, 3×10⁶ cells/kg to about 7×10⁶ cells/kg, 3×10⁶ cells/kg to about 8×10⁶ cells/kg, 4×10⁶ cells/kg to about 6×10⁶ cells/kg, 4×10⁶ cells/kg to about 7×10⁶ cells/kg, 4×10⁶ cells/kg to about 8×10⁶ cells/kg, 5×10⁶ cells/kg to about 6×10⁶ cells/kg, 5×10⁶ cells/kg to about 7×10⁶ cells/kg, 5×10⁶ cells/kg to about 8×10⁶ cells/kg, or 6×10⁶ cells/kg to about 8×10⁶ cells/kg, including all intervening doses of cells.

Some variation in dosage will necessarily occur depending on the condition of the subject being treated. The person responsible for administration will, in any event, determine the appropriate dose for the individual subject.

In various embodiments, the vectors, compositions, and methods contemplated herein offer improved methods of gene therapy using ex vivo gene therapy and autologous transplantation. In one preferred embodiment, transduced cells, such as stem or progenitor cells, e.g., hematopoietic stem or progenitor cells, or CD34⁺ cells. In particular embodiments, hematopoietic stem or progenitor cells are transduced with a vector contemplated herein in the presence of one or more agents that increases retroviral, e.g., lentiviral transduction efficiency and VCN, and the transduced cells are administered to an individual in need of therapy for a hemoglobinopathy.

In particular embodiments, hematopoietic stem or progenitor cells are transduced with a vector contemplated herein in the presence of one or more agents that increases retroviral, e.g., lentiviral transduction efficiency and VCN, and the transduced cells are administered to an individual in need of therapy for an adrenoleukodystrophy or an adrenomyeloneuropathy.

In particular embodiments, hematopoietic stem or progenitor cells are transduced with a vector contemplated herein in the presence of one or more agents that increases retroviral, e.g., lentiviral transduction efficiency and VCN, and the transduced cells are administered to an individual in need of therapy for ADA-SCID, X-SCID, Batten's Disease, MPSI, or MPSII.

In one preferred embodiment, viral vector systems are introduced into hematopoietic stem or progenitor cells in order to express high levels of one or more therapeutic proteins in erythroid cells or erythroid precursor cells. Retroviral vectors, including lentiviral vectors contemplated herein comprise a polynucleotide-of-interest, including, for example, a globin gene or a gene which encodes an antisickling protein. In one embodiment, the globin gene expressed in the retroviral vector of the invention is β-globin, δ-globin, or γ-globin. In another embodiment, the human β-globin gene is the wild type human β-globin gene or human β$^A$-globin gene. In another embodiment, the human β-globin gene comprises one or more deletions of intron sequences or is a mutated human β-globin gene encoding at least one antisickling amino acid residue. Antisickling amino acids can be derived from human δ-globin or human γ-globin. In another embodiment, the mutated human β-globin gene encodes a threonine to glutamine mutation at codon 87 ($β^{A-T87Q}$).

In another embodiment, the mutated human β-globin gene encodes one or more of, or all of, the following mutations: a threonine to glutamine mutation at codon 87 ($β^{A-T87Q}$), a lysine to glutamate mutation at codon 120 ($β^{A-K120E}$), and a lysine to glutamate mutation at codon 95 ($β^{A-K95E}$).

In another embodiment, the mutated human β-globin gene encodes one or more of, or all of, the following mutations: a threonine to glutamine mutation at codon 87 ($β^{A-T87Q}$), a glycine to aspartate mutation at codon 16 ($β^{A-G16D}$), and a glutamate to alanine mutation at codon 22 ($β^{A-E22A}$).

In another preferred embodiment, hematopoietic stem or progenitor cells transduced with the methods and compositions contemplated herein to yield drug products used in gene therapy, including gene therapy for the treatment of hemoglobinopathies. In particular embodiments, drug products generated produce sufficiently stable levels of gene expression in erythroid cells, e.g., in order to treat erythroid-specific diseases. In a particular embodiment, the drug products are used to treat hemoglobinopathies, including, for example, sickle cell disease (SCD). In another preferred embodiment, the drug products are used for treatment of thalassemias, including, but not limited to, β-thalassemia.

In another preferred embodiment, hematopoietic stem or progenitor cells transduced with the methods and compositions contemplated herein to yield drug products that express sufficiently stable levels of ABCD1 for treatment of adrenoleukodystrophies and/or adrenomyeloneuropathies.

In another embodiment, hematopoietic stem or progenitor cells transduced with the methods and compositions contemplated herein to yield drug products that express sufficiently stable levels of adenosine deaminase to treat ADA-SCID; sufficiently stable levels of interleukin 2 receptor gamma to treat X-SCID; sufficiently stable levels of tripeptidyl peptidase 1 to treat Batten's disease; sufficiently stable levels of alpha-L iduronidase to treat mucopolysaccharidosis type I (MPSI); or sufficiently stable levels of iduronate 2-sulfatase to treat mucopolysaccharidosis type II (MPSII).

One of ordinary skill in the art would be able to use routine methods in order to determine the appropriate route of administration and the correct dosage of an effective amount of a composition comprising transduced cells and/or one or more agents that increase transduction efficiency or VCN contemplated herein. It would also be known to those having ordinary skill in the art to recognize that in certain therapies, multiple administrations of pharmaceutical compositions of the invention may be required to effect therapy.

One of the prime methods used to treat subjects amenable to treatment with hematopoietic stem and progenitor cell-based gene therapies is blood transfusion. Thus, one of the chief goals of the compositions and methods contemplated herein is to reduce the number of, or eliminate the need for, transfusions.

In particular embodiments, the drug product is administered once.

In certain embodiments, the drug product is administered 1, 2, 3, 4, 5, 6, 7, 8, 9, or 10 or more times over a span of 1 year, 2 years, 5, years, 10 years, or more.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Validation Assays
Vector Copy Number (VCN) and Transduction Efficiency

Washed cells were resuspended in 2 mL Stem Cell Growth Medium (SCGM)+cytokines and transferred to a standard 12-well non-adherent tissue culture plate. Cells were maintained for an additional 6 days in a standard humidified tissue culture incubator (5% CO2) and then subjected to Vector Copy Number (VCN) analysis or single-cell nested PCR to determine transduction efficiency. Both VCN and the single-cell nested PCR assay were performed with qPCR using primers and probes specific to both the vector and an endogenous control gene. VCN was determined by dividing the amount of vector signal by the amount of the endogenous control gene. For the single-cell nested PCR assay, wells that contained a cell positive for the endogenous control gene and wells that contained a marked cell positive for both the vector and the endogenous control gene were enumerated, and the proportion of marked cells, or transduction efficiency, was calculated.

Methylcellulose Assays

Washed cells were resuspended in 200 µL SCGM and then transferred to 3 mL aliquots of cytokine-supplemented methylcellulose (for example, Methocult M4434 Classic). 1.1 mL was then transferred to parallel 35-mm tissue culture dishes using a blunt 16-gauge needle. Dishes were maintained in a standard humidified tissue culture incubator for 12-16 days and colonies were scored for size, morphology, and cellular composition. Individual colonies were then picked for subsequent VCN analysis or the contents of an entire 35-mm dish were pooled and then subject to VCN analysis.

BlaM Assay for Assessment of Viral Entry

Cells were transduced for 2 hours in the presence of F108, $PGE_2$, and a virus encoding a β-lactamase-Vpr fusion protein. Following transduction, cells were washed and incubated with a fluorescent β-lactamase substrate for 30-60 minutes. β-lactamase cleavage was analyzed by flow cytometry: uncleaved substrate is $GFP^+$, and cleavage of the fluorescent β-lactamase results in a Pacific $Blue^+$ signal. β-lactamase cleavage indicates lentivirus entry into the cell. See also, Cavrois et al. *Nature Biotechnology*. 2002.

Transduction of Long-term Hematopoietic Stem Cells (LT-HSCs)

HSCs transduced with lentivirus were transplanted into NOD/SCID Gamma (NSG) mice to assess the effect of candidate compounds on viral transduction of human long-term hematopoietic stem cells. Transduced cells were washed and resuspended in phosphate-buffered saline (PBS) and transplanted into the tail vein of sub-myeloablated adult NSG mice, with minimal residual toxicity. Mice were housed in a pathogen-free environment per standard IACUC animal care guidelines. At 4 months post-transplant bone marrow (BM) was harvested from both femurs and analyzed for both VCN and engraftment of human cells by staining with an anti-hCD45 antibody (BD #561864) followed by flow cytometry analysis.

Example 2

In Vivo Analysis of PGE2-Treated Human $CD34^+$ Cells

Meta-analysis of NSG transplants with $PGE_2$-treated lentiviral transduced hCD34+ cells from healthy donors (n=3). Human $CD34^+$ cells were transplanted into sub-myeloablated female NSG mice and bone marrow (BM) was analyzed at 4 months post-transplant. BM was harvested from both femurs of NSG mice and half of the sample was stained with anti-hCD45 for approximately 30 minutes at 4° C. Following incubation, samples were washed and analyzed for human $CD45^+$ cells via flow analysis using an anti-hCD45 antibody (BD #561864). No statistically significant difference in the percentage of $hCD45^+$ cells in mouse BM was detected between control-treated and $PGE_2$-treated samples. These results indicate that $PGE_2$ treatment of $hCD34^+$ cells did not significantly increase HSC engraftment. FIG. 1A. The mean VCN of engrafted $PGE_2$-treated $hCD34^+$ cells was about two-fold higher than the mean VCN of control cells at 4 months post-transplant. FIG. 1B.

Example 3

Figure 2A:
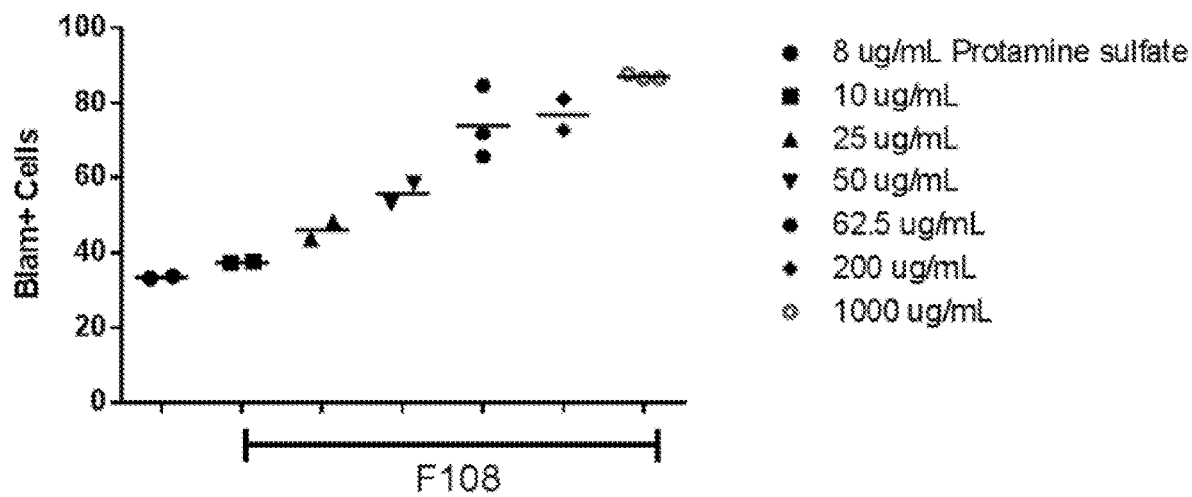
FIG. 2 shows that hCD34+ cells transduced in the presence of increasing concentrations of F108 show dose-dependent increase in (A) viral entry and (B) VCN.
Figure 2B:
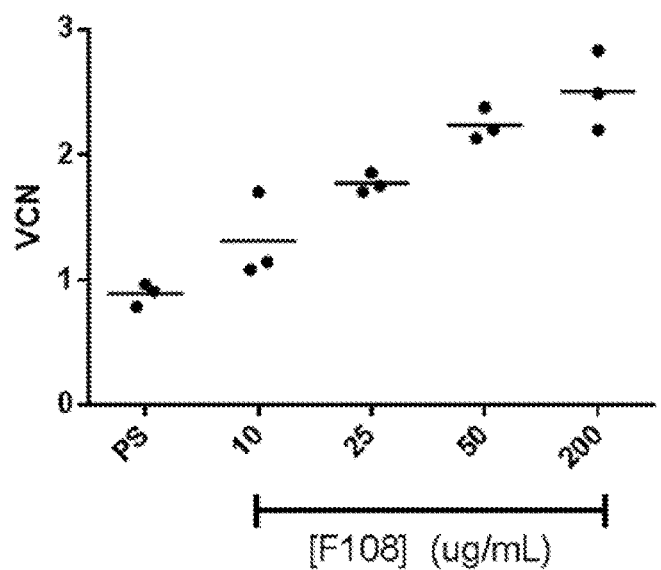

HCD34+ Cells Transduced in the Presence of Increasing Concentrations of F108 Show Dose-Dependent Increase in Viral Entry and VCN $hCD34^+$ cells were transduced for 2 or 24 hours with lentivirus in the presence of protamine sulfate or an increasing concentration of F108. The effect of F108 on lentiviral entry into human $CD34^+$ cells was analyzed using a BlaM assay. Cells were transduced with a lentiviral vector encoding a β-lactamase-Vpr fusion protein. Following a 2 hour transduction, cells were washed and incubated with a fluorescent substrate of β-lactamase. Cells were then analyzed via flow cytometry for β-lactamase substrate cleavage, which correlates with lentiviral entry in $CD34^+$ cells. Flow cytometry analysis revealed that increasing concentrations of F108 during transduction increased LVV entry into $hCD34^+$ cells, observed as an increase in the percentage of cells with cleaved BlaM substrate. The effect of increased lentiviral entry appears to plateau between 62.5 and 200 µg/mL of F108. FIG. 2A. $CD34^+$ cells were transduced with a LVV encoding β-globin. After 24 hours, the cells were washed and plated in MethoCult for a 14 day culture. After 14 days, pooled colonies were analyzed for VCN. Increasing concentrations of F108 during transduction increased VCN compared to control treated cells. FIG. 2B.

Example 4

Figure 3:
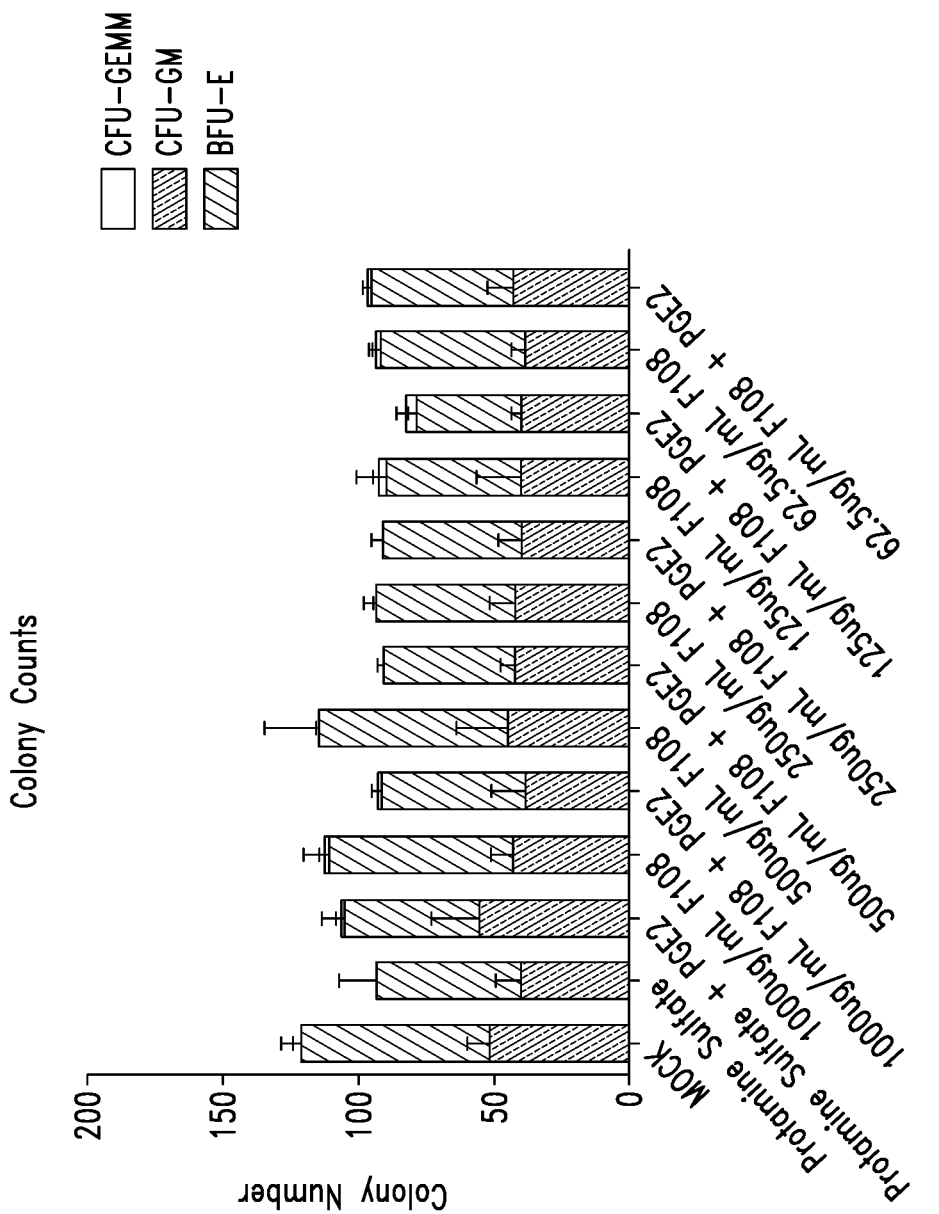
FIG. 3 shows that hCD34+ cells transduced in the presence of F108, $PGE_2$, or F108 and $PGE_2$ do not show decreased cell viability compared to control treated cells.

$CD34^+$ Cells Transduced in the Presence of F108 Do Not Show Decreased Cell Viability $hCD34^+$ cells were transduced with vector, F108, and $PGE_2$ for 24 hours followed by a 14 day MethoCult culture. Colonies in MethoCult were enumerated using STEMvision (Stemcell Technologies). $CD34^+$ cells transduced in the presence of F108 alone, $PGE_2$ alone, and F108 and $PGE_2$ in combination did not alter the colony formation ability of transduced cells, which indicates no substantial effect on cell viability or differentiation capability. FIG. 3.

Example 5

Figure 4B:
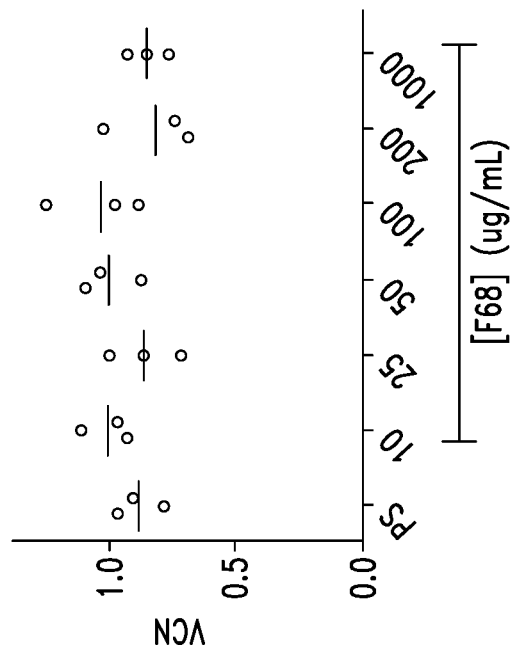
FIG. 4 shows that hCD34+ cells transduced in the presence of increasing concentrations of F68 does not show dose-dependent increase in (A) viral entry and (B) VCN.
Figure 4A:
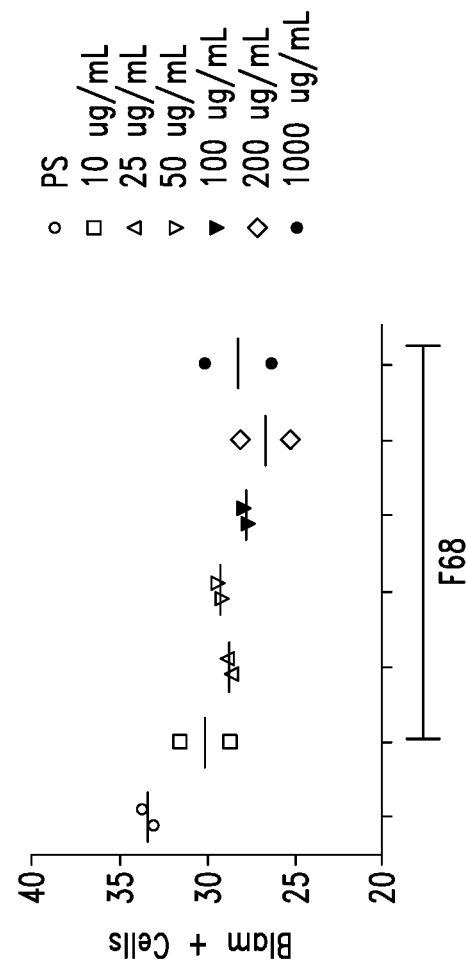

Transduction with Block Copolymers $hCD34^+$ cells were transduced with LVV for 2 or 24 hours in the presence of protamine sulfate or increasing concentrations of the pluronic F68. After a 2 hour transduction, cells were washed and processed for the BlaM entry assay. Flow analysis showed that F68 addition to $hCD34^+$ cells during transduction negatively affects LVV entry. FIG. 4A.

After a 24 hour transduction, cells were washed and cultured for 14 days in MethoCult. Pooled colonies were collected and analyzed for VCN. The presence of F68 during transduction does not affect the VCN of hCD34$^+$ cells. Therefore, F108's ability to increase viral entry and VCN is not a property of all poloxamer block copolymers. FIG. 4B.

Example 6

F108 and PGE$_2$ Increase VCN and Transduction Efficiency in HCD34$^+$ Cells Transduced with LVV hCD34$^+$ cells were transduced for 24 hours with LVV in the presence of protamine sulfate, PGE$_2$, F108, or the combination of F108 and PGE$_2$. After transduction, cells were washed and cultured in MethoCult for 14 days or in cytokine-containing media for 7 days.

Figure 5A:
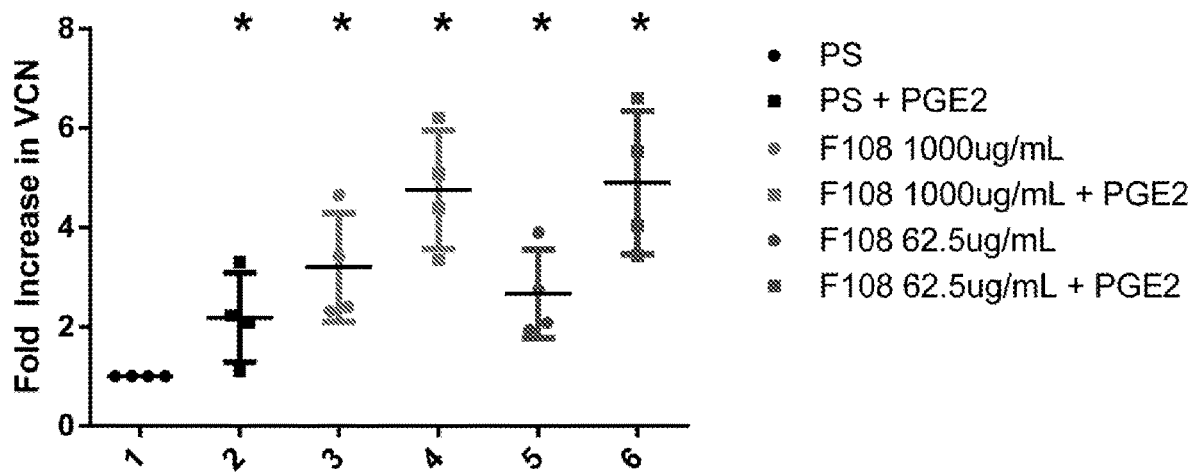
FIG. 5 shows that an increase in VCN and transduction efficiency in hCD34+ cells transduced in the presence of F108 and PGE2 compared to cells transduced in the presence of F108 alone or controls.

After a 14 day MethoCult culture, pooled colonies were collected and analyzed for VCN. Mean VCN data is shown as fold increase in VCN compared to the standard transduction procedure of utilizing protamine sulfate in the transduction media. FIG. 5A. Addition of PGE$_2$ to the transduction results in a 2-fold increase in VCN. F108 addition outperforms PGE$_2$ addition, and the combination of F108 and PGE$_2$ results in an unexpected increase in VCN. Additionally, the combination of F108 and PGE$_2$ is effective when the F108 concentration is either 62.5 µg/mL or 1000 µg/mL.

Figure 5B:
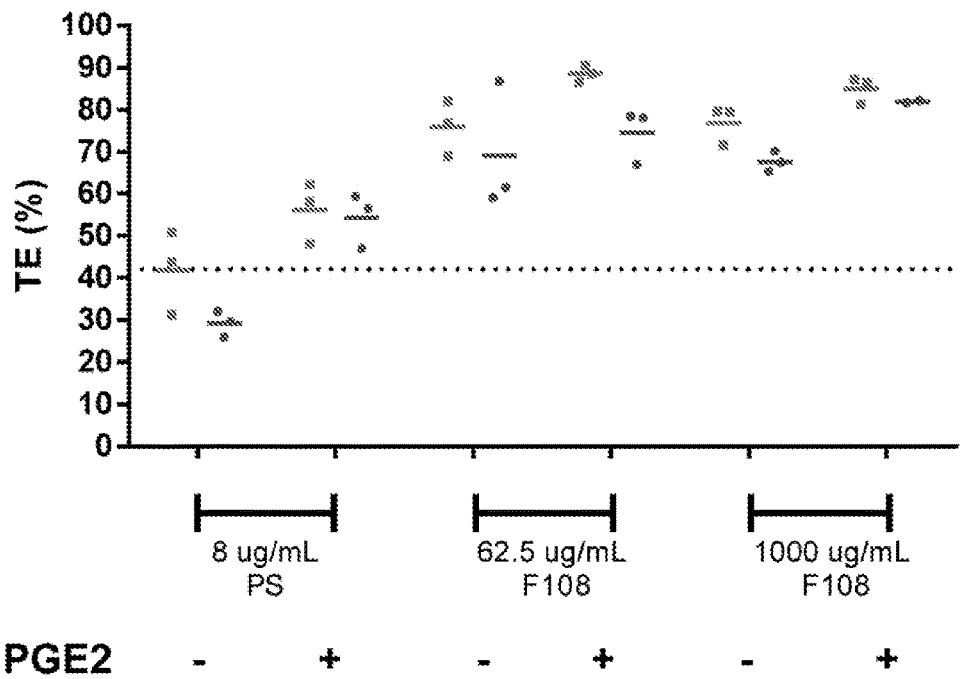

After a 7 day liquid culture, cells were collected and single-cell sorted into a 96-well plate. Cells were lysed and subjected to nested PCR to determine presence of LVV in a single cell. Percentage of cells containing both LVV and an endogenous control gene was determined from number of cells containing the endogenous control gene. LVV transduction efficiency increased in hCD34$^+$ cells transduced in the presence of F108 and PGE$_2$ compared to cells transduced with F108 alone or control treated cells. FIG. 5B.

Example 7

Figure 6A:
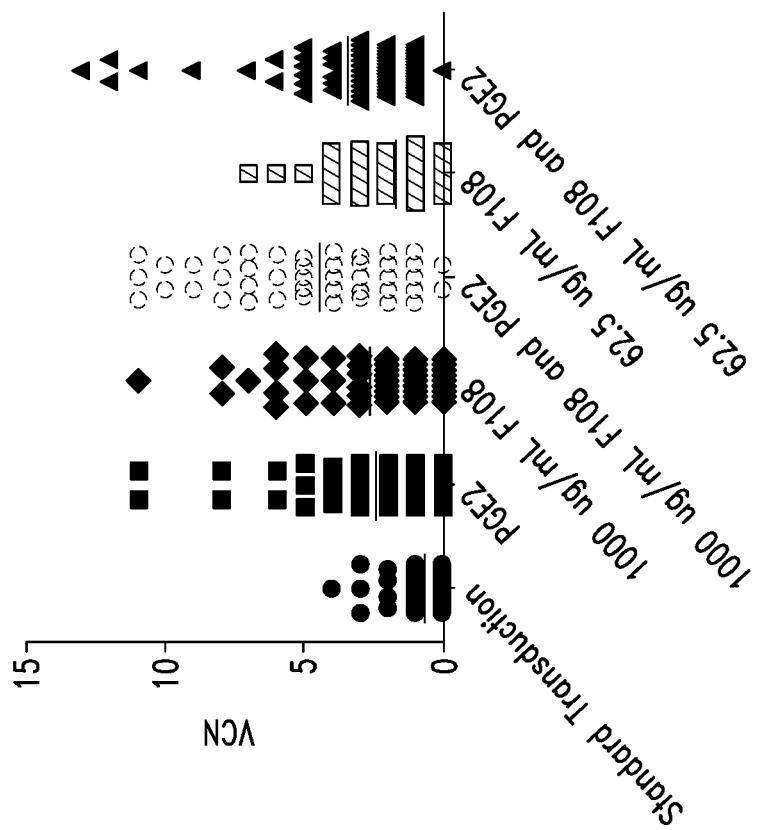
FIG. 6 shows the individual colony analysis from two independent experiments demonstrates increased mean VCN with combination F108 and $PGE_2$ treatment as well as a substantial decrease in the number of progenitors that are not transduced.
Figure 6B:
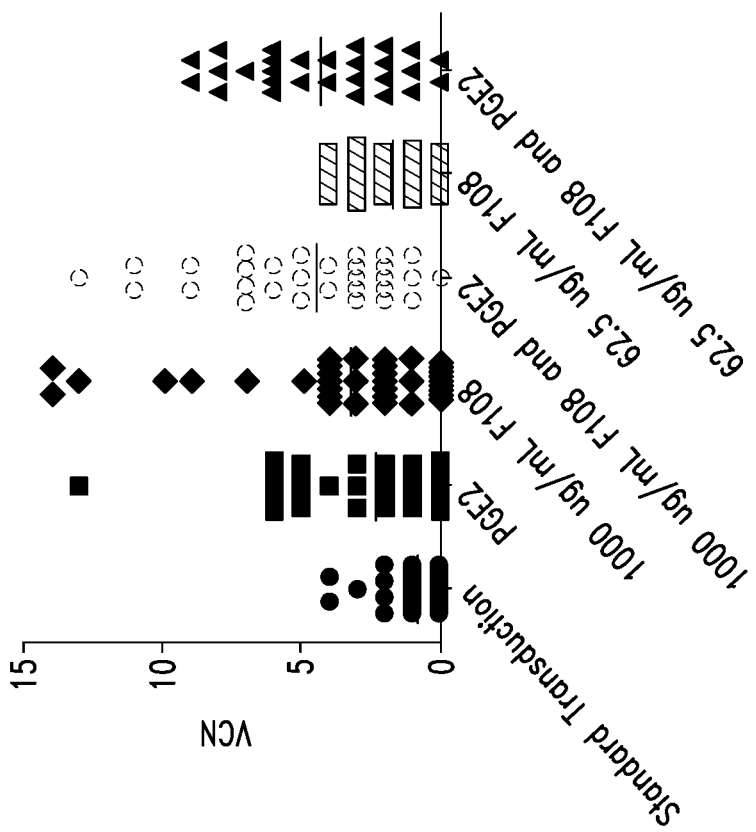

Individual Colony Analysis of HCD34$^+$ Cells Transduced in the Presence of F108 and PGE$_2$ Show Increased Transduction Efficiency and VCN hCD34$^+$ cells were transduced for 24 hours with LVV in the presence of PGE$_2$, F108, or the combination of PGE$_2$ and F108. Transduced cells were then cultured in MethoCult for 14 days. After the culture, individual colonies were picked and analyzed for VCN. The combination of PGE$_2$ and F108 results in an increased mean VCN and also a substantial decrease in the number of colonies with a VCN=0. FIGS. 6A and 6B. These data further support that the transduction efficiency hCD34$^+$ cells increased with the combination treatment during transduction.

Example 8

Figure 7:
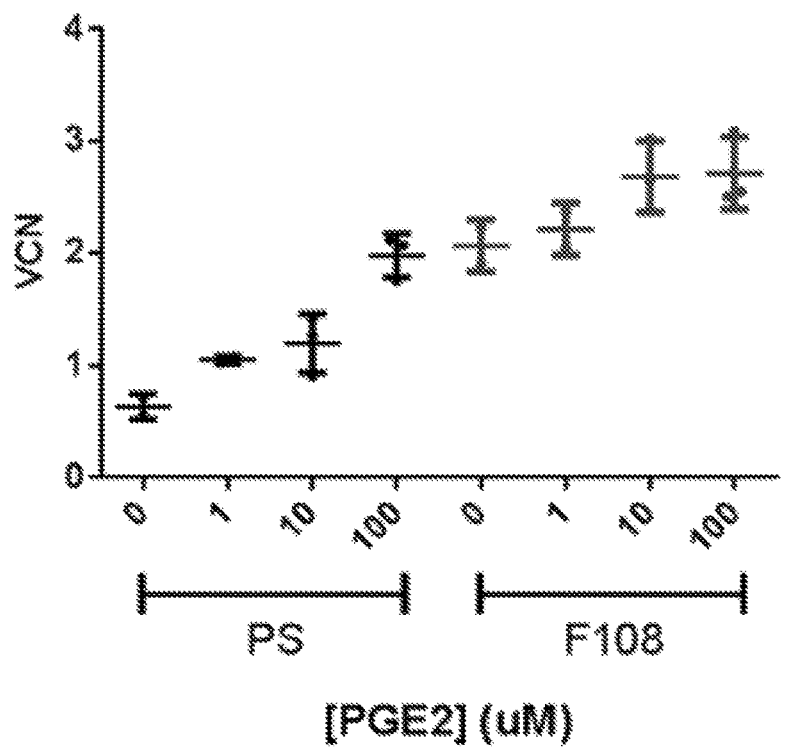
FIG. 7 shows hCD34+ cells transduced in the presence of increasing concentrations of $PGE_2$ and static F108 concentration do not show a dose-dependent increase in VCN.

HCD34$^+$ Cells Transduced in the Presence of Increasing Concentrations of PGE$_2$ in Combination with Static F108 Concentration Does Not Increase VCN hCD34$^+$ cells were transduced for 24 hours with LVV in the presence of either protamine sulfate or F108 and increasing concentrations of PGE$_2$. After 24 hours, cells were washed and plated in MethoCult for 14 days. Pooled colonies were then collected and analyzed for VCN. In the presence of protamine sulfate, increasing concentrations of PGE$_2$ resulted in a dose-dependent increase in VCN. However, in the presence of F108, increasing PGE$_2$ concentrations at least 10-fold does not result in a dose-dependent increase in VCN. FIG. 7.

Example 9

Figure 8:
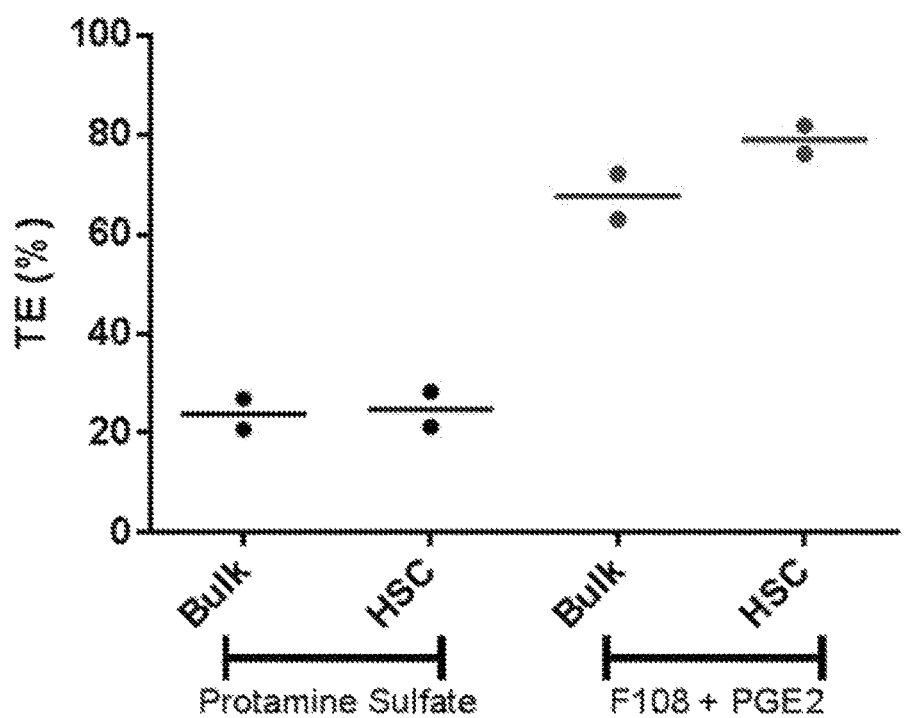
FIG. 8 shows that both bulk hematopoietic cells populations and phenotypic stem cells ($CD34^+CD38^{Lo}CD90^+CD45^{RA-}$) transduced in the presence of $PGE_2$ and F108 treatment show increased transduction efficiency compared to standard transduction conditions using protamine sulfate.

H CD34$^+$CD38$^{Lo}$CD90$^+$CD45 Cells Transduced in the Presence of F108 and PGE$_2$ Show Increased Transduction Efficiency Bulk cell preparations were transduced in the presence of vector or vector, F108, and PGE$_2$ for 24 hours. After transduction, cells were stained with antibodies against cell surface markers (CD34$^+$CD38$^{Lo}$CD90$^+$CD45 cells). Stained cells were then sorted using a Sony Cell Sorter. For each bulk cell sample, approximately 20,000 cells were sorted from the forward scatter and side scatter gates. Additionally, 10,000-16,000 cells were sorted from each sample that were CD34$^+$CD38$^{Lo}$CD90$^+$CD45$^{RA}$ cells (phenotypic HSCs). Sorted cells were then cultured in cytokine-containing media for an additional 4 days to exclude pseudo-transduction from the analysis. After culture, the cells were then single-cell sorted into 96 well plates and analyzed via the single-cell PCR assay to assess transduction efficiency. The transduction efficiency of bulk cells and CD34$^+$CD38$^{Lo}$CD90$^+$CD45$^{RA}$ cells transduced with the standard transduction procedure (n=2) was equivalent. The transduction efficiency of bulk cells and CD34$^+$CD38$^{Lo}$CD90$^+$CD45$^{RA}$ cells transduced with F108 and PGE$_2$ (n=2) was also equivalent. Additionally, the transduction efficiency of both bulk cells and CD34$^+$CD$^{Lo}$CD90$^+$CD45$^{RA}$ cells transduced in the presence of F108 and PGE$_2$ was approximately 3-4 fold higher than the transduction efficiency of these cell samples under standard transduction conditions. FIG. 8.

Example 10

Figure 9:
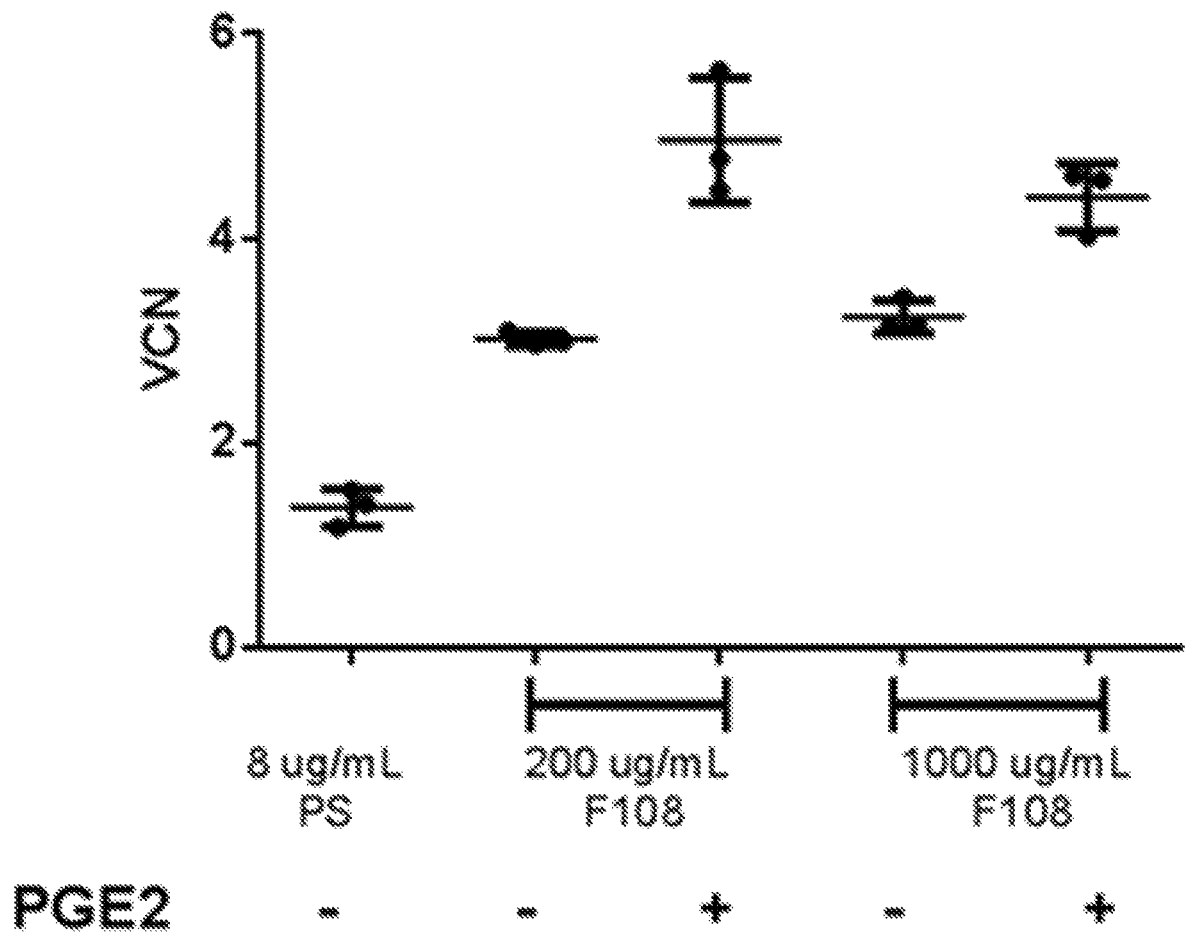
FIG. 9 shows that hCD34+ cells transduced in the presence of F108 or F108 and $PGE_2$ show increased VCN compared to controls.

HCD34$^+$ Cells Transduced in the Presence of F108 and PGE$_2$ Show Increased Transduction Efficiency with Lentivirus Prepared from Suspension Cultures Examples 2-9 were performed using lentivirus prepared from adherent cell cultures. In this example, lentivirus was produced from suspension cultures. Although the lentivirus purification scheme differs between lentivirus prepared from adherent cultures compared to suspension cultures, the differences in production and purification did not affect the ability of the F108 and PGE$_2$ combination to increase VCN in day 14 MethoCult cultured cells. There is an approximate 2-fold increase in VCN with F108 alone, and combination of F108 and PGE$_2$ results in approximate 5-fold increase over standard transduction methods. FIG. 9.

Example 11

F108 and PGE$_2$ Increase Transduction of HCD34$^+$ Cells In Vivo

A low-transducing cell lot of hCD34$^+$ cells (VCN of 0.3 under standard conditions) was transduced with lentiviral vector in the presence of protamine sulfate, PGE$_2$, F108 (200 µg/mL or 1000 µg/mL), or the combination of PGE$_2$ and F108 for 24 hours. Following transduction, cells were washed and immediately injected into busulfan-treated NSG mice.

Figure 10A:
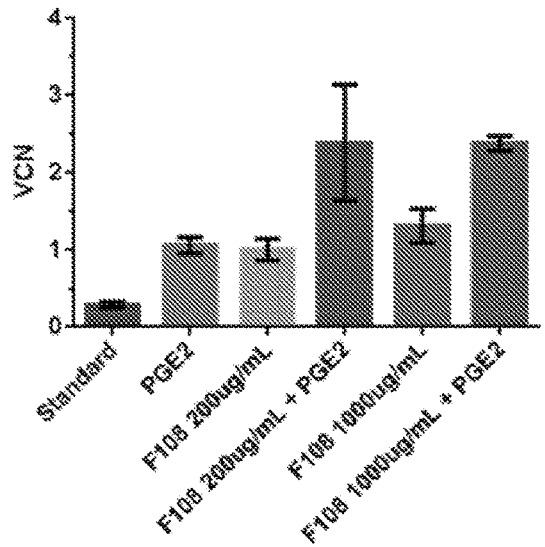
FIG. 10 shows VCN analysis and transduction efficiency of hCD34+ cells treated with $PGE_2$, F108, or a combination thereof (A) F108, alone or in combination with PGE2, enhances VCN of a low transducing cell lot. (B) F108, alone or in combination with PGE2, enhances the transduction efficiency of a low transducing cell lot. (C) VCN analysis at 2 months post-transplant reveals that F108, alone or in combination with PGE2, enhances in vivo VCN of engrafted hCD34+ cells. (D) VCN analysis at 4 months post-transplant reveals that F108, alone or in combination with PGE2, enhances in vivo VCN of engrafted hCD34+ cells.
Figure 10B:
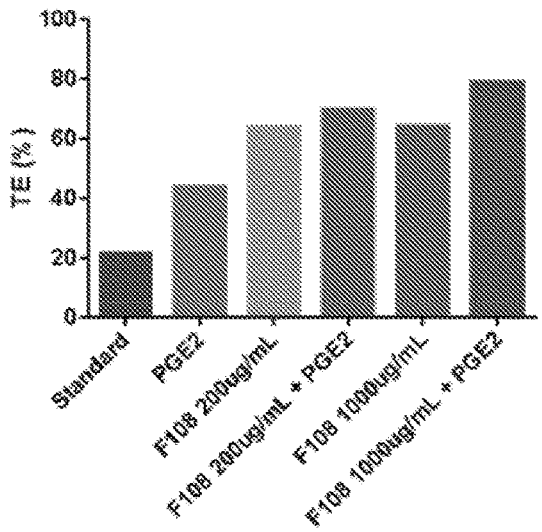

An aliquot of cells from the graft were retained for VCN and transduction efficiency analysis. PGE$_2$- and F108-treated hCD34$^+$ cells increased the mean VCN by approximately 3-fold compared to control cells treated with protamine sulfate. FIG. 10A. VCN was increased further when PGE$_2$ and F108 were used in combination. FIG. 10A. Individual colony qPCR analysis was used to measure the transduction efficiency of the hCD34$^+$ cells treated with the various agents. The transduction efficiencies of the hCD34$^+$ cells increased from ~20% (control, protamine sulfate), to ~40% (PGE$_2$- or F108-treated cells), or to ~65-80% (PGE$_2$- and F108-treated cells). FIG. 10B.

Figure 10C:
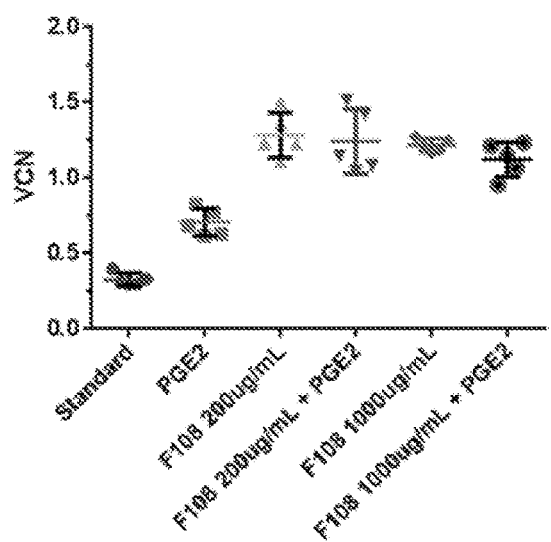

Two months post-transplant, 5 mice/group were sacrificed and BM was harvested and analyzed to evaluate in vivo VCN. The in vivo VCN of engrafted cells transduced in the presence of protamine sulfate was very similar to the graft VCN (~0.3). in vivo VCN increased approximately 2-fold in PGE$_2$-treated cells. Cells treated with F108, either alone or in combination with PGE$_2$ showed comparable increases in in vivo VCN of about 1.2, a 4-fold improvement over standard transduction conditions (protamine sulfate). FIG. 10C. The relative increases in in vivo VCN are comparable to the relative transduction efficiencies of the grafts.

Figure 10D:
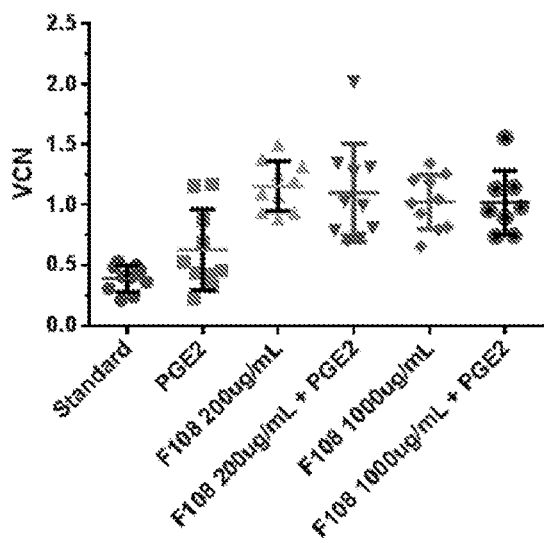

Four months post-transplant, 5 mice/group were sacrificed and BM was harvested and analyzed to evaluate in vivo VCN. The in vivo VCN of engrafted cells transduced in the presence of protamine sulfate was very similar to the graft VCN (~0.3). in vivo VCN increased approximately 1.6-fold in PGE$_2$-treated cells. Cells treated with F108, either alone or in combination with PGE$_2$ showed comparable increases in in vivo VCN of about 1.0-1.2, an about 2.6- to about 3-fold improvement over standard transduction conditions (protamine sulfate). FIG. 10D.

The relative increases in in vivo VCN measured at four months post-transplant are comparable to the relative transduction efficiencies of the grafts.

Example 12

Engraftment and Differentiation Capability of HCD34$^+$ Cells Treated in the Presence of F108 AND PGE$_2$ Two months and 4 months post-transplant, BM was harvested from the transplanted mice discussed in Example 11. The BM was analyzed for engraftment of hCD34$^+$ cells. Cells were stained with an antibody cocktail recognizing various cell surface markers (CD45, CD33, CD3, CD19) and analyzed via flow cytometry. All groups demonstrated a high level (~80%) of hCD34$^+$ engraftment and there was no statistically significant effect of F108 or PGE$_2$. FIG. 11A-E. Additionally, there was no significant difference in the proportion of myeloid (CD33$^+$) or lymphoid (CD3$^+$ or CD19$^+$) cells regardless of treatment (F108, PGE$_2$, or combination). These data indicate that the VCN enhancers, e.g., F108, PGE$_2$, do not affect the ability of the transduced hCD34$^+$ cells to engraft nor do they skew the differentiation potential of engrafted cells.

Example 13

F108 and Staurosporine Increase VCN in HCD34$^+$ Cells Transduced with LVV hCD34$^+$ cells were transduced for 24 hours with LVV in the presence of protamine sulfate (standard), staurosporine, F108, or the combination of F108 and staurosporine. After transduction, cells were washed and cultured in MethoCult for 14 days.

Figure 12:
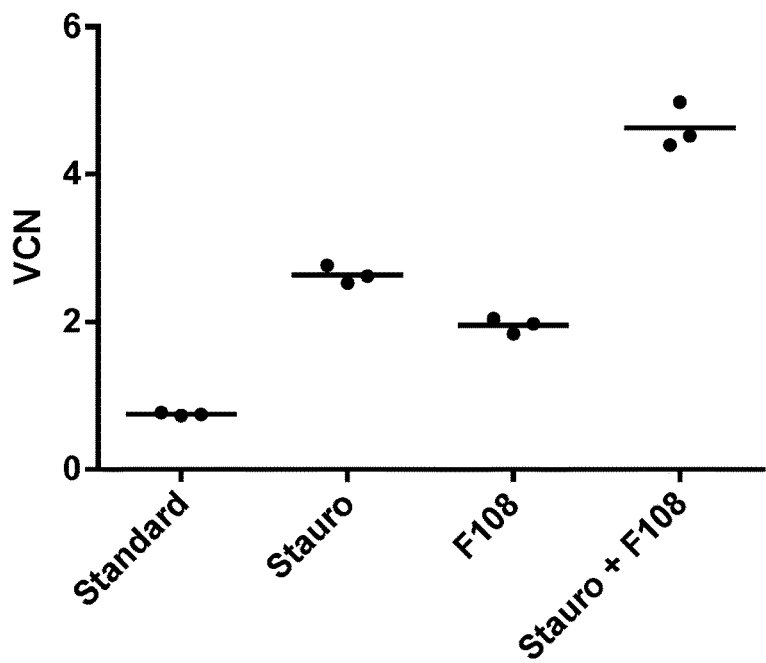
FIG. 12 shows that hCD34+ cells transduced in the presence of staurosporine, F108, or F108 and staurosporine show increased VCN compared to controls.

After a 14 day MethoCult culture, pooled colonies were collected and analyzed for VCN. VCN data is shown as fold increase in VCN compared to the standard transduction procedure of utilizing protamine sulfate in the transduction media. Addition of F108 to the transduction results in a 2-fold increase in VCN; staurosporine addition outperforms F108 addition, and the combination of F108 and staurosporine results in an unexpected increase in VCN compared to treatment with F108 or staurosporine alone. FIG. 12.

Example 14

HCD34$^+$ Cells Transduced in the Presence of F127 Alone or in Combination with PGE$_2$ Increase VCN hCD34$^+$ cells were transduced for 24 hours with LVV in the presence of either protamine sulfate or one of two poloxamers, F108 or F127, with or without PGE$_2$. F127 has a higher molecular mass than F108.

Figure 13:
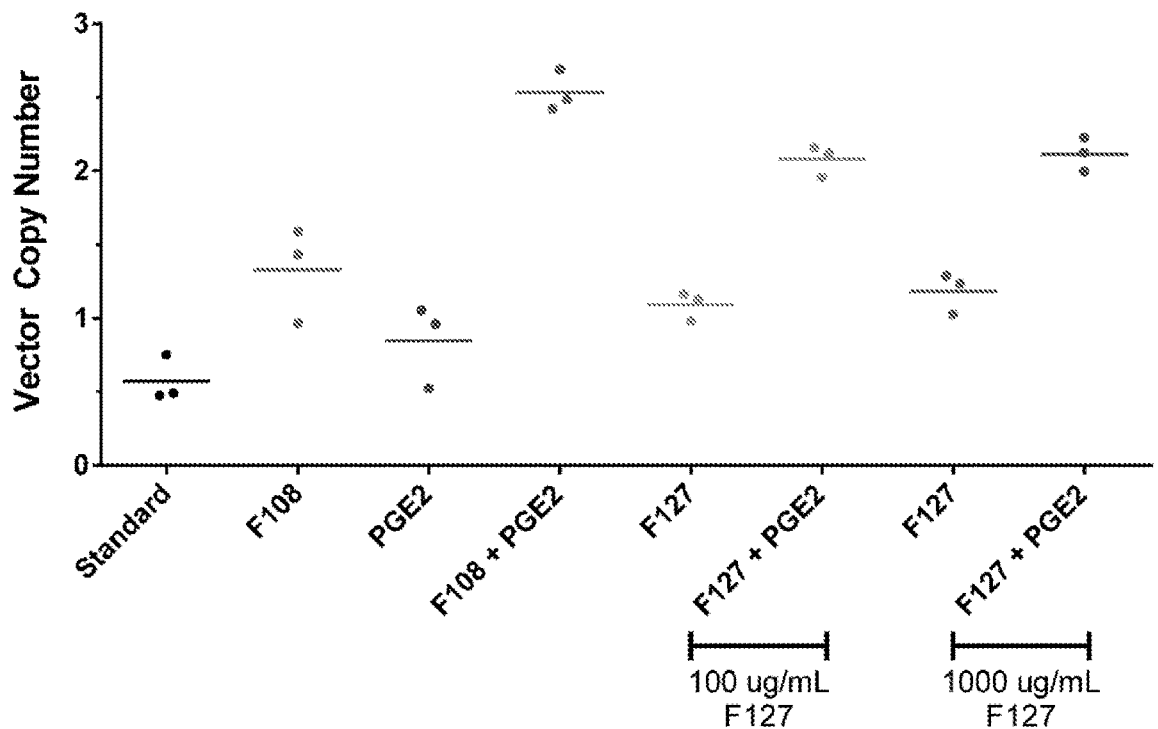
FIG. 13 shows that F108 and F127 both increase VCN in hCD34+ cells over standard transduction with protamine sulfate. VCN is further enhanced with addition of $PGE_2$ to both F108 and F127 transductions.

After 24 hours, cells were washed and plated in MethoCult for 14 days. Pooled colonies were then collected and analyzed for VCN. F108 increases VCN ~2-fold compared protamine sulfate, and further increases VCN in the presence of PGE$_2$. Another poloxamer, F127, increased VCN ~2-fold at two tested concentrations, 100 µg/mL and 1000 µg/mL, compared to protamine sulfate. Additionally, F127 combined with PGE$_2$ increased VCN similarly to the F108 and PGE$_2$ combination. FIG. 13. In contrast, F68 (see Example 5), which has a molecular mass approximately half of F108, does not increase VCN or transduction efficiency of hCD34$^+$ cells.

Example 15

HCD34$^+$ Cells Transduced in the Presence of P105 Alone or in Combination with PGE$_2$ Increase VCN hCD34$^+$ cells were transduced for 24 hours with LVV in the presence of either protamine sulfate or one of two poloxamers, F105 or F108, and F105 with PGE$_2$. F127 has a higher molecular mass than F108.

Figure 14:
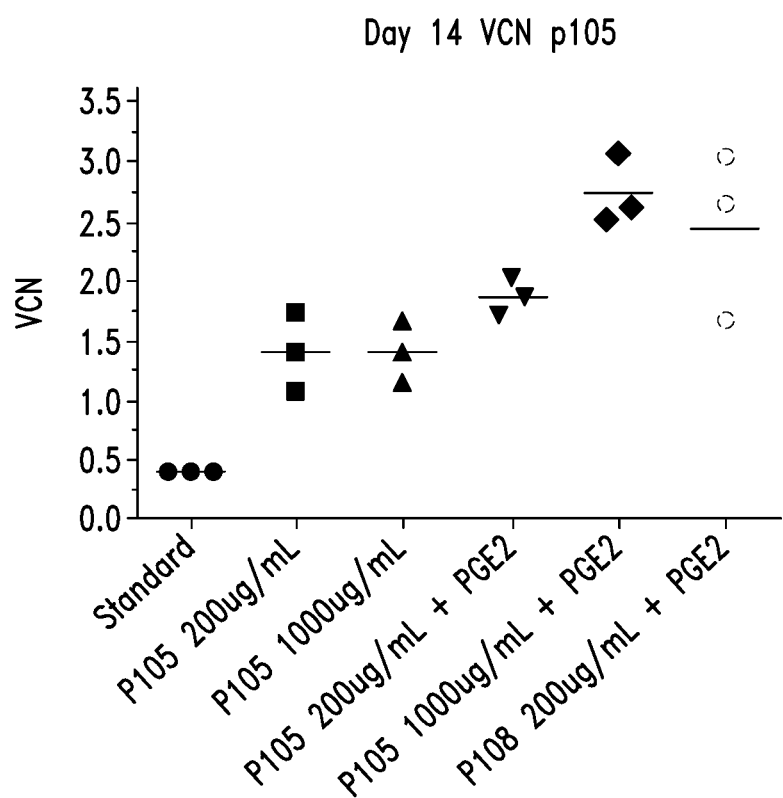
FIG. 14 shows that F108 and P105 both increase VCN in hCD34+ cells over standard transduction with protamine sulfate. VCN is further enhanced with addition of $PGE_2$ to P105 and F108 transductions.

After 24 hours, cells were washed and plated in MethoCult for 14 days. Pooled colonies were then collected and analyzed for VCN. P105 increases VCN ~3-fold at both concentrations test compared protamine sulfate (standard) and further increases VCN in the presence of PGE$_2$. FIG. 14. In contrast, F68 (see Example 5), does not increase VCN or transduction efficiency of hCD34$^+$ cells.

Example 16

Figure 15:
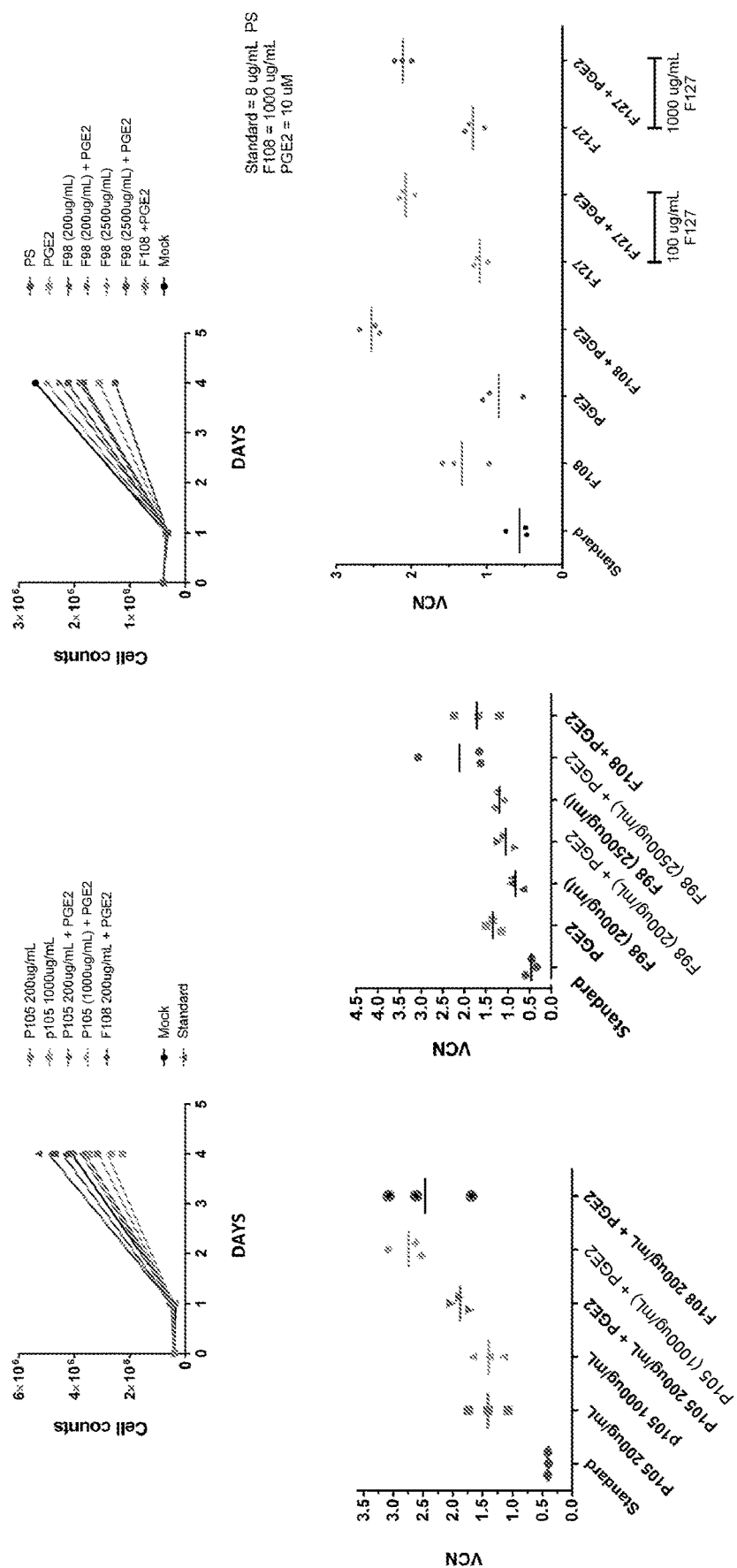
FIG. 15 shows that P105 (data from FIG. 14), F127 (data from FIGS. 13), F108, and F98 increase VCN in hCD34+ cells over standard transduction with protamine sulfate. VCN is further enhanced with addition of $PGE_2$.

Poloxamers that Increase VCN in HCD34$^+$ Cells hCD34$^+$ cells were enriched from mobilized peripheral blood and transduced for 24 hours with LVV in the presence of either protamine sulfate or P105, F127, F108, or F98 with and without addition of PGE$_2$. Cells were then cultured in SCGM to monitor cell growth and plated in MethoCult for colony formation and VCN analysis. P105, F127, F108, and F98 do not impact the ability of the cells to grow. Replacement of protamine sulfate with P105, F127, F108, or F98 increased VCN, which was further increased with the addition of PGE$_2$. FIG. 15.

EXAMPLE 17

Poloxamers that Increase VCN and Decrease Cell Survival of HCD34$^+$ CELLS hCD34$^+$ cells were enriched from mobilized peripheral blood and transduced for 24 hours with LVV in the presence of either protamine sulfate or P123, P104, L101, or F108 with and without addition of PGE$_2$. Cells were then cultured in SCGM to monitor cell growth and plated in MethoCult for colony formation and VCN analysis.

Figure 16:
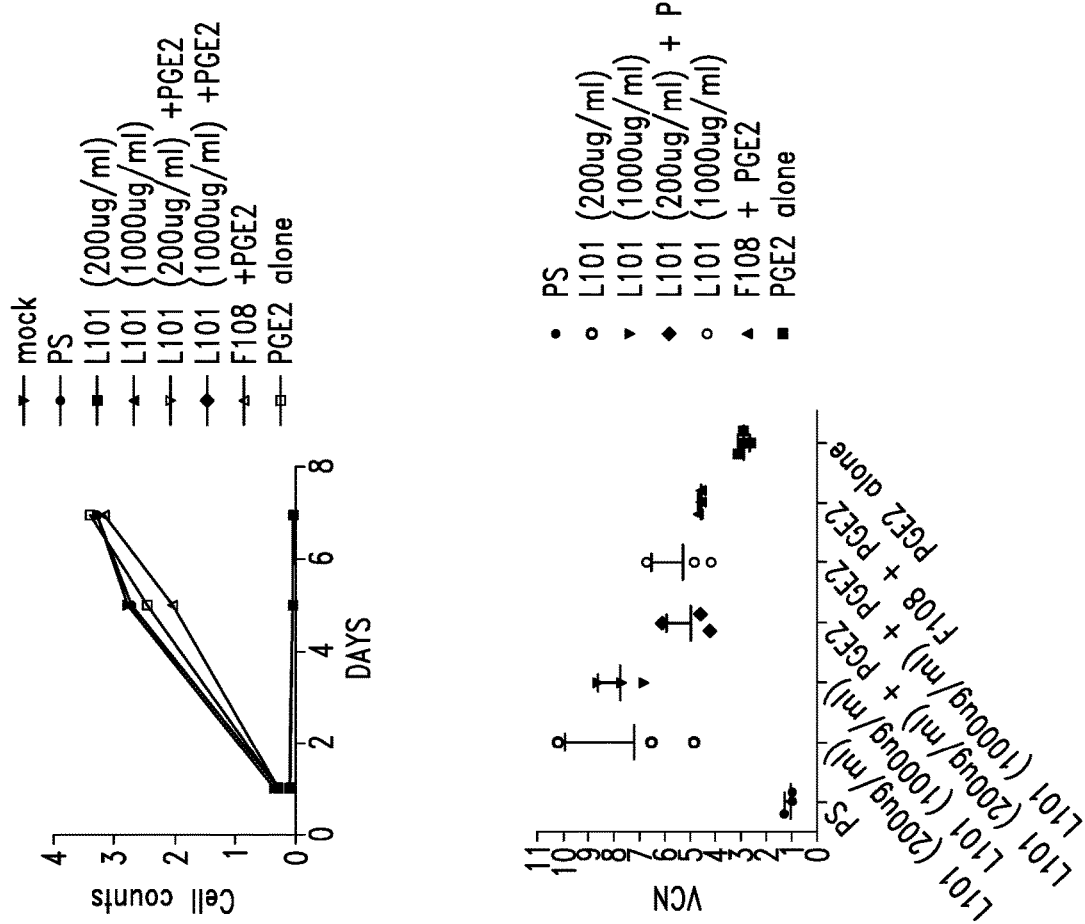
FIG. 16 shows that P123, P104, L101, and F108 increase VCN in hCD34+ cells over standard transduction with protamine sulfate, but that P123, P104, and L101 also decrease cell growth. VCN is enhanced with addition of P123 and $PGE_2$.

Replacement of protamine sulfate with P123, P104, or L101 increased VCN but also decreased cell growth. PGE$_2$ further increased VCN in combination with P123. VCN was calculated from SCGM cultures at day 7 for P123 and L101 because of insufficient colony formation in MethoCult samples. FIG. 16.

Example 18

Figure 17:
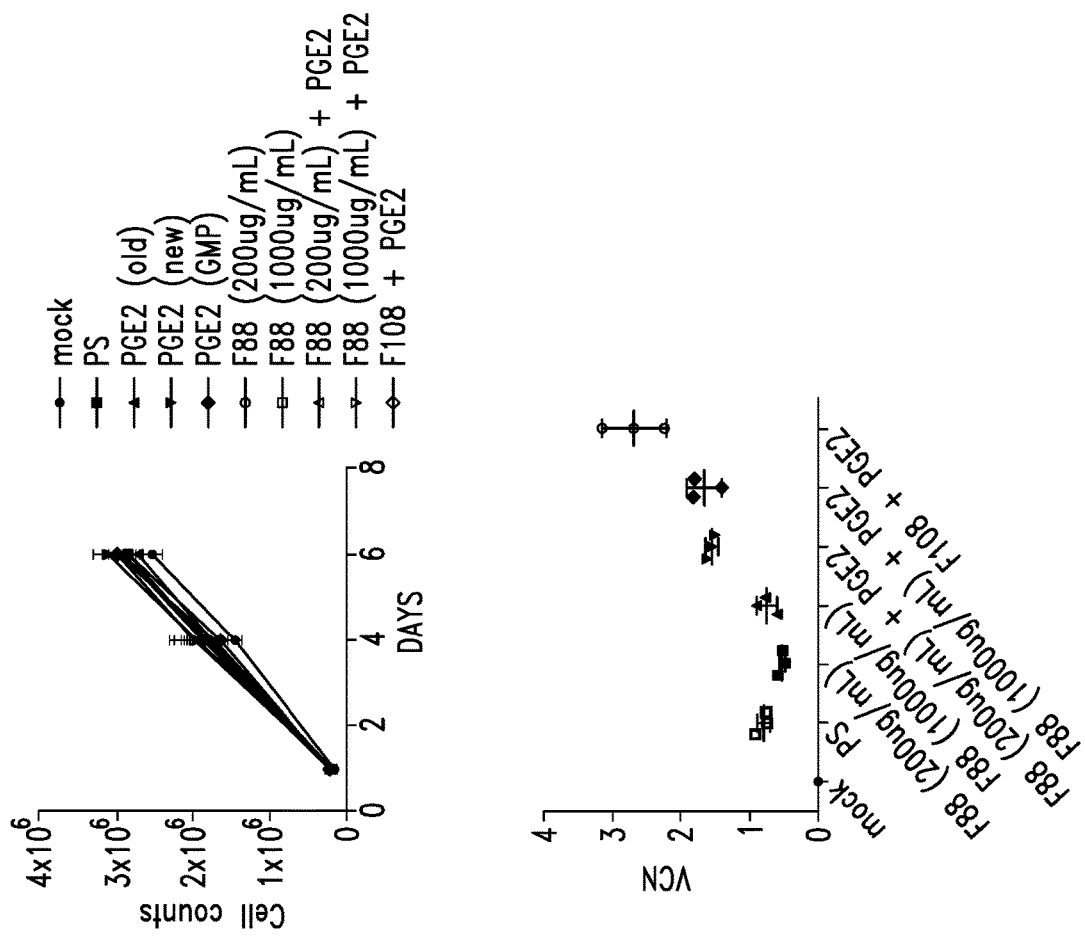
FIG. 17 shows that F87, F88, and F68 do not increase VCN in hCD34+ cells over standard transduction with protamine sulfate, and do not affect cell growth.

Poloxamers That Do Not Increase VCN or Affect Cell Survival of HCD34⁺ Cells hCD34⁺ cells were enriched from mobilized peripheral blood and transduced for 24 hours with LVV in the presence of either protamine sulfate or F87, F88, F68, or F108 with and without addition of $PGE_2$. Cells were then cultured in SCGM to monitor cell growth and plated in MethoCult for colony formation and VCN analysis. F87, F88, and F68 do not affect cell growth or increase VCN. FIG. 17.

Example 19

F108 and $PGE_2$ Increase VCN of $\beta^0/\beta^0$ HCD34⁺ Cells hCD34⁺ cells were enriched from mobilized peripheral blood of a patient having a β0/β0 genotype and transduced for 24 hours with the BB305 clinical LVV encoding human βA-T87Q at an MOI of 20 in the presence of 200 µg/mL F108 and 10 µM Dinoprostone ($PGE_2$). Aliquots of the transduced hCD34+ cells were cultured ex-vivo in cytokine-supplemented SCGM for 7 days to clear non-integrated LVV sequences for determining the % LVV+ cells or cells were cultured in MethoCult for 14 days for colony formation and VCN analysis.

Figure 18:
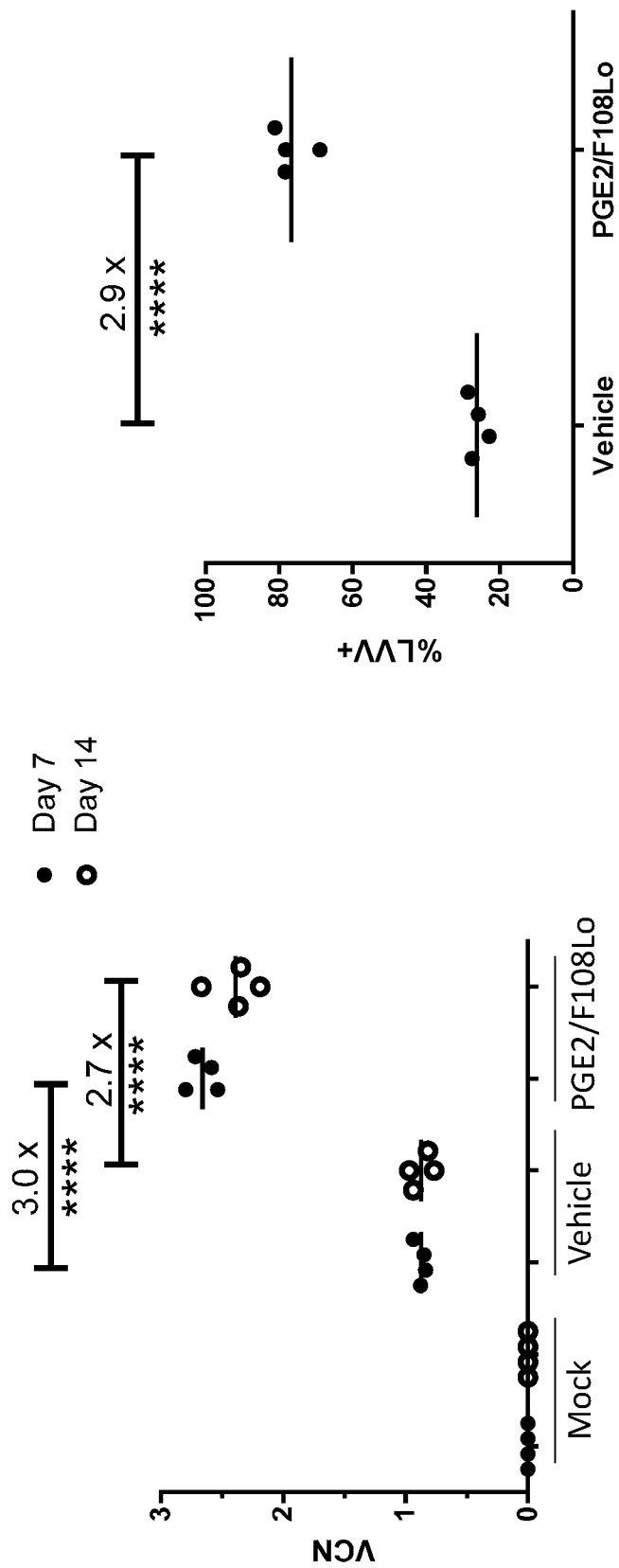
FIG. 18 shows that $\beta^0/\beta^0$ hCD34+ cells transduced in the presence of $PGE_2$ and F108 have about a three-fold increase in VCN and percent cells transduced (% LVV+) compared to control transduced cells.

% LVV+: Single cells were isolated by FACS and deposited in 96-well plates containing lysis buffer. Following lysis, the viral-specific sequence from a lentiviral vector encoding a β-globin variant was amplified by PCR along with a control genomic sequence not present in the vector. The PCR products from each single cell were then analyzed by qPCR for presence of genomic sequence, indicating a successfully captured cell. For each captured cell, qPCR was used to identify whether viral sequence is also present, indicating that the cell had been transduced with the lentiviral vector. Fraction of vector positive cells was then calculated across the entire set of sampled cells. The % LVV+ of the β0/β0 hCD34+ cells was about 77%. FIG. 18, right panel.

VCN: At day 14 colonies were picked and subjected to a single-cell nested PCR assay to determine VCN. The VCN of the hCD34+ cells was about 2.9 copies per diploid genome. FIG. 18, left panel.

Example 20

Figure 19:
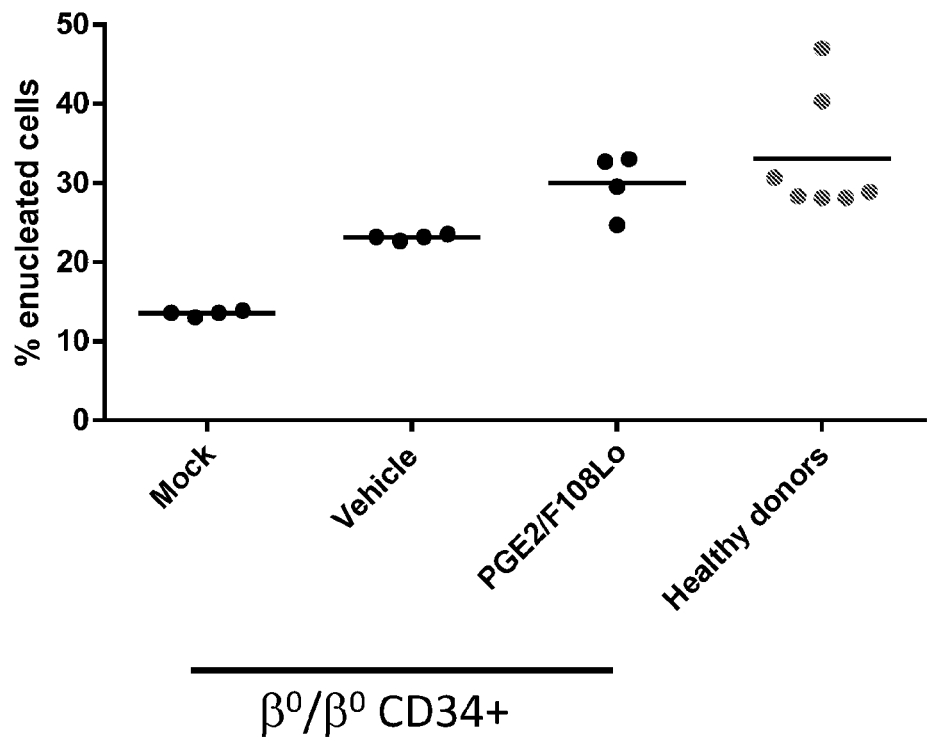
FIG. 19 shows that the number of enucleated erythroid cells differentiated from $\beta^0/\beta^0$ hCD34+ cells transduced in the presence of $PGE_2$ and F108 is comparable to the number of enucleated erythroid cells differentiated from hCD34+ cells obtained from healthy donors.

F108 and $PGE_2$ Increase Enucleation of Erythroid Differentiated $\beta^0/\beta^0$ HCD34⁺ Cells hCD34⁺ cells were enriched from mobilized peripheral blood and transduced for 24 hours with LVV at an MOI of 20 in the presence of either protamine sulfate or F108 with $PGE_2$. Transduced hCD34⁺ cells were plated in erythroid expansion culture for 7 days followed by erythroid differentiation culture for 10 days. Differentiated cells were then harvested by centrifugation, stained with DRAQ5 DNA dye, and analyzed by FACS to quantify the fraction of DNA-negative enucleated cells. The combination of F108 with $PGE_2$ restored the number of enucleated erythroid cells from $\beta^0/\beta^0$ donors to the near-normal number of enucleated erythroid cells from healthy donors. FIG. 19.

Example 21

Figure 20:
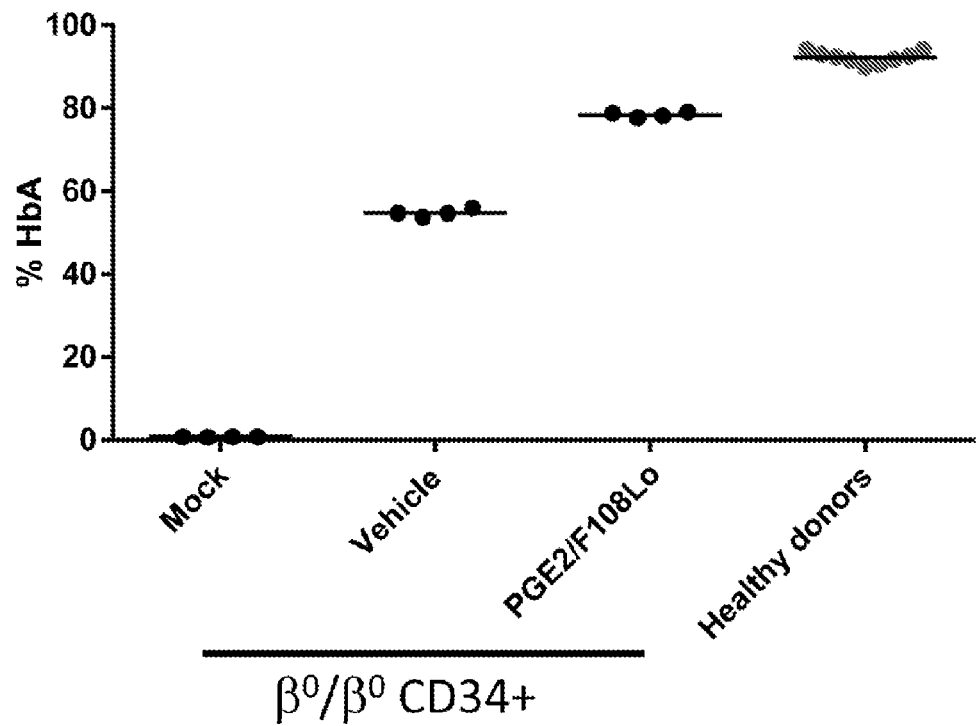
FIG. 20 shows that the amount of HbA produced by enucleated erythroid cells differentiated from $\beta^0/\beta^0$ hCD34+ cells transduced in the presence of $PGE_2$ and F108 is comparable to the amount of HbA produced by enucleated erythroid cells differentiated from hCD34+ cells obtained from healthy donors.

F108 and $PGE_2$ Increase % HBA in Erythroid Differentiated $\beta^0/\beta^0$ HCD34⁺ Cells hCD34⁺ cells were enriched from mobilized peripheral blood and transduced for 24 hours with LVV at an MOI of 20 in the presence of either protamine sulfate or F108 with $PGE_2$. Transduced hCD34+ cells were plated in erythroid expansion culture for 7 days followed by erythroid differentiation culture for 10 days. Differentiated cells were then harvested by centrifugation, stained with DRAQ5 DNA dye, and analyzed by FACS to quantify the fraction of DNA-negative enucleated cells. Differentiated cells were also lysed in ACK buffer and lysates analyzed by ion-exchange HPLC to quantify the fraction of Hemoglobin A protein (HbA). The combination of F108 with $PGE_2$ restored the level of HbA from $\beta^0\beta^0$ donors to the near-normal HbA level in healthy donors. FIG. 20.

Example 22

F108 and $PGE_2$ Increase VCN of SCD Patient HCD34⁺ Cells hCD34⁺ cells were harvested from the bone marrow of a patient with SCD. The cells were transduced for 24 hours with the BB305 clinical LVV encoding human $\beta^{A-T87Q}$ at an MOI of 30 in the presence of 200 µg/mL F108 and 10 µM Dinoprostone ($PGE_2$). Aliquots of the transduced hCD34⁺ cells were cultured ex-vivo in cytokine-supplemented SCGM for 7 days to clear non-integrated LVV sequences for determining the % LVV+ cells or cells were cultured in MethoCult for 14 days for colony formation and VCN analysis.

% LVV+: Single cells were isolated by FACS and deposited in 96-well plates containing lysis buffer. Following lysis, the viral-specific sequence from a lentiviral vector encoding a β-globin variant was amplified by PCR along with a control genomic sequence not present in the vector. The PCR products from each single cell were then analyzed by qPCR for presence of genomic sequence, indicating a successfully captured cell. For each captured cell, qPCR was used to identify whether viral sequence is also present, indicating that the cell had been transduced with the lentiviral vector. Fraction of vector positive cells was then calculated across the entire set of sampled cells. The % LVV+ of the SCD hCD34⁺ cells was about 83%.

VCN: At day 14 colonies were picked and subjected to a single-cell nested PCR assay to determine VCN. The VCN of the hCD34⁺ cells was about 3.3 copies per diploid genome.

Example 23

F108 Does Not Significantly Alter Colony Differentiation

Figure 21:
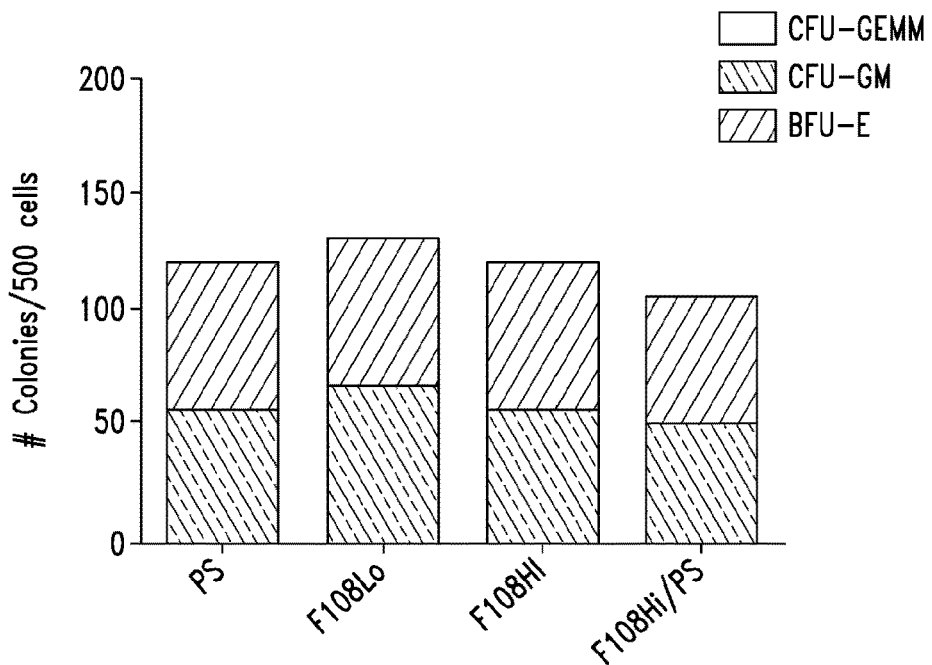
FIG. 21 shows colony formation analyses for human hematopoietic progenitor cells transduced with 8 µg/mL protamine sulfate (PS), 10 µg/mL F108 (F108Lo), 1000 µg/mL F108 (F108Hi), or 1000 µg/mL F108 in combination with 8 µg/mL protamine sulfate (F108Hi/PS). Colony formation was not significantly affected by the treatments.

Human CD34+ cells were transduced with 8 µg/mL protamine sulfate (PS), 10 µg/mL F108 (F108Lo), 1000 µg/mL F108 (F108Hi), or 1000 µg/mL F108 in combination with 8 µg/mL protamine sulfate (F108Hi/PS). Colonies were enumerated and determined to be of the erythroid or myeloid lineage. Neither PS nor F108 significantly affected the ability of the hematopoietic progenitors to form colonies. FIG. 21.

Example 24

F108 and $PGE_2$ Increase Lentiviral Transduction Efficiency In Phenotypic HSCs

Figure 22:
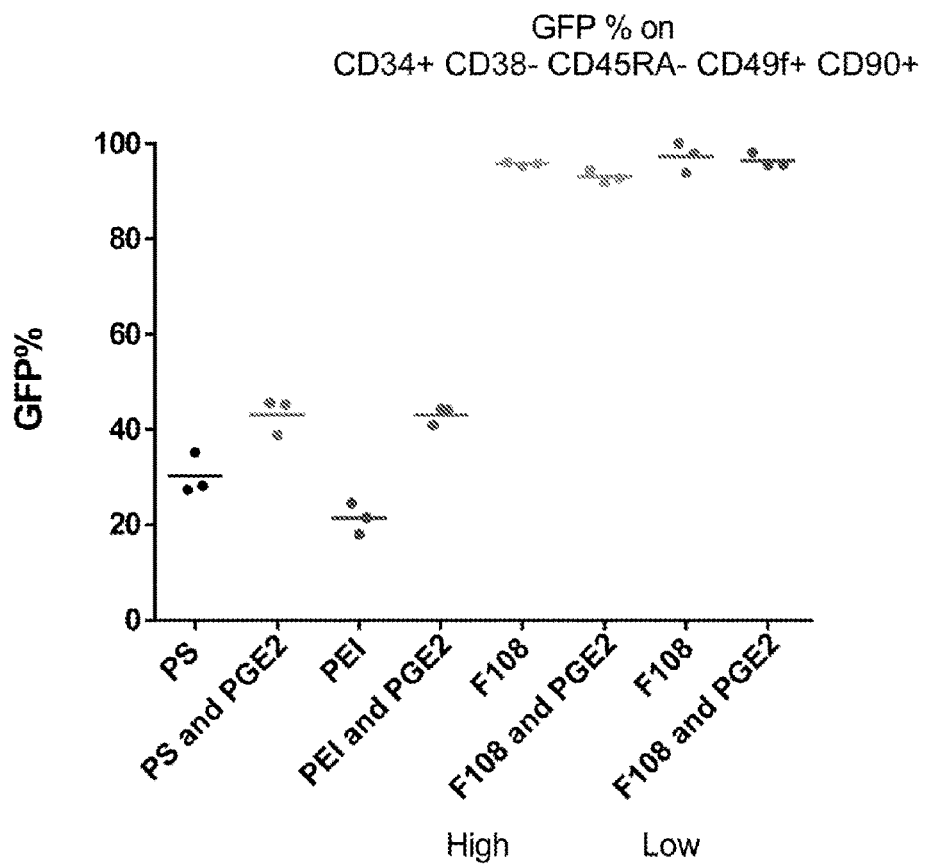
FIG. 22 shows that F108 increases transduction efficiency of phenotypic long-term HSCs ($CD34^+CD38^-CD45RA^-CD90^+CD49f^+$) with a GFP lentiviral vector.

Human CD34⁺ cells were transduced with a GFP lentiviral vector (LVV) and subsequently cultured in cytokine-containing media. After 4 days of culture, these cells were stained for cell surface markers that phenotypically characterize long-term HSCs (CD34⁺CD38⁻CD45RA⁻CD90⁺CD49f⁺). Flow cytometry analysis of the transduced cells showed that the proportion of cells expressing GFP when transduced with standard transduction conditions using protamine sulfate was approximately 30% and increased to 45% with addition of $PGE_2$. The proportion of transduced phenotypic long-term HSCs increased to >90% in cells transduced in the presence of F108, with or without the supplementation of PGE2. FIG. 22.

Example 25

F108 and $PGE_2$ Increase VCN Across HSC Lots with Different Transducibility

Human $CD34^+$ cell lots classified as low, mid or high transducers, by transducing with a lentivirus in the presence of protamine sulfate (PS). Low transducer cell lots had a VCN≤0.5 copies/diploid genome (c/dg); mid transducer cell lots had VCN between 0.5 c/dg and 1.0 c/dg; and high transducer cell lots had a VCN≥1 c/dg.

Figure 23:
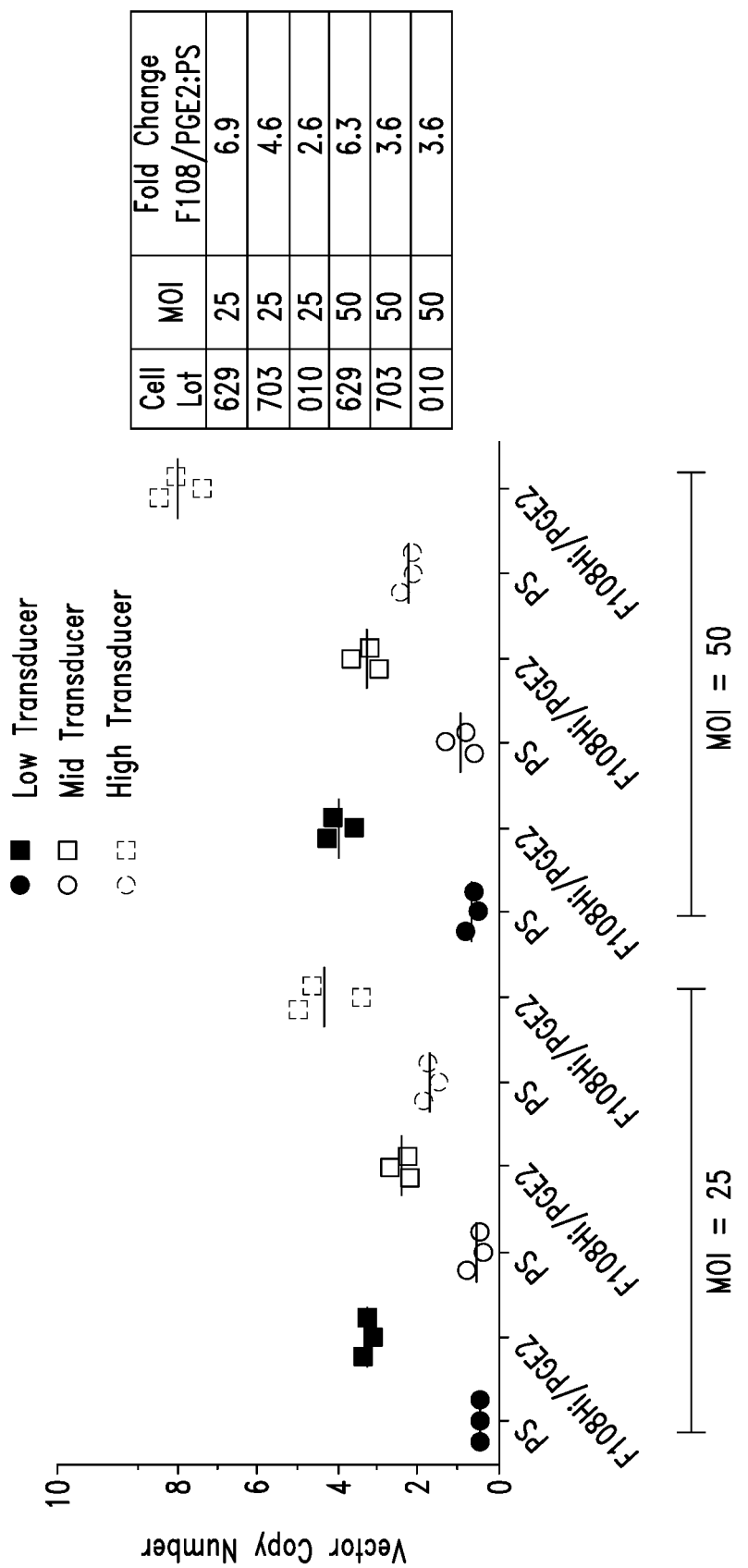
FIG. 23 shows three different cell lots (629, 703, 010) representative of low, mid and high transducers transduced with LentiGlobin BB305 at two MOIs.

Three cell lots (629, 702, and 010) representative of low, mid, and high transducers, respectively, were transduced with LentiGlobin BB305 vector at an MOI of 25 or 50. Cells were transduced using standard transduction conditions (PS) or with F108 and $PGE_2$. Increased VCN correlated with increased transducibility of the cell lot when the cells were transduced in the presence of PS, but not when the cells were transduced in the presence of F108 and $PGE_2$. The data show that the lower-transducing cell lots receive greater VCN enhancement than higher-transducing cell lots in the presence of F108 and $PGE_2$, suggesting that the VCN enhancement effect plateaus and resulted in a near normalization of drug product VCNs. FIG. 23.

Example 26

F108 and $PGE_2$ Increase Transduction Efficiency and VCN in $HCD34^+$ Cells Transduced with an X-SCID Lentiviral Vector Human $CD34^+$ cells were transduced with a lentiviral vector (LVV) comprising an EF1α promoter operably linked to a polynucleotide encoding IL2Rγ. The LVV was prepared by transient transfection (transient), or produced by producer cell lines (PrCL1 and PrCL2). Cells were prestimulated in cytokine containing media for 48 hours and transduced for 24 hours at an MOI of either 10 or 30 using either standard transduction conditions of 8 μg/mL protamine sulfate (PS) or 200 μg/mL F108 and 10 μM $PGE_2$. After transduction, cells were plated in methylcellulose and cultured for approximately 14 days to allow for hematopoietic progenitor colony formation. Colonies were imaged for enumeration and then either pooled for VCN analysis or individual colonies were plucked for individual colony qPCR to determine mean VCN and the proportion of transduced colonies (% LVV+).

Transduction in protamine sulfate yielded VCNs below 1.5; VCN increased with increasing MOI for transiently prepared LVV or LVV produced from PrCL1 but not when LVV was produced from PrCL2 (FIG. 24, top left panel). Transduction in protamine sulfate resulted in about 50-60% LVV+ colonies for transiently prepared LVV and about 20-30% LVV+ colonies when LVV from PrCL1 or PrCL2 was used (FIG. 24, top middle panel). Protamine sulfate did not significantly impact colony formation (FIG. 24, top right panel). Transduction in the presence of F108 and $PGE_2$ increased VCN greater than 2× at an MOI of 10 for transiently prepared LVV and greater than 4× at an MOI of 30 for transiently prepared LVV and LVV produced from PrCL1 or PrCL2 (FIG. 24, lower left panel). In addition, transduction at an MOI of 30 in the presence of F108 and $PGE_2$ yielded greater than 95% LVV+ colonies for transiently prepared LVV and LVV produced from PrCL1 (FIG. 24, lower middle panel). F108 and $PGE_2$ did not significantly impact colony formation (FIG. 24, lower right panel).

Example 27

F108 and $PGE_2$ Increase Transduction Efficiency and VCN in HSCS Transduced with a Tripeptidyl Peptidase (TPP1) Lentiviral Vector Human CD34+ cells were transduced with a lentiviral vector (LVV) comprising an EF1α promoter or MND promoter operably linked to a polynucleotide encoding TPP1. Cells were prestimulated in cytokine containing media for 48 hours and transduced for 24 hours at an MOI of either 5 or 15 using either standard transduction conditions of 8 μg/mL protamine sulfate (PS) or 200 μg/mL F108 and 10 μM $PGE_2$. After transduction, cells were plated in methylcellulose and cultured for approximately 14 days to allow for hematopoietic progenitor colony formation. Colonies were pooled for VCN analysis.

Transduction in protamine sulfate yielded VCNs below 1.5 and VCN increased with increasing MOI. Substantial increases in VCN were observed in cells transduced in the presence of F108 and $PGE_2$ at either MOI (FIG. 25, top left panel). After transduced cells were cultured in cytokines for 7 days; cell pellets and supernatants were assayed for TPP-1 activity. TPP-1 activity was higher in cells with higher VCNs, i.e., cells transduced in the presence of F108 and $PGE_2$ (FIG. 25, top middle and top right panels).

Mouse lineage-depleted bone marrow was transduced with the MND-TPP1 LVV at MOIs of 5, 15, or 30, in the presence of PS or F108 and $PGE_2$. VCN was increased in cytokine cultured cells at day 7 at all MOIs of 5, 15, and 30 (FIG. 25, bottom left panel). Individual colonies were plucked and analyzed by qPCR for VCN from mouse hematopoietic progenitors; F108 and $PGE_2$ increased VCN in these cells (FIG. 25, lower middle panel). F108 and $PGE_2$ also substantially increased transduction efficiency (FIG. 25, lower right panel).

Example 28

F108 and $PGE_2$ Increase Transduction Efficiency and VCN in $HCD34^+$ Cells Transduced with an ATP-Binding Cassette, Sub-Family D, Member 1 (ABCD1) Lentiviral Vector Human $CD34^+$ cells from AMN patients (FIG. 26, panels A-D), ALD patients (FIG. 26, panels E-H), and healthy donors (HD; FIG. 26, panels I-L) were transduced with a lentiviral vector (LVV) lacking a WPRE and comprising an MND promoter operably linked to a polynucleotide encoding ABCD1. Cells were prestimulated in cytokine containing media for 48 hours and transduced for 24 hours using either standard transduction conditions of 8 μg/mL protamine sulfate (PS) or 200 μg/mL F108, 10 μM $PGE_2$, or F108 and $PGE_2$. After transduction, cells were plated in methylcellulose and cultured for approximately 14 days to allow for hematopoietic progenitor colony formation or cultured in cytokine containing media for 7 days. Cultured cells were stained intracellularly for ALDP expression on day 4 or 5 and analyzed by flow cytometry. F108, $PGE_2$, and F108 and $PGE_2$ increased the number of cells expressing ALDP, which was also enhanced by increasing the MOI (FIG. 26, panels A, E, I). F108, $PGE_2$, and F108 and $PGE_2$ increased VCN at D7 in cytokine cultured cells (FIG. 26, panels B, F, J) and D14 pooled methylcellulose colonies (FIG. 26, panels C, G, K). Higher VCNs generated using the MND-ABCD1 LVV correlate with reduced colony counts (FIG. 26, panels D, H, L). FIG. 26, panels H and L show that F108 alone increased VCN with less effects on colony count, particularly at lower MOIs. Thus, in certain circumstances, for instance when high VCNs of particular LVVs are associated with decreased colony counts, poloxamers alone may be used to increase VCN at low MOIs without impacting colony formation, thereby increasing protein expression with the benefit of using less LVV.

Example 29

Targeting Particular VCNS with F108 and $PGE_2$

Human CD34+ cells were transduced with LVV at an MOI of 25 in the presence of protamine sulfate or at an MOI of 10 in the presence of F108 and $PGE_2$ with the goal of targeting similar VCNs in the end product. There was no significant difference between treatment conditions when VCN was analyzed from day 7 cytokine cultured cells or day 14 methylcellulose cultured cells (FIG. 27, left panel). There was also no significant difference in colony formation between treatment conditions (FIG. 27, middle panel).

Individual colony qPCR was used to assess any differences in composition. The mean VCNs of the products were similar. Cells transduced at an MOI of 10 with F108 and $PGE_2$ had a higher % LVV+ compared to the cells transduced at an MOI of 25 with protamine sulfate, and the distribution of individual colony VCNs was 0-4 for cells transduced at an MOI of 10 with F108 and $PGE_2$ and from 0-6 in cells transduced at an MOI of 25 with protamine sulfate (FIG. 27, right panel). Thus, F108 and $PGE_2$ can be used to decrease the cost of goods while producing a drug product having a decreased risk profile and other desirable characteristics.

Example 30

In Vivo Analysis of F127 Treated Human CD34+ CElls

As a starting material for transduction, normal human CD34+ cells are isolated by leukapheresis from a single healthy volunteer donor after mobilization with granulocyte-colony stimulating factor (G CSF). The cells are split into different aliquots, and subjected to large scale transduction with LentiGlobin BB305 LVV at a multiplicity of infection (MOI) value of about 25 to about 50 using 8 μg/mL protamine sulfate or 200 μg/mL F127 and 10 μM $PGE_2$. The HSCs are cryopreserved after transduction and subsequently administered to NSG mice after thaw, resulting in one post-transduction freeze/thaw cycle.

After transduction, the control and test drug products are thoroughly characterized. CFC cultures are assayed to determine composite VCN values, individual colony VCN values, and the % LVV+colonies. Erythroid cultures are analyzed to determine the % βA T87Q globin produced. Transduction with F127 will increase composite VCN, individual colony VCNs, and % LVV+ colonies, compared to cells transduced with protamine sulfate. Bone marrow will be characterized at 2 months and 4 months to assess VCN and % LVV+ in short-term and long-term repopulating HSCs.

Example 31

In Vivo Analysis of P105 Treated Human CD34+ Cells

As a starting material for transduction, normal human CD34+ cells are isolated by leukapheresis from a single healthy volunteer donor after mobilization with granulocyte-colony stimulating factor (G CSF). The cells are split into different aliquots, and subjected to large scale transduction with LentiGlobin BB305 LVV at a multiplicity of infection (MOI) value of about 25 to about 50 using 8 μg/mL protamine sulfate or 200 μg/mL P105 and 10 μM $PGE_2$. The HSCs are cryopreserved after transduction and subsequently administered to NSG mice after thaw, resulting in one post-transduction freeze/thaw cycle.

After transduction, the control and test drug products are thoroughly characterized. CFC cultures are assayed to determine composite VCN values, individual colony VCN values, and the % LVV+ colonies. Erythroid cultures are analyzed to determine the % PA T87Q globin produced. Transduction with P105 will increase composite VCN, individual colony VCNs, and % LVV+ colonies, compared to cells transduced with protamine sulfate. Bone marrow will be characterized at 2 months and 4 months to assess VCN and % LVV+ in short-term and long-term repopulating HSCs.

Example 32

In Vivo Analysis of F98 Treated Human CD34+ Cells

As a starting material for transduction, normal human CD34+ cells are isolated by leukapheresis from a single healthy volunteer donor after mobilization with granulocyte-colony stimulating factor (G CSF). The cells are split into different aliquots, and subjected to large scale transduction with LentiGlobin BB305 LVV at a multiplicity of infection (MOI) value of about 25 to about 50 using 8 μg/mL protamine sulfate or 200 μg/mL F98 and 10 μM $PGE_2$. The HSCs are cryopreserved after transduction and subsequently administered to NSG mice after thaw, resulting in one post-transduction freeze/thaw cycle.

After transduction, the control and test drug products are thoroughly characterized. CFC cultures are assayed to determine composite VCN values, individual colony VCN values, and the % LVV+ colonies. Erythroid cultures are analyzed to determine the % PA T87Q globin produced. Transduction with F98 will increase composite VCN, individual colony VCNs, and % LVV+ colonies, compared to cells transduced with protamine sulfate. Bone marrow will be characterized at 2 months and 4 months to assess VCN and % LVV+ in short-term and long-term repopulating HSCs.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of increasing the vector copy number (VCN) in a population of CD34+ hematopoietic stem or progenitor cells comprising culturing the cells for at least two hours in the presence of: (1) a lentiviral vector at a multiplicity of infection (MOI) of about 10 to about 30; (2) a prostaglandin $E_2(PGE_2)$, or 16,16-dimethyl $PGE_2$ ; and (3) poloxamer 338, wherein the increase of VCN achieved by culturing the cells for at least two hours in the presence of the lentiviral vector, poloxamer 338 and one of $PGE_2$ or 16,16-dimethyl $PGE_2$ is further enhanced beyond the increased VCN achieved by culturing the cells for at least two hours in the presence of the lentiviral vector and one of PGE$_2$ or 16,16-dimethyl PGE$_2$ and the absence of poloxamer 338.

2. The method of claim 1, wherein the hematopoietic stem or progenitor cells are selected for CD34$^+$ expression prior to transduction.

3. The method of claim 1, wherein the CD34+ hematopoietic stem or progenitor cells comprise the B-globin alleles selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ and $\beta^S/\beta^S$.

4. The method of claim 1, wherein the CD34+ hematopoietic stem or progenitor cells comprise the B-globin alleles selected from the group consisting of: $\beta^E/\beta^0$, $\beta^0/\beta^0$, $\beta^E/\beta^E$, $\beta^E/\beta^+$, $\beta^0/\beta^+$, and $\beta^+/\beta^+$.

5. The method of claim 1, wherein the lentiviral vector is cultured with the cells at an MOI of about 10 to about 25, or about 10 to about 20.

6. The method of claim 1, wherein the lentiviral vector is cultured with the cells at an MOI of about 10, about 11, about 12, about 13, about 14, about 15, about 16, about 17, about 18, about 19, about 20, about 21, about 22, about 23, about 24, about 25, about 26, about 27, about 28, about 29 or about 30.

7. The method of claim 1, wherein the lentiviral vector is derived from an HIV-1 lentivirus.

8. The method of claim 1, wherein the lentiviral vector comprises:
   a) a 5' long terminal (LTR);
   b) a Psi ($\Psi$) packaging signal;
   c) an RNA export element;
   d) a lentiviral central polypurine tract (cPPT);
   e) a promoter operably linked to a polynucleotide of interest; and
   f) a SIN 3' LTR.

9. The method of claim 1, wherein the lentiviral vector comprises:
   a) a 5' long terminal (LTR) comprising a cytomegalovirus (CMV) promoter;
   b) a Psi ($\Psi$) packaging signal;
   c) a Rev response element (RRE);
   d) a lentiviral central polypurine tract (cPPT);
   e) a human $\beta$-globin LCR and human $\beta$-globin promoter operably linked to a polynucleotide encoding a globin; and
   f) a self-inactivating (SIN) 3' LTR that comprises a synthetic polyadenylation sequence.

10. The method of claim 9, wherein the globin is selected from the group consisting of: a human $\beta$-globin, a human $\delta$-globin, a human $\gamma$-globin, a human $\beta^{A\text{-}T87Q}$-globin, a human $\beta^{A\text{-}G16D/E22A/T87Q}$-globin, and a human $\beta^{A\text{-}T87Q/K95E/K120E}$-globin.

11. The method of claim 1, wherein the lentiviral vector is an AnkT9W vector, a T9Ank2W vector, a TNS9 vector, a lentiglobin HPV569 vector, a lentiglobin BB305 vector, a BG-1 vector, a BGM-1 vector, a d432BA$\gamma$ vector, a mLAR$\beta\Delta\gamma$V5 vector, a GLOBE vector, a G-GLOBE vector, a $\beta$AS3-FB vector, a V5 vector, a V5m3 vector, a V5m3-400 vector, a G9 vector, or a BCL11A shmir vector.

12. The method of claim 1, wherein the cells are cultured in the presence of PGE$_2$.

13. The method of claim 1, wherein the cells are cultured in the presence of 16,16-dimethyl PGE$_2$.

14. The method of claim 1, wherein the PGE$_2$ or 16,16-dimethyl PGE$_2$ is present in the culture in a concentration of about 10 μM to about 100 μM.

15. The method of claim 14, wherein the PGE$_2$ or 16,16-dimethyl PGE$_2$ is present in the culture in a concentration of about 10 μM to about 50 μM.

16. The method of claim 1, wherein the poloxamer 338 is present in the culture in a concentration of about 50 μg/mL to about 1000 μg/mL.

17. The method of claim 16, wherein the poloxamer 338 is present in the culture in a concentration of about 62.5 μg/mL to less than 1000 μg/mL.

* * * * *